(12) United States Patent
Udd

(10) Patent No.: US 8,989,528 B2
(45) Date of Patent: Mar. 24, 2015

(54) OPTICAL FIBER GRATING SENSORS AND METHODS OF MANUFACTURE

(75) Inventor: Eric Udd, Fairview, OR (US)

(73) Assignee: Hansen Medical, Inc., Mountain View, CA (US)

( * ) Notice: Subject to any disclaimer, the term of this patent is extended or adjusted under 35 U.S.C. 154(b) by 1164 days.

(21) Appl. No.: 12/236,478

(22) Filed: Sep. 23, 2008

(65) Prior Publication Data

US 2009/0123111 A1 May 14, 2009

Related U.S. Application Data

(60) Provisional application No. 61/003,008, filed on Nov. 13, 2007.

(51) Int. Cl.
| | |
|---|---|
| *G02B 6/00* | (2006.01) |
| *G02F 1/295* | (2006.01) |
| *G01D 5/353* | (2006.01) |
| *A61B 5/06* | (2006.01) |
| *A61B 19/00* | (2006.01) |

(52) U.S. Cl.
CPC ............ *G01D 5/35303* (2013.01); *A61B 5/06* (2013.01); *A61B 2019/2211* (2013.01); *A61B 2019/2234* (2013.01); *A61B 2019/2296* (2013.01); *A61B 2019/464* (2013.01); *A61B 2019/5261* (2013.01)
USPC .............................................. 385/13; 385/10

(58) Field of Classification Search
USPC .......... 385/10, 12, 13, 37; 604/528, 523–525, 604/534; 901/47
See application file for complete search history.

(56) References Cited

U.S. PATENT DOCUMENTS

| | | |
|---|---|---|
| 3,807,390 A | 4/1974 | Ostrowski et al. |
| 4,443,698 A | 4/1984 | Schiffner |
| 4,761,073 A | 8/1988 | Meltz et al. |
| 4,960,410 A | 10/1990 | Pinchuk |
| 4,996,419 A | 2/1991 | Morey |

(Continued)

FOREIGN PATENT DOCUMENTS

| | | |
|---|---|---|
| EP | 1103223 A2 | 5/2001 |
| WF | WO 2007109778 | 9/2007 |

(Continued)

OTHER PUBLICATIONS

PCT Invitation to Pay Additional Fees from the International Search Authority for PCT/US2008/082236, Applicant Hansen Medical Inc., Form PCT/ISA/206 and Annex to Form PCT/ISA/206, dated Jul. 6, 2009 (9 pages).
Turan Erdogan, "Fiber Grating Spectra", Journal of Lightwave Technology, vol. 15, No. 8, Aug. 1997, IEEE Service Center, New York, NY (18 pages).
PCT International Search Report and Written Opinion for PCT/US2008/082236, Applicant Hansen Medical, Inc., Forms PCT/ISA/210, 220, and 237 dated Oct. 16, 2009 (19 pages).

(Continued)

*Primary Examiner* — Robert Tavlykaev
(74) *Attorney, Agent, or Firm* — Scott M. Smith; Dorsey & Whitney LLP

(57) ABSTRACT

Systems and methods comprise or involve optical fibers having Bragg gratings. The optical fibers can be assembled in a parallel manner into a fiber sensor configuration. Bragg gratings can be written onto different cores of optical fibers. Bragg gratings may be written at a same or nearly same axial position for all optical fibers in the configuration and may be written at the same time and may have a substantially equal index of refraction variation and unequal lengths. Spaced Bragg gratings may also have characteristic sidelobe spectrums for tagging the respective gratings. Gratings can also be written at different wavelengths and over another grating at the same location.

21 Claims, 54 Drawing Sheets

(56) References Cited

U.S. PATENT DOCUMENTS

| | | | |
|---|---|---|---|
| 5,003,982 A | 4/1991 | Halperin | |
| 5,007,705 A | 4/1991 | Morey et al. | |
| 5,066,133 A | 11/1991 | Brienza | |
| 5,067,346 A | 11/1991 | Field | |
| 5,118,931 A | 6/1992 | Udd et al. | |
| 5,144,960 A | 9/1992 | Mehra et al. | |
| 5,267,339 A | 11/1993 | Yamauchi et al. | |
| 5,380,995 A | 1/1995 | Udd et al. | |
| 5,397,891 A | 3/1995 | Udd et al. | |
| 5,401,956 A | 3/1995 | Dunphy et al. | |
| 5,433,215 A | 7/1995 | Athanasiou et al. | |
| 5,492,131 A | 2/1996 | Galel | |
| 5,563,967 A | 10/1996 | Haake | |
| 5,591,965 A | 1/1997 | Udd | |
| 5,627,927 A | 5/1997 | Udd | |
| 5,630,783 A | 5/1997 | Steinberg | |
| 5,798,521 A | 8/1998 | Froggatt | |
| 5,810,716 A | 9/1998 | Mukherjee et al. | |
| 5,828,059 A | 10/1998 | Udd | |
| 5,911,694 A | 6/1999 | Ikeda et al. | |
| 5,917,978 A | 6/1999 | Rutterman | |
| 6,035,082 A | 3/2000 | Murphy et al. | |
| 6,068,604 A | 5/2000 | Krause et al. | |
| 6,069,420 A | 5/2000 | Mizzi et al. | |
| 6,144,026 A | 11/2000 | Udd et al. | |
| 6,215,943 B1 | 4/2001 | Crotts et al. | |
| 6,256,090 B1 | 7/2001 | Chen et al. | |
| 6,275,511 B1 | 8/2001 | Pan et al. | |
| 6,275,628 B1 | 8/2001 | Jones et al. | |
| 6,301,420 B1 | 10/2001 | Greenaway et al. | |
| 6,366,722 B1 | 4/2002 | Murphy et al. | |
| 6,389,187 B1 | 5/2002 | Greenaway et al. | |
| 6,404,956 B1 | 6/2002 | Brennan, III et al. | |
| 6,426,796 B1 | 7/2002 | Pulliam et al. | |
| 6,470,205 B2 | 10/2002 | Bosselmann et al. | |
| 6,471,710 B1 | 10/2002 | Bucholtz | |
| 6,545,760 B1 | 4/2003 | Froggatt et al. | |
| 6,550,342 B2 | 4/2003 | Croteau et al. | |
| 6,571,639 B1 | 6/2003 | May et al. | |
| 6,611,700 B1 | 8/2003 | Vilsmeier et al. | |
| 6,671,055 B1 | 12/2003 | Wavering et al. | |
| 6,716,178 B1 | 4/2004 | Kilpatrick et al. | |
| 6,726,699 B1 | 4/2004 | Wright et al. | |
| 6,796,963 B2 | 9/2004 | Carpenter et al. | |
| 6,817,981 B2 | 11/2004 | Luce | |
| 6,826,343 B2 | 11/2004 | Davis et al. | |
| 6,850,817 B1 * | 2/2005 | Green | 700/245 |
| 6,868,195 B2 | 3/2005 | Fujita | |
| 6,876,786 B2 | 4/2005 | Chliaguine et al. | |
| 6,888,623 B2 | 5/2005 | Clements | |
| 6,892,090 B2 | 5/2005 | Verard et al. | |
| 6,898,337 B2 | 5/2005 | Averett et al. | |
| 6,923,048 B2 | 8/2005 | Willsch et al. | |
| 6,965,708 B2 | 11/2005 | Luo et al. | |
| 6,974,455 B2 | 12/2005 | Garabedian et al. | |
| 6,987,897 B2 | 1/2006 | Elster et al. | |
| 7,010,182 B2 | 3/2006 | Pennington | |
| 7,038,190 B2 | 5/2006 | Udd et al. | |
| 7,042,573 B2 | 5/2006 | Froggatt | |
| 7,046,866 B2 | 5/2006 | Sahlgren et al. | |
| 7,154,081 B1 | 12/2006 | Friedersdorf et al. | |
| 7,330,245 B2 | 2/2008 | Froggatt | |
| 7,538,883 B2 | 5/2009 | Froggatt | |
| 7,561,276 B2 | 7/2009 | Boyd | |
| 7,742,805 B2 | 6/2010 | Furnish et al. | |
| 7,772,541 B2 | 8/2010 | Froggatt et al. | |
| 7,781,724 B2 | 8/2010 | Childers et al. | |
| 7,789,875 B2 | 9/2010 | Brock et al. | |
| 8,050,523 B2 | 11/2011 | Younge et al. | |
| 2001/0021843 A1 | 9/2001 | Bosselmann et al. | |
| 2003/0055360 A1 | 3/2003 | Zeleznik et al. | |
| 2003/0188585 A1 | 10/2003 | Esser et al. | |
| 2003/0195502 A1 | 10/2003 | Garabedian et al. | |
| 2004/0034300 A1 | 2/2004 | Verard et al. | |
| 2004/0165810 A1 | 8/2004 | Fujita | |
| 2004/0208413 A1 | 10/2004 | Scandale et al. | |
| 2005/0036140 A1 | 2/2005 | Elster et al. | |
| 2005/0054934 A1 | 3/2005 | Furnish et al. | |
| 2005/0085728 A1 | 4/2005 | Fukuda | |
| 2005/0201664 A1 | 9/2005 | Udd et al. | |
| 2005/0222554 A1 | 10/2005 | Wallace et al. | |
| 2005/0254575 A1 | 11/2005 | Hannuksela et al. | |
| 2006/0013523 A1 | 1/2006 | Childers et al. | |
| 2006/0036164 A1 | 2/2006 | Wilson et al. | |
| 2006/0036213 A1 | 2/2006 | Viswanathan et al. | |
| 2006/0100610 A1 | 5/2006 | Wallace et al. | |
| 2006/0142897 A1 * | 6/2006 | Green | 700/245 |
| 2006/0161045 A1 | 7/2006 | Merril et al. | |
| 2006/0200049 A1 | 9/2006 | Leo et al. | |
| 2006/0293864 A1 | 12/2006 | Soss | |
| 2007/0060847 A1 | 3/2007 | Leo et al. | |
| 2007/0156019 A1 | 7/2007 | Larkin et al. | |
| 2007/0197896 A1 | 8/2007 | Moll et al. | |
| 2007/0197939 A1 | 8/2007 | Wallace et al. | |
| 2007/0201793 A1 | 8/2007 | Askins et al. | |
| 2007/0233044 A1 | 10/2007 | Wallace et al. | |
| 2007/0265503 A1 * | 11/2007 | Schlesinger et al. | 600/182 |
| 2008/0009750 A1 | 1/2008 | Aeby et al. | |
| 2008/0218770 A1 | 9/2008 | Moll et al. | |
| 2008/0285909 A1 | 11/2008 | Younge et al. | |
| 2009/0123111 A1 | 5/2009 | Udd | |
| 2010/0106140 A1 * | 4/2010 | Odland et al. | 604/523 |

FOREIGN PATENT DOCUMENTS

| | | | | |
|---|---|---|---|---|
| WO | 9202276 A1 | 2/1992 | | |
| WO | 0133165 A1 | 5/2001 | | |
| WO | WO 01/33165 A1 * | 5/2001 | | G01B 11/26 |
| WO | 0219898 A2 | 3/2002 | | |
| WO | 0247751 A2 | 6/2002 | | |
| WO | 03065095 A2 | 8/2003 | | |
| WO | 2004001469 A1 | 12/2003 | | |
| WO | 2005055605 A1 | 6/2005 | | |
| WO | 2005087128 A1 | 9/2005 | | |
| WO | 2006092707 A1 | 9/2006 | | |
| WO | 2006099056 A2 | 9/2006 | | |
| WO | 2007015139 A2 | 2/2007 | | |
| WO | WO 2007045028 | 4/2007 | | |
| WO | 2008094949 A2 | 8/2008 | | |
| WO | 2008131303 A2 | 10/2008 | | |

OTHER PUBLICATIONS

Papers from file history for U.S. Appl. No. 12/507,727, Inventor Randall Schlesinger et al, filed Jul. 22, 2009, including (15 pages): Non-Final Rejection dated Dec. 22, 2010.

Papers from file history for U.S. Appl. No. 12/106,254, Inventory Robert G. Younge et al, filed Apr. 18, 2008, including (57 pages): Non-Final Rejection dated Jun. 19, 2009; Response to Non-Final, Rejection dated Jun. 19, 2009, response sub. Oct. 16, 2009; Final Rejection dated Apr. 2, 2010; Response to Final Rejection dated Jun. 19, 2009, response submitted on Aug. 30, 2010; Notices of Allowance dated Sep. 17, 2010 and Dec. 28, 2010.

Papers from file history for U.S. Appl. No. 11/690,116, Inventor Randall Schlesinger et al., filed Mar. 22, 2007, including (45 pages): Non-Final Rejection dated Apr. 28, 2010; Response to Non-Final Rejection dated Apr. 28, 2010, response submitted Aug. 30, 2010; Final Rejection dated Nov. 19, 2010.

Papers from file history for CN Application No. 200780009956.6, Applicant Hansen Medical, Inc., filed Mar. 22, 2007,including (20 pages): Office action dated Feb. 5, 2010, translation only, translation provided by foreign associate; Office action dated Dec. 14, 2010, translation only, translation provided by foreign associate.

"Distributed Sensing System Sensor Array Specification", www.lunainnovations.com, pp. 1-3.

"Fiber Optic Interferometer Fabry-Perot", http://physics-animations.com/sensors/English/interf.htm, pp. 1-5.

File history of U.S. Appl. No. 11/450,072, filed Jun. 9, 2006, published as 2008-0009750, on Jan. 10, 2008.

File history of U.S. patent No. 5,798,521 (U.S. Appl. No. 08/086,732) issued on Aug. 25, 1998.

File history of U.S. Patent No. 6,256,090 (U.S. Appl. No. 09/127,083), issued on Jul. 3, 2001.

(56) References Cited

OTHER PUBLICATIONS

File history of U.S. Patent No. 6,470,205 (U.S. Appl. No. 09/804,804), Issued on Oct. 22, 2002.
PCT International Search Report and Written Opinion for PCT/US2007/064728, Applicant Hansen Medical, Inc., Form PCT/ISA/220, 210 and 237, dated Jul. 31, 2007 (13 pages).
PCT International Search Report and Written Opinion for PCT/US2008/060936, Applicant Hansen Medical, Inc., Form PCT/ISA/220, 210 and 237, dated Nov. 6, 2009 (12 pages).
Abouraddy, A. F. et al., "Towards multimaterial multifunctional fibres that see, hear, sense, and communicate", Nature Materials 6, Publication date: May 2007, pp. 336-342.
Berthold, III, John W., "Historical Review of Microbend Fiber-Optic Sensors", Journal of Lightwave Technology, Jul. 1995, pp. 1193-1199, vol. 13 No. 7.
Blandino, J. R. et al., "Three-dimensional shape sensing for inflatable booms", 46th AIAA/ASME/ASCE/AHS/ASC Structures, Structural Dynamics & Materials Conference, Austin, Texas, Conference Dates: Apr. 18-21, 2005, pp. 1-10.
Capouilliet, et al., "A Fiber Bragg Grating Measurement System for Monitoring Optical Fiber Strain", IWCS/FOCUS Internet conference Nov. 12-15, 2001 , pp. 240-248.
Childers, Brooks A. et al., "Recent development in the application of optical frequency domain reflectometry to distributed Bragg grating sensing", Luna Innovations and NASA Langley Research Center joint PowerPoint presentation.
Danisch, et al., "Bend Enhanced Fiber Optic Sensors in a Teleoperation Application", Fiber Optic and Laser Sensors XI, 1993, pp. 73-85, SPIE vol. 2070.
Danisch, et al., "Spatially continuous six degree of freedom position and orientation sensor", Sensor Review, 1999, pp. 106-112, vol. 19.
Davis, et al., "Fiber-optic bragg grating array for shape and vibration mode sensing", May 1994, pp. 94-102, Proceedings SPIE vol. 2191.
Davis, Claire, "Strain Survey of an F/A-18 Stabilator Spindle Using High Density Bragg Grating Arrays", Feb. 2005, Australia.
Duncan, Roger, "Sensing Shape: Fiber-Bragg-grating sensor arrays monitor shape at a high resolution", Spie's OE Magazine, Sep. 2005, pp. 18-21.
Duncan, Roger R. et al., "A distributed sensing technique for aerospace applications", 42nd AIAA Aerospace Sciences Meeting and Exhibit, Conference dates: Jan. 5-8, 2004, Reno, Nevada.
Duncan, Roger R. et al., "Characterization of a fiber optic shape and position sensor", Conference Title: Smart Structures and Materials 2006: Smart Sensor Monitoring Systems and Applications; San Diego, CA, Conference Date: Monday Feb. 27, 2006, Published in: Proc. SPIE, vol. 6167, 616704 (2006); doi:10.1117/12.658535, Online Publication Date: Mar. 30, 2006.
Duncan, Roger R. et al., "Fiber-optic shape and position sensing", Proceedings of the 5th International Conference on Structural Health Monitoring (2005), Structural Health Monitoring, 2005: Advancements and Challenges for Implementation, Copyright 2005.
Duncan, Roger R. et al., "High-accuracy fiber-optic shape sensing", Conference Title: Sensor Systems and Networks: Phenomena, Technology, and Applications for NDE and Health Monitoring 2007, San Diego, California, USA, Conference Date: Monday Mar. 19, 2007, Published in: Proc. SPIE, vol. 6530, 65301 S (2007); doi:10.1117/12.720914, Online Publication Date: Apr. 10, 2007.
Duncan, Roger R. et al., "Use of high spatial resolution fiber-optic shape sensors to monitor the shape of deployable space structures", Space Technology and Applications Int.Forum-STAIF 2005: Conf. Thermophys in Micrograv; Conf Comm/Civil Next Gen.Space Transp; 22nd Symp Space Nuci.Powr Propuls.; Conf.Human/Robotic Techn.Nat'l Vision Space Expl.; 3rd Symp Space Colon.; 2nd Symp.New Frontiers. ALP Conference Proceedings, Feb. 2005, pp. 880-886, vol. 746.
Flockhart, G.M.H. et al., "Two-axis bend measurement with Bragg gratings in multicore optical fiber", Optics Letters, Mar. 15, 2003, pp. 387-389, vol. 28 No. 6, Optical Society of America.
Froggatt, Mark et al., "Distributed measurement of static strain in an optical fiber with multiple Bragg gratings at nominally equal wavelengths", Applied Optics, Apr. 1, 1998, pp. 1741-1746, vol. 37 No. 10.
Froggatt, Mark et al., "High-spatial-resolution distributed strain measurement in optical fiber with Rayleigh scatter", Applied Optics, Apr. 1, 1998, pp. 1735-1740, vol. 37 No. 10.
Froggatt, Mark, "Intracore and extracore examination of fiber gratings with coherent detection", Thesis (PhD), The Institute of Optics, Rochester, New York 2000.
Froggatt, Mark E. et al., "Distributed Fiber-Optic Strain and Temperature Sensors Using Photoinduced Bragg Gratings", Feb. 1995, Blacksburg Virginia.
Gander, et al., "Bend Measurement using multicore optical fiber", Proceedings of OFS-12, Oct. 1997, pp. 166-169.
Gander, M. J. et al., "Measurement of bending in two dimensions using multicore optical fibre", European Workshop on Optical Fibre Sensors, Jun. 1998, p. 64-68, Proc. SPIE vol. 3483.
Gifford, et al., "Swept-wavelength interferometric interrogation of fiber Rayleigh scatter for distributed sensing applications", 2007, pp. 67700E-1-67700E-9, Proc. Of SPIE Col. 6770.
Grant, J. et al., "Investigation of structural properties of carbon-epoxy composites using fiber-bragg gratings", Applications of Photonic Technology 5, Publication Date: Feb. 17, 2003, pp. 191-199, Proceedings SPIE vol. 4833.
Grobnic, et al., "Localized High Birefringence Induced in SMF-28 Fiber by Femtosecond IR Laser Exposure of the Cladding", Journal of Lightwave Technology, vol. 25, No. 8, Aug. 2007, pp. 1996-2001.
Grossman, et al., "Development of microbend sensors for pressure, load, displacement measurements in civil engineering", May 1994, pp. 112-125, Proceedings SPIE vol. 2191.
Hayano, et al., "Structural Health Monitoring System Using FBG Sensor Simultaneous Detection of Acceleration and Strain", Department of System Design Engineering, Keio University. (14 pages).
Heo, Jin-Seok et al., "Design of TR-EFPI fiber optic pressure sensor for the medical application", International Journal of Human-friendly Welfare Robotic Systems, Published: 2002, pp. 2-7, vol. 3, No. 2.
Hill, Kenneth O. et al., "Fiber Bragg Grating Technology Fundamentals and Overview", Journal of Lightwave Technology, Aug. 1997, pp. 1263-1276, vol. 15 No. 8.
Hotate, Kazuo et al., "Proposal and experimental verification of Bragg wavelength distribution measurement within a long-length FBG by synthesis of optical coherence function", Optics Express, May 26, 2008, pp. 7881-7887, vol. 16 No. 11.
Huang, S. et al., "Continuous arbitrary strain profile measurements with fiber bragg gratings", Smart Materials and Structures, Publication Date: Apr. 1998, pp. 248-256, vol. 7, No. 2.
Ivanoff, et al., "Tunable POL of Twisted-Tilted Fiber Gratings", IEEE Photonics Technology Letters, vol. 15, No. 6, Jun. 2003, pp. 828-830.
Janssen, et al., "Signal Averaging in the Undergraduate Laboratory", Europe Journal of Physics, 9 (1988), pp. 131-134.
Katsuki, et al., "The Experimental Research on the Health Monitoring of the Concrete Structures Using Optical Fiber Sensor", BAM International Symposium (NOTCE 2003), Non-destructive Testing in Civil Engineering, Sep. 16-19, 2003.
Kersey, Alan D. et al., "Fiber Grating Sensors", Journal of Lightwave Technology, Aug. 1997, pp. 1442-1463 vol. 15 No. 8.
Kim, Youngmin et al., "Design for manufacture of micromachined Fabry-Perot cavity-based sensors", Sensors and actuators. A, Physical, ISSN 0924-4247, 1995, pp. 141-146 [(article)], vol. 50, n°1-2.
Kim, Youngmin et al., "Micromachined Fabry-Perot Cavity Pressure Transducer", IEEE Photonics Technology Letters, Dec. 1995, pp. 1471-1473, vol. 7 No. 12.
Kirby, et al., "Optimal sensor layout for shape estimation form strain sensors", Smart Structures and Materials, Mar. 1995, pp. 367-376, Proc. SPIE vol. 2444.
Klute, Sandra M. et al., "Fiber-optic shape sensing and distributed strain measurements on a morphing chevron", 44th AIAA Aerospace Sciences Meeting and Exhibit, Conference dates: Jan. 9-12, 2006, pp. 1-25, Reno, Nevada.

(56) References Cited

OTHER PUBLICATIONS

Kreger, et al., "Distributed strain and temperature sensing in plastic optical fiber using Rayleigh scattering", Apr. 2009, pp. 73160A-1-73160A-8, Proc. Of SPIE 7316.

Kreger, et al., "High-resolution extended distance distributed fiber-optic sensing using Rayleigh backscatter", Apr. 2007, pp. 65301 R-1-65301 R-10, Proc. Of SPIE vol. 6530.

Kunzler, et al., "Damage Evaluation and Analysis of Composite Pressure Vessels Using Fiber Bragg Gratings to Determine Structural Health", Proceedings of SPIE, vol. 5758, Jan. 2005 (10 pages).

Lawrence, et al., "Multi-parameter sensing with fiber bragg gratings", 1996, pp. 24-31, Proceedings of SPIE vol. 2872.

Lawrence, C.M. et al., "A Fiber Optic Sensor for Transverse Strain Measurement", Experimental Mechanics, Sep. 1999, pp. 202-209, vol. 39 No. 3.

Lee, Garret et al., "Intraoperative Use of Duel Fiberoptic Catheter for Simultaneous In Vivo Visualization and Laser Vaporization of Peripheral Atherosclerotic Obstructive Disease", Catheterization and Cardiovascular Diagnosis, 1984, pp. 11-16.

Lequime, M. et al., "Fiber optic pressure and temperature sensor for down-hole applications", Fiber Optic Sensors: Engineering and Applications, Publication Date: Aug. 1, 1991, pp. 244-249, Proceedings SPIE vol. 1511.

Lopatin, Craig M. et al., "Distributed Measurement of Strain in Smart Materials Using Rayleigh Scattering", 32 International SAMPE Technical Conference, Nov. 2000, pp. 231-241.

Maas, Ad A., "Shape measurement using phase shifting speckle interferomentry", Laser Interferometry IV: Computer-Aided Interferometry, Jan. 1, 1992, pp. 558-568, Proceedings SPIE vol. 1553.

MacDonald, et al., "Frequency domain optical reflectometer", Applied Optics, vol. 20, No. 10, May 15, 1981, pp. 1840-1844.

Measures, Raymond et al., "Fiber Optic Strain Sensing", Fiber Optic Smart Structures, 1995, pp. 171-247, John Wiley & Sons Inc.

Mihailov, et al., UV-induced polarization-dependent loss (POL) in tilted fibre Bragg gratings: application of a PDL equaliser, IEE Proc.-Optoelectron., vol. 149, No. 5/6, Oct./Dec. 2002, pp. 211-216.

Miller, et al., "Fiber-optic shape sensing for flexible structures", Feb. 1989, pp. 399-404, SPIE 1170.

Miller, Gary A. et al., "Shape Sensing Using Distributed Fiber Optic Strain Measurements", Second European Workshop on Optical Fibre Sensors, Proceedings of the SPIE, Jun. 2004, pp. 528-531, vol. 5502.

Morey, "Fiber-optic bragg grating sensors", 1989, pp. 98-107, SPIEL Col. 1169.

Ohn, M.M. et al., "Arbitrary strain profile measurement within fibre gratings using interferometric Fourier transform technique", Electronics Letters, Jul. 3, 1997, pp. 1242-1243, vol. 33 No. 14.

Pinet, Eric et al., "True challenges of disposable optic fiber sensors for clinical environment", Third European Workshop on Optical Fibre Sensors, Antonello Cutolo; Brian Culshaw; Jose Miguel López-Higuera, Editors, 66191 Q, Publication Date: Jul. 2, 2007, pp. 66191Q-1-66191Q4, Proceedings SPIE vol. 6619.

Posey, Jr., R. et al., "Strain sensing based on coherent Rayleigh scattering in an optical fibre", Electronics Letters, Sep. 28, 2000, pp. 1688-1689, vol. 36 No. 20.

Raum, Matt et al., "Performance Analysis of a Fiber-Optic Shape Sensing Systems", cited as reference of 'Fiber-optic shape sensing and distributed strain measurements on a morphing chevron', Collection of Technical papers-44th AIAA, vol. 10, 2006.

Raum, Matthew T. "Error Analysis of Three Dimensional Shape Sensing Algorithm", Virginia Tech, Apr. 26, 2005.

Satava, "How the Future of Surgery is Changing: Robotics, Telesurgery, Surgical Simulators and Other Advanced Technologies", May 2006, pp. 1-21.

Sato, T. et al., "Ground strain measuring system using optical fiber sensors", Smart Structures and Materials 2000: Sensory Phenomena and Measurement Instrumentation for Smart Structures and Materials, Mar. 1999, pp. 470-479, Proceedings SPIE vol. 3670.

Schreiber, et al., "Stress-induced Birefringence in Large-mode-area Microstructured Optical Fibers", Optics Express, May 16, 2005, pp. 3637-3646, vol. 13 No. 10.

Schulz, et al., "Advanced Fiber Grating Strain Sensor Systems for Bridges, Structures, and Highways", Proceedings of SPIE 3325, 212 (1998).

Schulz, et al., "Health monitoring of adhesive joints using multi-axis fiber grating strain sensor system", Jan. 1999, pp. 41-52, Proceedings of SPIE vol. 3586.

Soller, et al., "High Resolution Optical Frequency Domain Reflectometry for Characterization of Components and Assemblies", Optics Express, Jan. 24, 2005, pp. 666-674, vol. 13 No. 2.

Soller, Brian J. et al., "Optical frequency domain reflectometry for single- and multi-mode avionics fiber-optics applications", Avionics Fiber-Optics and Photonics, Publication Date: Sep. 12-14, 2006, pp. 38-39, IEEE Conference.

Sorin, W. V., "Survey of Different Techniques", Optical Reflectometry for Component Characterization, Fiber Optic Test and Measurement, Dennis Derickson (editor), 1997, Chapter 10, Section 10.5, pp. 424-429.

Tian, X. G. et al., "Torsion Measurement Using Fiber Bragg Grating Sensors", Experimental Mechanics, Sep. 2001, pp. 248-253, vol. 41 No. 3.

Trimble, "Successful fiber sensor for medical applications", May 1993, pp. 147-150, Proceedings SPIE vol. 1886.

Udd, et al., "Usage of Multi-Axis Fiber Grating Strain Sensors to Support Nondestructive Evaluation of Composite Parts and Adhesive Bond Lines", Structural Health Monitoring Workshop, Stanford University, p. 972, DEStech Publications, 2003 (9 pages).

Udd, Eric, "Good Sense", Spie's OE Magazine, Aug. 2002, pp. 27-30.

Udd, Eric et al., "Multidimensional strain field measurements using fiber optic grating sensors", Smart Structures and Materials 2000: Sensory Phenomena and Measurement Instrumentation for Smart Structures and Materials, Publication Date: Jun. 12, 2000, pp. 254-262, Proceedings SPIE vol. 3986.

Udd, Eric et al., "Progress on developing a multiaxis fiber optic strain sensor", Third Pacific Northwest Fiber Optic Sensor Workshop, Publication Date: Sep. 2, 1997, pp. 50-56, Proceedings SPIE vol. 3180.

Walker, et al., "Shaping the radiation field of tilted fiber Bragg gratings", J. Opt. Soc. Am. B, vol. 22, No. 5, May 2005, pp. 962-975.

Wippich, et al., "Tunable Lasers and Fiber-Bragg-Grating Sensors", The Industrial Physicist, Jun./Jul. 2003, pp. 24-27.

Wong, V.V. et al., "Distributed Bragg grating integrated-optical filters: Synthesis and fabrication", American Vacuum Society, Nov./Dec. 1995, pp. 2859-2864, vol. 13 No. 6.

Wu, Mengchou et al., "Fabrication of self-apodized short-length fiber Bragg gratings", Applied Optics, Sep. 1, 2003, pp. 5017-5023, vol. 42, No. 25.

Xu, Juncheng et al., "Miniature fiber optic pressure and temperature sensors", Fiber Optic Sensor Technology and Applications IV, Publication Date: Nov. 10, 2005, pp. 600403-1-600403-6, Proceedings SPIE vol. 6004.

Xue, et al., "Simultaneous Measurement of Stress and Temperature with a Fiber Bragg Grating Based on Loop Thin-Wall Section Beam", Mar. 2, 2006, pp. 1-16.

Ye, et al., "A Polarization-maintaining Fiber Bragg Grating Interrogation System for Multi-Axis Strain Sensing", Measurement Science and Technology, Aug. 7, 2002, pp. 1446-1449.

Zhang, Lun-Wei et al., "FBG Sensor Devices for Spatial Shape Detection of Intelligent Colonscope", Apr. 2004, pp. 835-840, New Orleans, Louisiana.

Zhang, Lun-Wei "Novel shape detection systems based on FBG sensor net for intelligent endoscope", Journal of Shanghai University (English Edition), Apr. 2006, pp. 154-155, vol. 10 No. 2.

Zhang, Yan et al., "Fiber-Bragg-grating-based seismic geophone for oil/gas prospecting", Optical Engineering, Aug. 2006, pp. 84404-1-84404-4, vol. 45 No. 8.

* cited by examiner

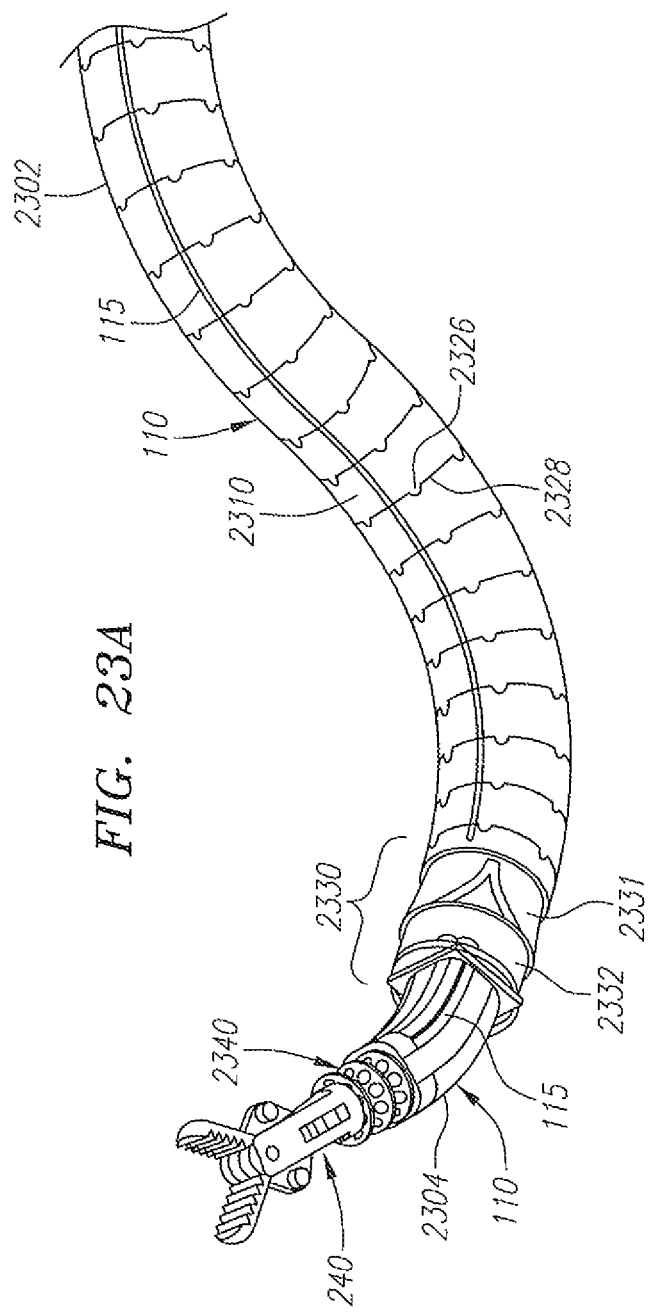

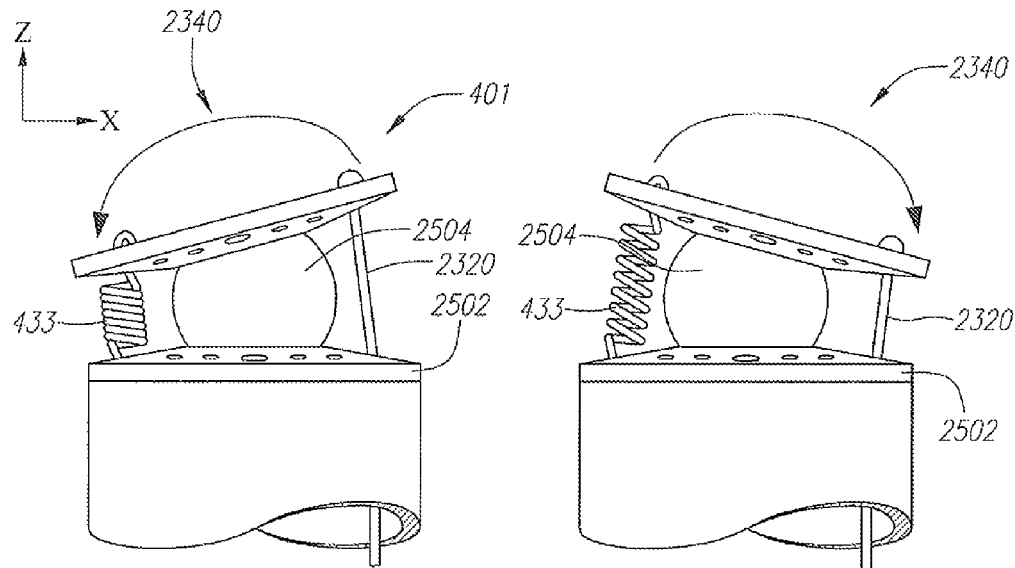
FIG. 25C
FIG. 25E
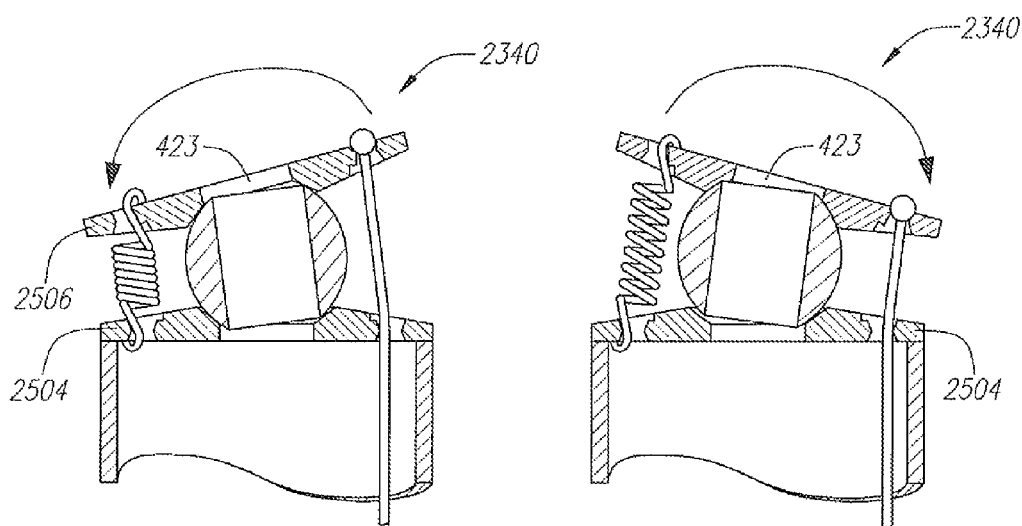
FIG. 25D
FIG. 25F

Forward Kinematics:

Inverse Kinematics:

OPTICAL FIBER GRATING SENSORS AND METHODS OF MANUFACTURE

CROSS-REFERENCE TO RELATED APPLICATIONS

The present application claims the benefit under 35 U.S.C. §119 to U.S. Provisional Application No. 61/003,008, entitled "System and Method for High Density Multiplexing of Optical Fiber Grate Sensors," filed on Nov. 13, 2007, the contents of which are incorporated herein by reference as though set forth in full.

The present application may also be related to subject matter disclosed in the following applications, the contents of which are also incorporated herein by reference as though set forth in full: U.S. patent application Ser. No. 11/678,001, filed Feb. 22, 2007; U.S. patent application Ser. No. 11/678,016, filed Feb. 22, 2007; U.S. patent application Ser. No. 11/690,116, filed Mar. 22, 2007; and U.S. application Ser. No. 12/192,033, filed on Aug. 14, 2008; U.S. Provisional Patent Application No. 60/776,065, filed Feb. 22, 2006; U.S. Provisional Patent Application No. 60/785,001, filed Mar. 22, 2006; U.S. Provisional Patent Application No. 60/788,176, filed Mar. 31, 2006; U.S. Provisional Patent Application No. 60/925,449, filed Apr. 20, 2007, and U.S. Provisional Patent Application No. 60/925,472, filed Apr. 20, 2007; and U.S. Provisional Patent Application No. 60/964,773, filed on Aug. 14, 2007.

FIELD OF INVENTION

The inventions relate generally to optical fiber sensors such as optical fiber sensors that are used in robotically controlled systems. Embodiments of the inventions may be particularly useful in robotically controlled minimally invasive surgical systems.

BACKGROUND

Optical sensors such as optical fiber sensors have been used in various applications including communications, optics, civil engineering and structural analysis and monitoring, and seismology. For example, it is known to use optical fiber sensors as filters in optical communications systems and as optical multiplexers and demultiplexers. Optical fiber sensors may also be utilized as strain and temperature sensing elements. These types of sensors may also be utilized for determining the presence of certain environmental elements.

As another example, optical fiber sensors may be utilized in robotic interventional systems and devices, which may be particularly well suited for use in performing minimally invasive medical procedures as opposed to conventional procedures that involve opening the patient's body to permit the surgeon's hands to access internal organs. Traditionally, surgery utilizing conventional procedures meant significant pain, long recovery times, lengthy work absences, and visible scarring. However, advances in technology have lead to significant changes in the field of medical surgery such that less invasive surgical procedures such as minimally invasive surgery (MIS) procedures are increasingly popular.

A "minimally invasive medical procedure" is generally considered a procedure that is performed by entering the body through the skin, a body cavity, or an anatomical opening utilizing small incisions rather than larger, more invasive open incisions in the body. Various medical procedures are considered to be minimally invasive including, for example, mitral and tricuspid valve procedures, patent formen ovale, atrial septal defect surgery, colon and rectal surgery, laparoscopic appendectomy, laparoscopic esophagectomy, laparoscopic hysterectomies, carotid angioplasty, vertebroplasty, endoscopic sinus surgery, thoracic surgery, donor nephrectomy, hypodermic injection, air-pressure injection, subdermal implants, endoscopy, percutaneous surgery, laparoscopic surgery, arthroscopic surgery, cryosurgery, microsurgery, biopsies, videoscope procedures, keyhole surgery, endovascular surgery, coronary catheterization, permanent spinal and brain electrodes, stereotactic surgery, and radioactivity-based medical imaging methods. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. Images of the body interior are transmitted to an external video monitor to allow a surgeon to analyze the images, make a diagnosis, visually identify internal features, and perform surgical procedures based on the images presented to the surgeon on the monitor.

MIS procedures may involve minor surgical procedures as well as more complex operations. Such operations may involve robotic and computer technologies, which have led to improved visual magnification, electromechanical stabilization and reduced number of incisions. The integration of robotic technologies with skills of a surgeon into surgical robotics enables surgeons to perform surgical procedures in new and more effective ways.

Although MIS techniques have advanced, limitations of certain types of medical devices still have shortcomings and can be improved. For example, during a MIS procedure, catheters (e.g., a sheath catheter, a guide catheter, an ablation catheter, etc.), endoscopes or laparoscopes may be inserted into a body cavity duct or vessel. A catheter is an elongate tube that may, for example, allow for drainage or injection of fluids or provide a path for delivery of working or surgical instruments to a surgical or treatment site. In known robotic instrument systems, however, the ability to control and manipulate system components may be limited due, in part, to a surgeon not having direct access to the target site and not being able to directly handle or control the working instrument at the target site.

More particularly, MIS diagnostic and interventional operations require the surgeon to remotely approach and address the operation or target site by using instruments that are guided, manipulated and advanced through a natural body orifice such as a blood vessel, esophagus, trachea, small intestine, large intestine, urethra, or a small incision in the body of the patient. In some situations, the surgeon may approach the target site through both a natural body orifice as well as a small incision in the body.

For example, one or more catheters and other surgical instruments used to treat cardiac arrhythmias such as atrial fibrillation, are inserted through an incision at the femoral vein near the thigh or pelvic region of the patient, which is at some distance away from the operation or target site. In this example, the operation or target site for performing cardiac ablation is in the left atrium of the heart. Catheters are guided (e.g., by a guide wire, etc.) manipulated, and advanced toward the target site by way of the femoral vein to the inferior vena cava into the right atrium through the interatrial septum to the left atrium of the heart. The catheters may be used to apply cardiac ablation therapy to the left atrium of the heart to restore normal heart function.

However, controlling one or more catheters that are advanced through naturally-occurring pathways such as blood vessels or other lumens via surgically-created wounds of minimal size, or both, can be a difficult task. Remotely controlling distal portions of one or more catheters to precisely position system components to treat tissue that may lie deep within a patient, e.g., the left atrium of the heart, can also be difficult. These difficulties are due, in part, to limited control of movement and articulation of system components, associated limitations on imaging and diagnosis of target tissue, and limited abilities and difficulties of accurately determining three-dimensional positions and orientations of system components and distal portions thereof within the patient. These limitations can complicate or limit the effectiveness of surgical procedures performed using minimally invasive robotic instrument systems.

Further, the surgeon may have limited access to information or feedback (e.g., visual, tactile, etc.) to accurately advance and navigate tools such as one or more catheters, arms, shafts, etc., and position the working portions of such tools at precise locations to perform the necessary diagnostic and/or interventional procedures on the target tissue.

Electromagnetic position sensors, available from providers such as the Biosense Webster division of Johnson & Johnson, Inc., may be utilized to measure three-dimensional positions of components. While such sensors may be useful to some degree, these devices have limited utility due to, for example, hardware constraints, geometry constraints and electromagnetic radiation.

SUMMARY

In one embodiment involving surgical applications, a robotic system includes optical fibers with Bragg gratings that are configured to provide real-time feedback related to its own dynamic shape, which corresponds to, or is related to, a shape of a steerable elongate instrument of a telerobotic surgical system. In this manner, shapes and/or positions of the steerable elongate instrument can be dynamically determined using optical fibers that include Bragg gratings.

In another embodiment involving surgical applications, an optical fiber grating sensing system may be configured and coupled to elongate surgical instruments, such as extension tools, for determining and monitoring the shapes and/or positions of the various portions or segments of such instruments. The optical grating sensing system may provide information or feedback to the surgeon to accurately navigate extension tools and place the working portions of the extension tools at the target site for performing diagnostic and/or interventional procedures on the target tissue.

Embodiments of the invention provide novel and unique approaches to high density multiplexing of fiber grating sensors by combining amplitude and wavelength division multiplexing. High density multiplexing may, for example, be utilized in telerobotic surgical systems to provide high resolution bend sensing of surgical system components. Embodiments may also be used in other systems for use in other bend sensing applications.

A further embodiment is directed to a method of manufacturing an optical fiber sensor such as a Bragg fiber grating sensor system, which may, for example, be utilized in telerobotic surgical systems. The Bragg fiber grating sensor system comprises a plurality of optical fibers that may be single mode fibers having a single core. The method comprises assembling the optical fibers into a configuration such that they are aligned substantially parallel to one another, and writing Bragg fiber gratings into the respective fiber cores of the fibers at the same time. Gratings may be written at nearly same axial position.

According to a further embodiment involving surgical applications, an amplitude and spectral shape Bragg fiber grating sensor optical fiber, which may be utilized in a telerobotic surgical system, comprises a fiber core having an array of axially spaced Bragg fiber gratings. The gratings can be written with a substantially equal index of refraction variation and unequal lengths.

Another embodiment is directed to a Bragg grating sensor optical fiber that utilizes amplitude and spectral shape multiplexing and may be used in a telerobotic surgical system and other systems and applications. The optical fiber comprises a plurality of axially spaced arrays of Bragg gratings that are provided on a fiber core. Each array may include axially spaced gratings written on the optical fiber core with a substantially equal index of refraction variation and unequal lengths.

In accordance with a further alternative embodiment that may be used in surgical and other applications, a Bragg grating sensor optical fiber comprises an array of axially spaced Bragg gratings written on a single optical fiber core with non-uniform spacing between refractive index periods that are unique to each grating resulting in unique characteristic sidelobe spectrums tagging the respective gratings.

According to yet another embodiment that may be used in surgical and other applications, a Bragg grating sensor system comprises a plurality of single core optical fibers that are assembled into a fiber sensor configuration in which the respective fiber cores are aligned substantially parallel to one another. Each fiber core has written thereon one or more Bragg grating arrays.

In a further embodiment involving surgical applications, a system comprises an elongate catheter instrument and a Bragg grating sensor optical fiber. The elongate catheter instrument has a distal portion and a proximal portion that is more rigid than the distal portion. The Bragg grating sensor optical fiber is coupled to the catheter instrument and comprises at least one optical fiber core having a distribution of Bragg gratings. The number of gratings in a portion of the fiber core coupled to the stiffer, proximal portion of the catheter instrument is less than the number of gratings in a portion of the fiber core coupled to the more flexible distal portion of the catheter.

In yet another embodiment that may be used in surgical and other applications, an optical fiber including multiplexed Bragg gratings using a substantially same spectral space comprises a first grating and a second spatially displaced set of dual overlaid gratings. The first grating is written at a wavelength $\lambda_1$, and the second spatially displaced set of dual overlaid gratings written at $\lambda_1+\epsilon$ and $\lambda_1-\epsilon$. In one or more embodiments, spectral displacement $\epsilon$ is about 0.4 nm to about 3 nm, e.g. about 2 nm, and the spectrally displaced wavelengths are symmetrically displaced relative to a central wavelength $\lambda_1$.

According to another embodiment that may be used in surgical and other applications, an optical fiber comprises an optical fiber core having paired sets of wavelength division multiplexed fiber gratings thereon. In accordance with a further embodiment, an optical fiber including multiplexed Bragg gratings using a substantially same spectral space comprises a first grating, a second spatially displaced set of dual overlaid gratings, a third spatially displaced set of dual overlaid gratings and an $n^{th}$ spatially displaced set of dual overlaid gratings. The first grating is at a wavelength $\lambda_1$; the second spatially displaced set of dual overlaid gratings is at $\lambda_1+\epsilon$ and $\lambda_1-\epsilon$; the third spatially displaced set of dual overlaid gratings is at $\lambda_1+2\epsilon$ and $\lambda_1-2\epsilon$; and the $n^{th}$ spatially displaced set of dual overlaid gratings at $\lambda_1+\epsilon$ and $\lambda_1-n\epsilon$. The spectral displacement $\epsilon$ is about 0.4 nm to about 2 nm, e.g. about 1 nm, and the spectrally displaced wavelengths may be symmetrically displaced relative to a central wavelength $\lambda_1$.

According to yet another embodiment that may be used in surgical and other applications, an optical fiber including multiplexed Bragg gratings using a substantially same spectral space comprises a first grating at a wavelength $\lambda_1$; a second spatially displaced set of dual overlaid gratings at $\lambda_1+\alpha_1$ and $\lambda_1-\beta_1$, where $\alpha_1$ is not equal to $\beta_1$; a third spatially displaced set of dual overlaid gratings at $\lambda_1+\alpha_2$ and $\lambda_1-\beta_2$, where $\alpha_2$ is not equal to $\beta_2$, and an nth spatially displaced set of dual overlaid gratings at $\lambda_1+\alpha_n$ and $\lambda_1-\beta_n$, where $\alpha_n$ is not equal to $\beta_n$. In this manner, spectrally distributed wavelengths may be asymmetrically displaced relative to a central wavelength $\lambda_1$.

In an additional embodiment that may be used in surgical and other applications, an optical fiber including multiplexed Bragg gratings using a substantially same spectral space comprises a first grating at a wavelength $\lambda_1$; a second spatially displaced set of dual overlaid gratings at $\lambda_1+\alpha_1$ and $\lambda_1-\beta_1$, where $\alpha_1$ is not equal to $\beta_1$; a third spatially displaced set of three overlaid gratings at $\lambda_1+\alpha_2$, $\lambda_1-\lambda_2$ and $\lambda_1-\omega_2$, where $\alpha_2$, $\beta_2$, and $\omega_2$ are not equal, and an $n^{th}$ spatially displaced set of n overlaid gratings $\lambda_1+\alpha_n$, $\lambda_1-\beta_n$, $\lambda_1-\omega_n \ldots \lambda_1-\zeta_n$, where the spectral displacements of the overlaid gratings from $\lambda_1$ are not equal.

In one or more embodiments, a single interference pattern is used to write the respective Bragg gratings, and a sensor system or plurality of optical fibers may include three optical fibers having a triangular geometry. Respective Bragg gratings can be written on each of the fibers simultaneously. The three fibers are small diameter fibers, e.g., a diameter less than about 100 microns, e.g., about 40 to about 70 microns, and sufficient lengths, e.g. about 1.5 m to about 2.0 m, or longer as necessary. Such lengths are suitable for supporting bending measurements. Further, these small diameters decrease the spectral dynamic range associated with a tightly bent optical fiber.

In one or more embodiments, fibers are maintained in a configuration, e.g. three fibers are maintained in a triangular configuration, by mechanically securing together respective ends of the fibers in a holding fixture, or by bonding the fibers together, e.g., by heat fusing edges of the fibers together. This configuration advantageously facilitates simultaneous writing of gratings and transfer of strain between fibers during bending.

In one or more embodiments, Bragg gratings are written into cores of respective fiber cores at a same and at nearly same axial position, and this is repeated at axially spaced apart locations along a grating region of the optical fiber configuration. A hard coating material may be applied over the grating region to facilitate transfer of strain between fibers during subsequent bending. For example, the coating material, such as a polymide or glass frit coating, may be applied to the optical fiber configuration prior to when the Bragg gratings are written, or after the gratings are written. Further, respective ends of the fibers of the configuration may be mechanically constrained or clamped together prior to writing the Bragg gratings and/or applying the coating material. Fibers can also be pre-strained by clamps or prior to bonding with the hard coating. Moreover, Bragg gratings that are axially spaced apart may be written at a same or substantially same wavelength with low reflectivity, and may be written at differing wavelengths such that the Bragg sensor system can be used with a wavelength division multiplexing output or read out unit or system.

In one or more embodiments, fibers at a first end of an optical fiber configuration can be separated after the respective Bragg gratings are written and the coating has been applied. Connectors configured for serving as an interface between a fiber grating read out or output unit and ends of fibers that may be separated to facilitate connection or coupling to the connectors. Separated ends of the fibers can be fusion spliced to respective larger diameter fibers that in turn are secured to the respective grating output unit connectors. Optical fibers of the configuration have a relative small diameter in order to decrease the spectral dynamic range associated with a tightly bent optical fiber.

In one or more embodiments, optical fibers of a Bragg sensor system are single mode optical fibers. A center to center distance between adjacent gratings of the array can be maintained substantially uniform by sequencing the gratings of the array so that gratings having relatively short lengths are located adjacent to gratings having relatively long lengths. An optical fiber may also include a first grating array corresponding to a first wavelength, and a second grating array corresponding to a second wavelength and axially spaced from the first grating array. The first and second grating arrays have an identical number of individual Bragg gratings and corresponding gratings of the respective first and second grating arrays have substantially equal lengths. Further in one or more embodiments, a center to center distance between adjacent gratings of each array is maintained substantially uniform by sequencing the gratings of the array such that gratings having relatively short lengths are located adjacent to gratings having relatively long lengths.

In one or more embodiments, an overall spectral position of a respective Bragg grating of each array is uniquely determined by processing spectral profiles of each of the Bragg gratings to measure the overall amplitude of the respective gratings operating over a common spectral region. Sidelobe structures of the respective gratings, which may have differing amplitudes, e.g., ranging from about 0.1 nm to about 5 nm, and may have differing numbers of peaks, e.g., about 1 to 5 or more peaks.

In one or more embodiments, a plurality of optical fibers comprising three optical fibers are bonded together in a triangular configuration. The fibers in this geometry have lengths that are suitable to support bending measurements. Such optical fibers may have a relative small diameter, e.g., about 40 to about 100 microns. Such diameters advantageously decrease the spectral dynamic range associated with a tightly bent optical fiber. A hard coating may be applied over a grating region of the bonded optical fibers to facilitate transfer of strain between fibers during subsequent bending.

Ends of the optical fibers can be separated from one another extending from an end of the coated grated region such that separated fiber ends are coupled to respective coupling connectors configured for interfacing with a grating output unit or fusion spliced to respective larger diameter fibers that in turn are secured to the respective coupling connectors.

One or more embodiments include a multi-port tunable light source system having at least three ports configured for coupling to the respective coupling connectors. The tunable light source may also include an array of Bragg gratings on a fourth port to measure temperature. Bragg grating arrays may comprise respective multiplexed Bragg grating arrays on the respective fiber cores of the fiber sensor configuration. The tunable light source system may include respective beamsplitter and detector assemblies that are used to read out the respective multiplexed grating arrays.

One or more embodiments may also include a spectrally broadband light source including a dispersive output unit, which may include one or more bulk gratings and a detector array, is coupled to the bonded optical fibers via the respective grating output unit connectors. One or more embodiments may comprise a plurality of single core optical fibers assembled in a configuration in which the respective fiber cores are aligned substantially parallel to one another, and each fiber core has written thereon respective multiplexed Bragg grating arrays, which may be supported by each of amplitude, spectrum and wavelength measurements.

In one or more embodiments, wavelength division multiplexed Bragg gratings are multiplexed using amplitude and spectral shape.

Various embodiments may be utilized in surgical applications, e.g., telerobotic surgical applications, and with other systems and in other applications other than surgical applications.

BRIEF DESCRIPTION OF THE DRAWINGS

The foregoing and further embodiments are now described with reference to the following detailed description to be read in conjunction with the accompanying drawings, wherein:

FIGS. 21A-D illustrate embodiments including overlaid fiber gratings for use in surgical and other applications, wherein FIGS. 21A-B illustrate embodiments involving overlaid fiber gratings having a length of 2 mm that are written at different wavelengths, and a 4 mm fiber grating that is written at a third wavelength; and FIGS. 21C-D illustrate embodiments involving overlaid fiber gratings having a length of 4 mm that are written at different wavelengths, and a 2 mm fiber grating written at a third wavelength;

FIGS. 22A-C are provided for reference and illustrate a robotic instrument or surgical system in which embodiments of optical fiber sensors may be implemented, wherein FIG. 22A illustrates a robotic medical instrument system, FIG. 22B is a rear perspective view of a flexible catheter assembly of a robotic instrument system with which embodiments may be utilized, and FIG. 22C illustrates an instrument driver to which the flexible catheter assembly may be attached and to which an optical fiber sensor may be coupled;

FIGS. 23A-C illustrate different views of a multi-element sheath catheter having an optical fiber sensor coupled thereto according to one embodiment;

FIGS. 25A-F illustrate different views of an orientation platform for a working instrument with which rotational apparatus embodiments as shown in FIGS. 24A-D can be utilized;

FIGS. 26A-B are provided for reference to illustrate other configurations of a robotic instrument system in which embodiments may be utilized, wherein FIG. 26A illustrates an embodiment including three multi-segment sheath catheters having an optical fiber sensor coupled thereto, and FIG. 26B shows the configuration shown in FIG. 26A with an additional optical fiber sensor coupled to an image capture device positioned with in the master sheath;

Figure 1:
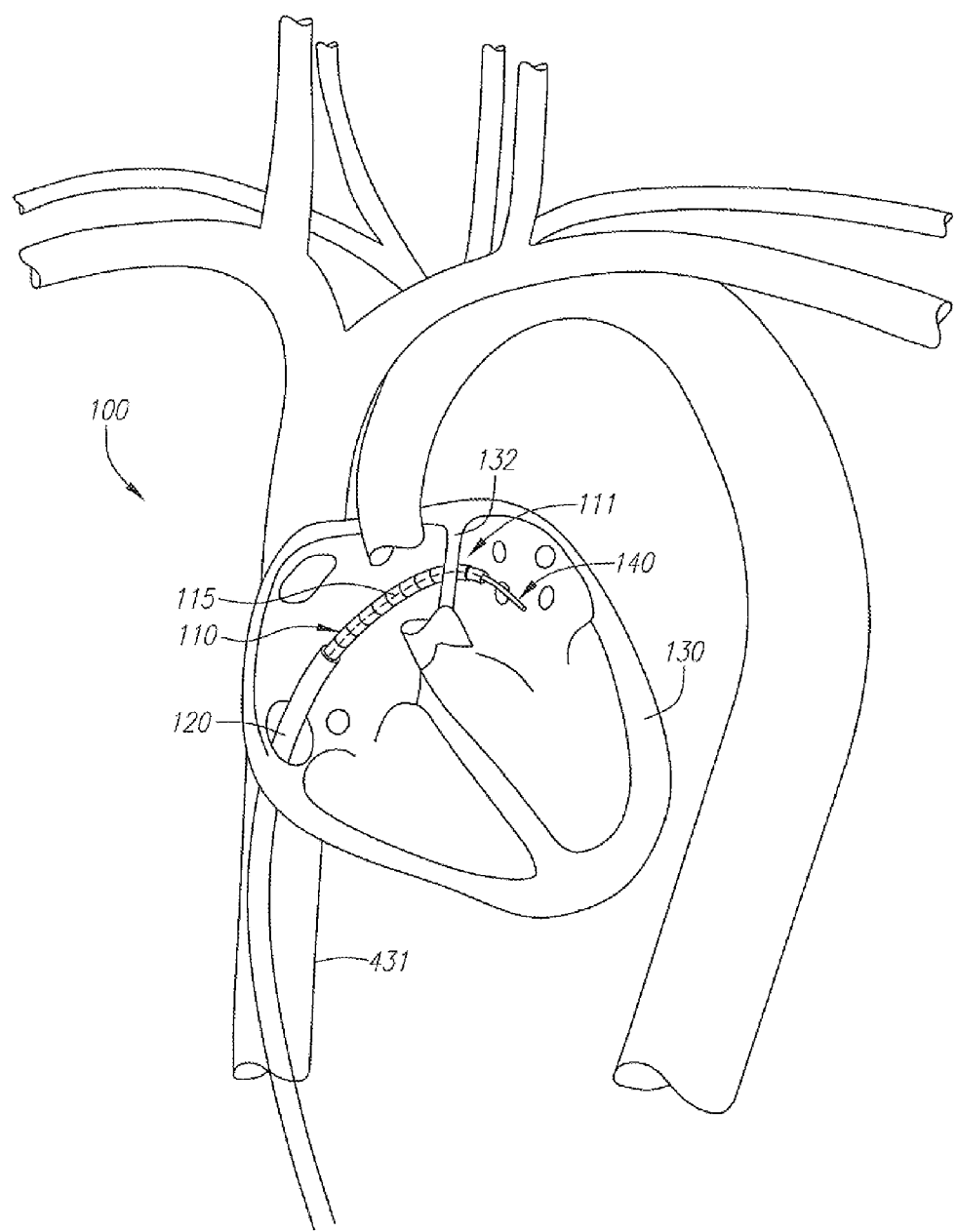
FIG. 1 illustrates an example of a robotic apparatus that may include or be utilized with embodiments of optical fiber sensor; in this particular embodiment, the robot is configured for minimally invasive surgical procedures.

As used in this specification with reference to the above figures, and in the appended claims, the singular forms "a," "an" and "the" include plural referents unless the context clearly dictates otherwise. Thus, for example, the term "a member" is intended to mean a single member or a combination of members, "a fluid" is intended to mean one or more fluids, or a mixture thereof.

DETAILED DESCRIPTION OF THE ILLUSTRATED EMBODIMENTS

Embodiments of the invention are related to optical fiber sensors, e.g., Fiber-Bragg sensors, which may be utilized in various applications. In one variation, the optical fiber sensors are implemented in applications requiring position determination, displacement detection, and/or location identification of an object or component. For example, the optical fiber sensors disclosed herein may be implemented in various robotic systems to determine the position of an robotic arm. In particular, robotic surgical systems that require precision control may benefit from having one or more integrated optical fiber sensors. In another variation, the optical fiber sensors are implemented to detect the amount of force, pressure, and/or torque being applied by a robotic arm. In yet another variation, the optical fiber sensors are implemented to detect rotation and/or twisting of the components within a robotic arm.

In certain embodiments involving robotic surgical applications, optical fiber grating sensing systems may include a plurality of fibers that are coupled to or integral with an elongate instrument, such as an extension tool or catheter. Such devices are configured to determine and monitor shapes and/or positions of various portions or segments of elongate instruments. Such sensing systems advantageously provide information or feedback to the surgeon to allow the surgeon to accurately navigate and maneuver extension tools through vasculature and position the working portions thereof at the target site for performing diagnostic and/or interventional procedures on the target tissue.

Embodiments provide fiber grating bend sensing systems and components thereof that may be used with various multiplexing methods, e.g., with amplitude, wavelength and/or spectral profile multiplexing for use in surgical and other applications. Embodiments allow for implementation of high density fiber grating sensors and may be used with commercially available output or read out units. Further, embodiments provide for efficient writing a high density array of fiber gratings that are distinct in terms of their amplitude and spectral profile while using uniform intensity writing processes, thereby minimizing fabrication costs. Additionally, with embodiments, optical fibers are arranged into bend sensitive configurations (that may be triangular for tri-fiber sensors) such that the fibers are substantially parallel to each other in order to allow fiber gratings to be written simultaneously into multiple fiber cores, e.g., at the same or approximately the same axial position. The fibers may also be coated to improve bend sensitivity.

Aspects of various embodiments and components that may be used in non-surgical and surgical applications such as robotic surgical applications are described with reference to FIGS. 1-21D. One manner in which embodiments may be implemented in robotic surgical applications is described with reference to FIGS. 22A-49. Thus, it should be understood that while certain embodiments are described in the context of surgical procedures and related devices, e.g., robotically controlled minimally invasive surgical systems, embodiments may be used in other applications for different purposes. Accordingly, it should also be understood that descriptions of how embodiments may be utilized in surgical systems and applications are provided as non-limiting examples of how embodiments may be implemented.

Figure 2:
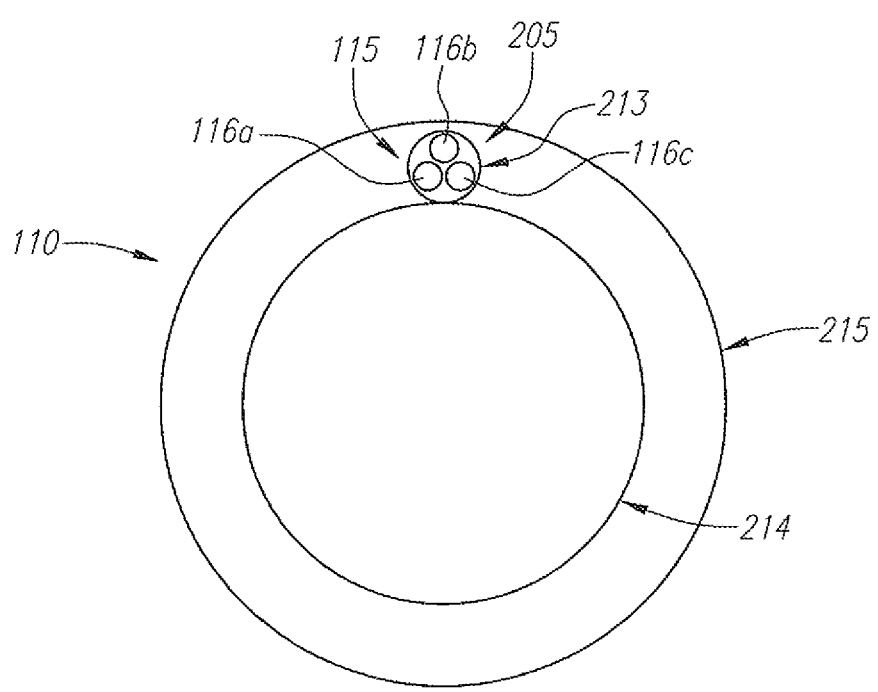
FIG. 2 is a cross-sectional view of an embodiment involving surgical applications and a catheter or elongate instrument that defines an aperture configured to receive an optical fiber sensor constructed according to one embodiment.

Referring to FIGS. 1-2, according to one embodiment, one or more components of a robotically controlled instrument 100 of a robotic surgical system include one or more optical fiber sensors 115 (generally referred to as a fiber sensor 115). According to one embodiment, a fiber sensor 115 is operably coupled to, or an integral part of, an elongate instrument body 110. According to another embodiment, the fiber sensor 115 includes a plurality of fibers 116, which may be single mode fibers. As illustrated in further detail in FIG. 2, a fiber sensor 115 constructed according to one embodiment includes three fibers 116a-c (generally referred to as fibers 116). The fibers 116a-c may be grouped, coupled or mechanically secured together, e.g., in a triangular configuration or package 205 as shown in FIG. 2.

Fiber sensors 115 that include multiple individual fibers 116 may be advantageous relative to a single fiber device that includes multiple cores since end portions of individual fibers of embodiments can be separated or spread out. This facilitates attachment or coupling of the ends of the fibers 116 to connectors, which may be used to interface to one or more fiber grating output units or other optical components such as another fiber. Such capabilities may be much more difficult to implement with a multi-core fiber.

While FIG. 2 generally illustrates a tri-fiber sensor 115, it should be understood that the fiber sensor 115 may include other numbers and arrangements of fibers 116, e.g., two, four, five and other numbers of fibers 116. Some or all of the fibers 116 may be grouped, coupled or mechanically secured together. Thus, FIGS. 1-2 are provided to illustrate one manner in which embodiments may be implemented.

Referring again to FIG. 1, according to one embodiment involving surgical procedures, optical fiber sensors 115 are configured for use with an elongate instrument body 110 in the form of a catheter, one example of which is a guide catheter. In the illustrated embodiment, the elongate body or catheter 110 is a part of a robotically controlled instrument 100 that it utilized to position a bendable distal end portion 111 of the catheter 110 and one or more working instruments 140 at a target site within a patient. The particular working instrument 140 employed may depend on the target tissue and manner in which the instrument 100 is inserted or advanced into the patient.

More particularly, in one embodiment, an optical fiber sensor 115 is configured for insertion into, attachment to, or to be an integral part of, an elongate instrument or catheter 110. This may be accomplished in various ways. In one embodiment, as shown in FIG. 2, three fibers 116a-c are positioned within a lumen 213 that is defined through a wall of the catheter 110, i.e., through a lumen 213 defined between an inner wall 214 and an outer wall 215 of the catheter 110. In other embodiments, one or more fibers 116 are coupled, bonded or attached to the inner wall 214 of the catheter 110, or coupled, bonded or attached to the outer wall 215 as appropriate. In further embodiments, an aperture or groove is formed within the inner wall 214 or within the outer wall 215, and one or more fibers 116 are positioned within the groove. Further, one or more optical fibers 116 can be coupled to a catheter or other instrument 110 in such a manner that a portion of the optical fiber 116 is coupled at a known reference location on the proximal potion of the instrument 110 for purposes of providing a point of reference, which may be useful during positioning and navigation of the instrument 110.

FIG. 2 illustrates a catheter 110 wall that defines a single lumen 213 to accommodate an optical fiber sensor 115 that includes three fibers 116a-c, but other embodiments may involve multiple lumens 213 that are defined within the catheter 110 wall, and one or more fibers 116 may extend through each lumen 213. For ease of explanation, reference is made generally to an optical fiber sensor 115 having three fibers 116a-c, and the fiber sensor 115 being coupled to or integral with a component or catheter 110 of a surgical robotic system 100 by being positioned within an aperture 213 defined within the catheter 110 wall.

As generally illustrated in FIG. 1, one manner in which robotic intravascular systems including an elongate instrument 110 having an optical fiber sensor 115 coupled thereto or integral therewith may be utilized is to position the catheter 110 or other working instrument 140 within the heart 130. One application of such a system is to assess, treat or ablate endocardial tissue. In the illustrated embodiment, a robotically controlled instrument 100 including a catheter or guide instrument 110 and a sheath instrument 120 is positioned within the heart 130. Although embodiments are described with reference to treatment of cardiac tissue, embodiments may also be utilized in other surgical applications. Thus, FIG. 1 is provided to illustrate one example of how embodiments may be utilized.

FIG. 1 depicts delivery of the instrument 100 utilizing a standard atrial approach in which the robotically controlled catheter 110 and sheath 120 pass through the inferior vena cava and into the right atrium. An image capture device (not illustrated in FIG. 1), such as an endoscope or intra-cardiac echo ("ICE") sonography catheter, may be advanced into the right atrium to provide a field of view upon the interatrial septum. The catheter 110 may be driven to the septum wall 132, and the septum 132 may be crossed using a conventional technique of first puncturing the fossa ovalis location with a sharpened device, such as a needle or wire, passed through a working lumen of the catheter 110. A dilator or other working instrument 140 is passed over the sharpened device, which is withdrawn, thereby leaving the dilator 140, over which the catheter 110 may be advanced. Various other working instruments 140 may be delivered through the lumen of the catheter 110 as necessary and depending on the surgical application. For example, for treatment of atrial fibrillation, the working instrument 140 may be an ablation catheter that delivers targeted radio frequency (RF) energy to selected endocardial tissue. Further aspects of such systems, devices and applications are described in U.S. application Ser. No. 11/176,598, the contents of which were previously incorporated herein by reference in its entirely for all purposes. The optical fiber sensor 115 configured for use in surgical applications can be used for various purposes. For example, the optical fiber sensor 115 may serve as a localization sensor, which may be used to "localize" or monitor the position and/or orientation of various objects or system components involved in a surgical procedure, and in other applications involving registration, calibration, force calculation and feedback, improved accuracy, mechanical interfacing or "connectorization," and fiber-based diagnostics.

Figure 3:
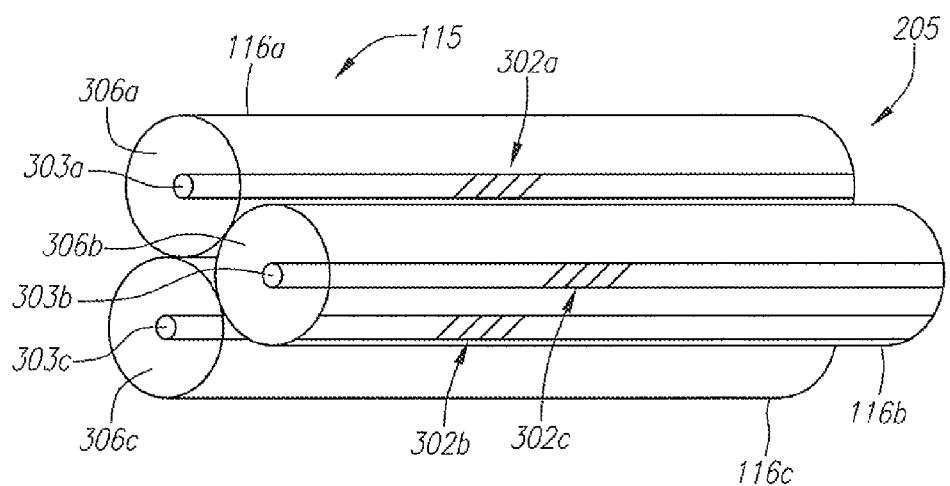
FIG. 3 illustrates an optical fiber sensor constructed according to one embodiment that includes three substantially parallel optical fibers and that may be used in surgical and other applications.

Referring to FIG. 3, for use in these and other applications, one or more distributed Bragg reflectors, such as one or more Fiber Bragg gratings (FBGs) 302a-c (generally referred to as fiber gratings 302), may be written into respective cores 303a-c (generally referred to as cores 303) of respective fibers 116a-c that are surrounded by three respective claddings 306a-c (generally referred to as claddings 306).

According to one embodiment, the fibers 116 are single mode fibers that have a diameter of less than 125 microns, e.g., about 40 to 100 microns, e.g. about 40 to about 70 microns. Embodiments may also be implemented using fibers 116 having diameters less than 40 microns. Thus, fibers 116 for use in embodiments may be smaller than fibers typically used in communications applications, but embodiments may also be implemented using standard telecommunication fibers as necessary.

Figure 14:
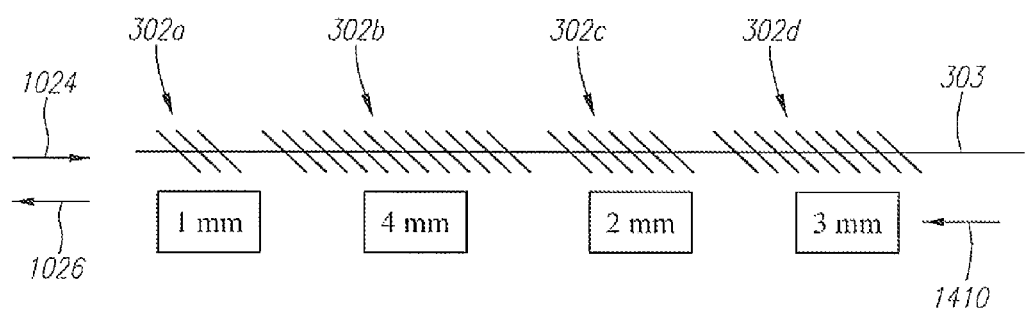
FIG. 14 illustrates an array of fiber gratings written into a fiber core such that the gratings have different lengths and may be used for amplitude and spectral profile multiplexing for use in surgical and other applications.

According to one embodiment, the fibers 116 are substantially aligned, e.g., with in a fixture, which maintains or arranges the fibers 116 in a fixed configuration. In the illustrated embodiment, three fibers 116a-c are arranged in a triangular configuration 205, and gratings 302a-c are written into precise locations, e.g., at the same or nearly the same axial position, into cores 303a-c of the respective fibers 116a-c so arranged. Gratings 302a-c may be simultaneously written into cores 303a-c, e.g., in a periodic manner, using various known methods and devices. A core 303 may include a single grating 302 (as illustrated in FIG. 3) or an array of axially spaced gratings 302 (as illustrated in FIG. 14 and other figures). Thus, embodiments advantageously allow gratings 302 to be written at the same or nearly the same time and at the same or nearly the same axially spaced locations.

Figure 4:
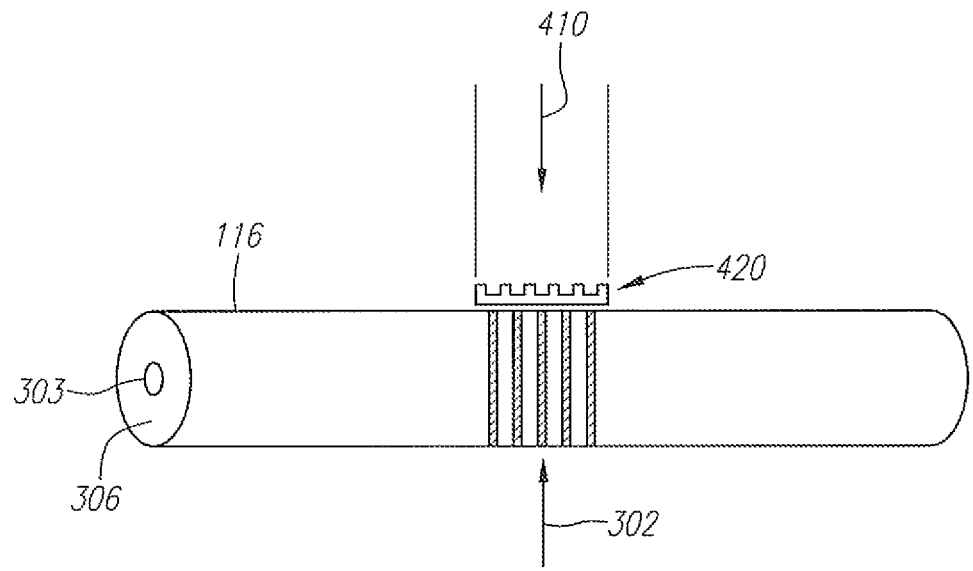
FIG. 4 illustrates one manner in which a grating can be written into a core of an optical fiber utilizing a laser beam and an optical phase mask.
Figure 5:
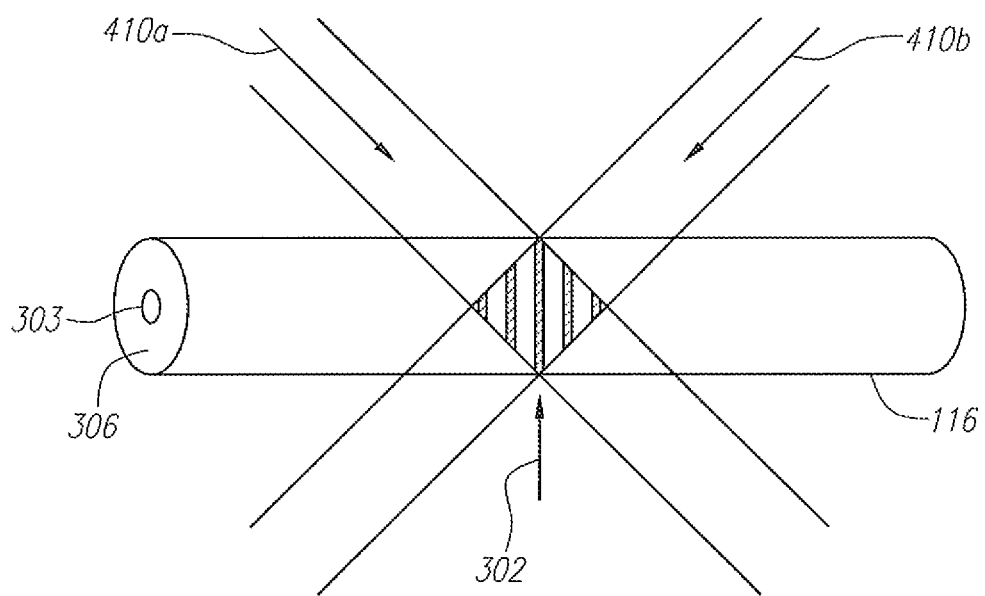
FIG. 5 illustrates another manner in which a grating can be written into a core of an optical fiber utilizing crossing or overlapping laser beams.

FIGS. 4-5 illustrate systems and methods that may be used to write one or more gratings 302 onto a core 303 of a fiber 116. Referring to FIG. 4, a fiber grating 302 may be written into a core 303 of each fiber 116 by using a short wavelength (e.g., ultraviolet) laser beam 410 and an optical phase mask 420 that has a variable thickness. This configuration generates a side imaged interference pattern. The core 303 of the optical fiber 116 is exposed to the interference pattern, thereby resulting in formation of a grating or periodic variation of the index of refraction within the core 303 that remains after the laser 410 is withdrawn. In this manner, an ultraviolet (UV) laser beam 410 may be used to "write" a grating 302 into the core 303 of a photosensitive fiber 115. In one embodiment, a single interference pattern is utilized for this purpose. Other numbers of interference patterns may be generated, e.g., with other numbers of laser beams 410 and/or other optical components as necessary in order to write multiple gratings 302 into a core 303. Different period phase mask 420 regions can also be used to generate an array of fiber Bragg gratings 520. Further, a single fiber 116 can include multiple arrays of gratings 302.

As another example, referring to FIG. 5, a fiber grating 302 may be generated in the core 303 of an optical fiber 116 by using short wavelength (e.g., ultraviolet) coherent beams 410a, 410b that are crossed or overlap. These crossing beams 410a, 410b are side imaged to generate an interference pattern, which forms a grating 302. The spacing of the grating 302 can be adjusted by changing the angle of incidence, which changes the effective reflective wavelength of the fiber grating 302. Although FIG. 5 illustrates a single interference pattern, other numbers of interference patterns may be utilized to write an array of gratings 302.

Various types and arrangements of gratings 302 may also be utilized in embodiments including, for example, uniform, chirped, tilted, superstructure, uniform positive-only, Gaussian-Apodized Index gratings 302. For ease of explanation, this specification refers generally to gratings or fiber Bragg gratings (FBGs) 302, but it should be understood that different numbers, types and arrangements or spacings of fiber gratings 302 may be simultaneously written into respective cores 303 of fibers 116. Further, the fiber gratings 302 may, for example, be written at the same wavelength with low reflectivity. The center wavelength and strain state of these fiber gratings 302 can be measured using optical frequency domain reflectivity as described in further detail in U.S. Pat. No. 5,798,521 and E. Udd, editor, *Fiber Optic Sensors: An Introduction for Engineers and Scientists*, Wiley, 1991, the contents of which are incorporated herein by reference. Alternatively, fiber gratings 302 can be written at different wavelengths and supported by various commercially available output or read out units that use wavelength division multiplexing.

While FIGS. 3-5 illustrate certain core 303 and grating 302 arrangements, embodiments may utilize multiple fibers 116, each of which includes a core 303 that includes one grating 302, each of which includes a core 303 having an array of gratings 302, or multiple fibers 116, some of which have cores 303 including a single grating 302 and others of which include cores 303 having an array of gratings 302. Further, arrays of gratings 302 may include the same or different numbers of gratings 302, and the axial spacing between gratings 302 may be consistent or variable. Further, fibers 116 having multiple gratings 302 may have the same number and arrangement or axial spacing of gratings 302, different numbers of gratings 302, and the same number but different arrangements or axial spacings of gratings 302. Thus, it should be understood that embodiments may be implemented with different numbers and arrangements of fibers 116 and gratings 302.

Figure 6:
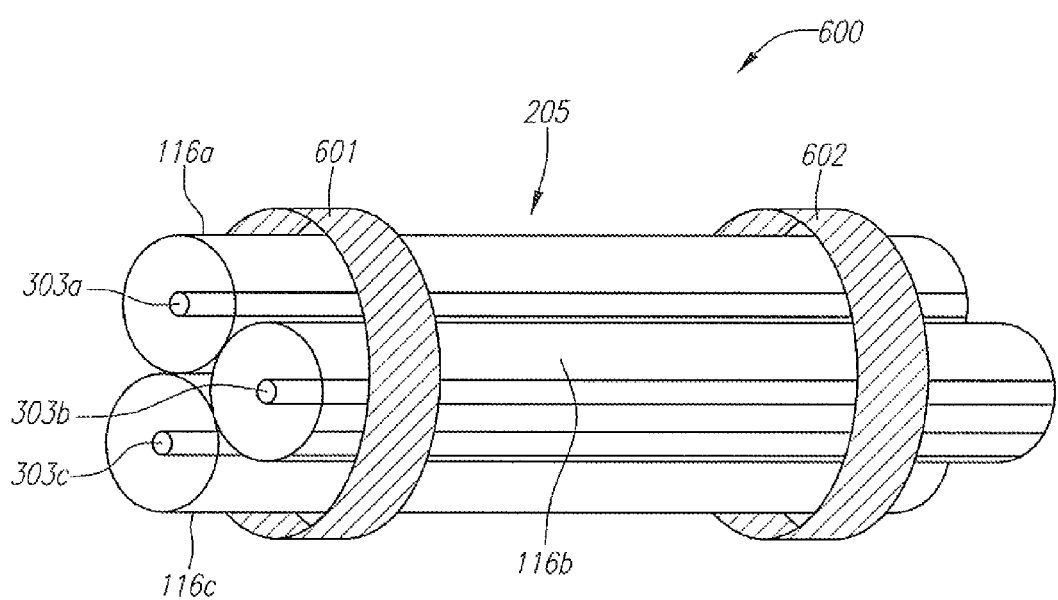
FIG. 6 illustrates three optical fibers as shown in FIG. 3 having end portions that are secured together and that may be used in surgical and other applications.

Referring to FIG. 6, according to one embodiment, multiple fibers 116 are aligned and secured within a fixture 600 such that the fibers 116 are substantially aligned. In this manner, embodiments advantageously allow gratings 302 to be written onto respective cores 303 at the same time. In the illustrated embodiment that includes three fibers 116a-c, the fixture 600 is configured to arrange and maintain the three fibers 116a-c in a triangular configuration 205. In the illustrated embodiment, the fixture 600 includes first and second connectors, which may be clamps 601, 602, and the clamps 601, 602 are secured around end portions of the fibers 116a-c. Gratings 302a-c are then written into respective aligned fibers 116a-c that are secured in the triangular configuration 205 by the clamps 601, 602.

In an alternative embodiment, fiber gratings 302 may be written into fibers 116 before fibers 116 are assembled in a triangular configuration 205. In one embodiment, three optical fibers 116a-c can be laid adjacent to each other on a flat surface, and interference patterns generated to write the fiber gratings 302a-c can be imaged across all three fibers 116a-c allowing the fiber gratings 302a-c to be fabricated during the same writing process. After the fiber gratings 302a-c are written, the fibers 116a-c can then be assembled into a triangular configuration 205.

Figure 7:
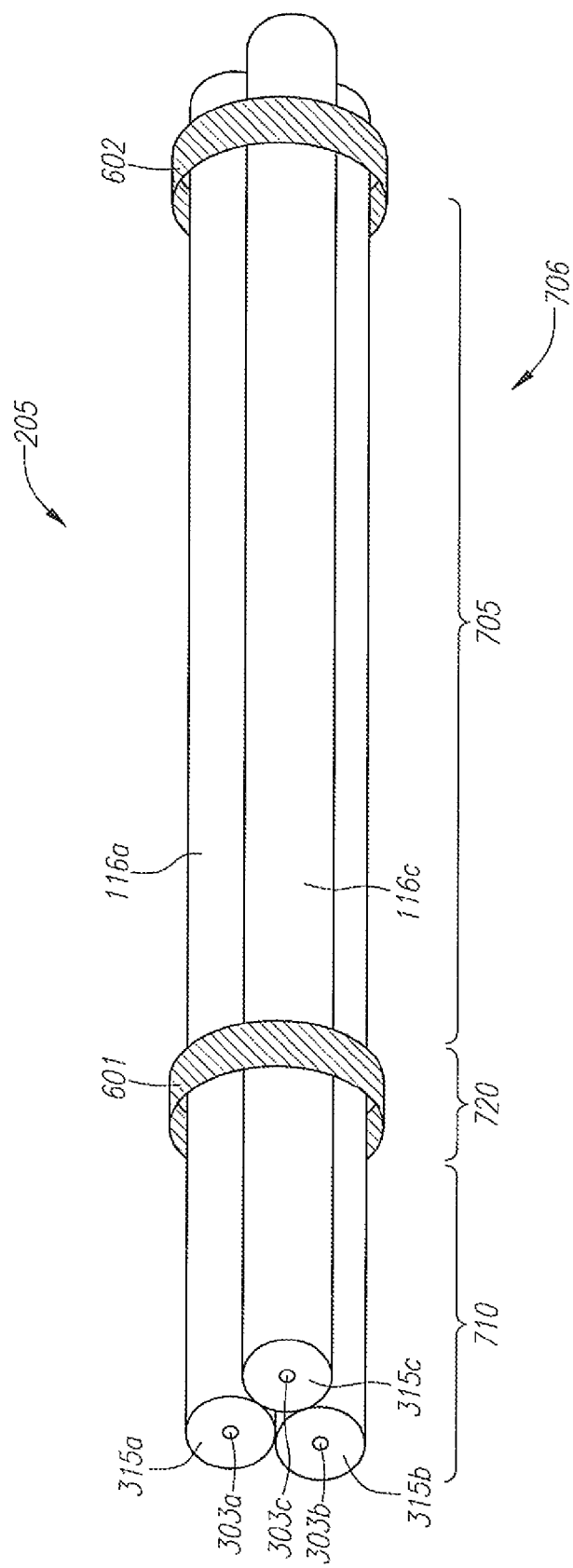
FIG. 7 further illustrates the optical fiber sensor shown in FIG. 6 and a region of secured fibers to which a coating may be applied.

Referring to FIG. 7, three fibers 116a-c can also be securely arranged within a triangular configuration 205 by application of a hard coating (not shown in FIG. 7, but generally illustrated as 706). The coating 706 may be used to hold the fibers 116 in place without clamps 601, 602. For this purpose, the coating 706 may be a polyimide or glass frit coating. In one embodiment, a coating 706 is applied over at least grating 302 sections to facilitate transfer of strain between or among fibers 116 during bending. In one embodiment, the area 705 to which the coating 706 is applied is located between clamping fixtures 601, 602. In this manner, the triangular array 205 of fibers 116 is coated and/or embedded within the coating material 706.

In one embodiment, gratings 302a-c are simultaneously written into cores 303a-c of respective fibers 116a-c of a triangular configuration 205 through the coating 706. For this purpose, the coating 706 may be a polyimide coating and have a thickness of a few microns, e.g. about 1 to about 10 microns. Other thicknesses may be utilized depending on the transmission characteristics of the coating 706 material. When the polyimide coating 706 is sufficiently thin, a small region of the coating 706 is burned off and allows sufficient transmission of ultraviolet energy such that multiple gratings 302 can be written into respective fibers 116 simultaneously. In another embodiment, a coating 706 that was previously applied to fibers 116 is stripped or removed using a suitable chemical processes before final alignment and clamping of the fibers 116 and writing of fiber gratings 302 into the fibers 116.

In another embodiment, bonding or securing of the optical fibers 116 is performed by application of sufficient heat to fuse the fibers 116 together. Glass solder technology may be used for this purpose. In these embodiments, the region 705 between clamping points 601, 602 where the fiber grating arrays 302 are written is a region in which a bonding/fusing process is performed. The clamp 601 may be removed after the glass bonding/fusing process is completed.

As shown in FIG. 7, with embodiments, ends of the fibers 116 extending from the clamp 720 can be separated, dispersed or spread out in a "break out" region 710. This capability advantageously simplifies placement of fiber optic connectors that interface with read out instrumentation.

In another embodiment, a strain relief element 720 (not illustrated in FIG. 7, but the location of which is indicated by arrow) is applied in the region of the clamp 601. The strain relief element 720 may, for example, be positioned under the clamp and above the fibers 116. The strain relief element 720 may be in the form of a tube or flexible and stable gels and is used to avoid regions of sharp bends that can result in failure or breaking of a fiber 116. For example, the strain relief 720 may be Teflon® tubing that is applied or slipped over the ends of the fibers 116 in combination with a soft stress relief material such as a commercial silicon gel supplied by Dow Corning. Strain relief may also be facilitated by removal of the clamp 601 after the coating 706 is applied over the area 705.

The break out region 710 located beyond the strain relief area 720 is preferably long enough to allow for separation of the fibers 116 to support splicing to larger fibers, which may be standard 125 micron diameter telecommunication optical fibers. For example, the break out region 710 may have a length of about 0.5 meter, and the fibers 116 may have a diameter of about 40 to about 70 microns, the ends of which may be spliced to standard 125 micron fiber.

Figure 8:
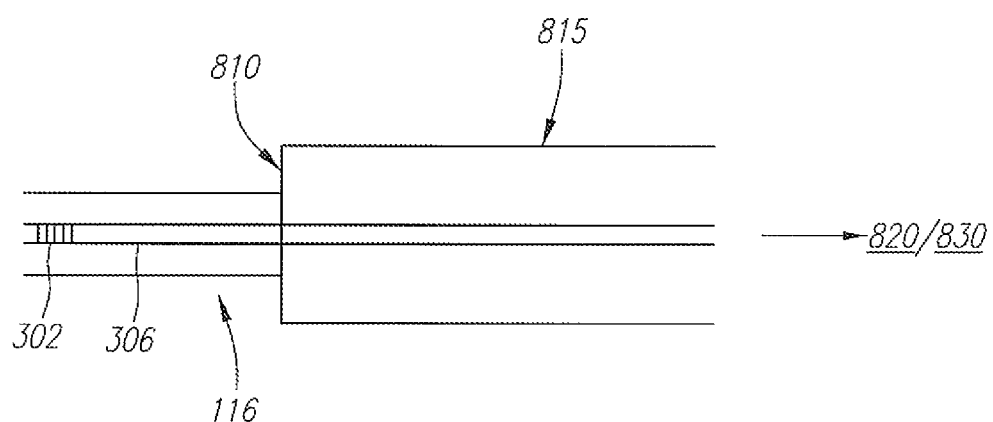
FIG. 8 illustrates one manner in which a fiber of an optical fiber sensor constructed according to one embodiment may be interfaced with or coupled to a larger diameter fiber for use in surgical and other applications.

More particularly, referring to FIG. 8, an interface region 810 is located between a small diameter optical fiber 116 into which one or more gratings 302 are written and a larger fiber 815, such as a standard 125 micron diameter fiber. The core 306 and the cladding 303 of the fiber 116 can be fusion spliced at the interface region 810 to the larger diameter fiber 815. In this manner, the break out portion 710 of fibers 116 is located beyond or outside of the coating or bond/fuse region 706 to allow for access to and manipulation of small diameter fibers 116. Suitable fusing devices that may be utilized for this purpose are available from Fujikura Composite America, Inc., 1489 Poinsettia Ave. Suite 133, Vista, Calif.; Corning, One Riverfront Plaza, Corning, N.Y.; Ericsson Telefonaktiebolaget LM Ericsson and Furukawa America, Inc., 200 Westpark Drive, Suite 190 Peachtree, Ga.

Figure 9:
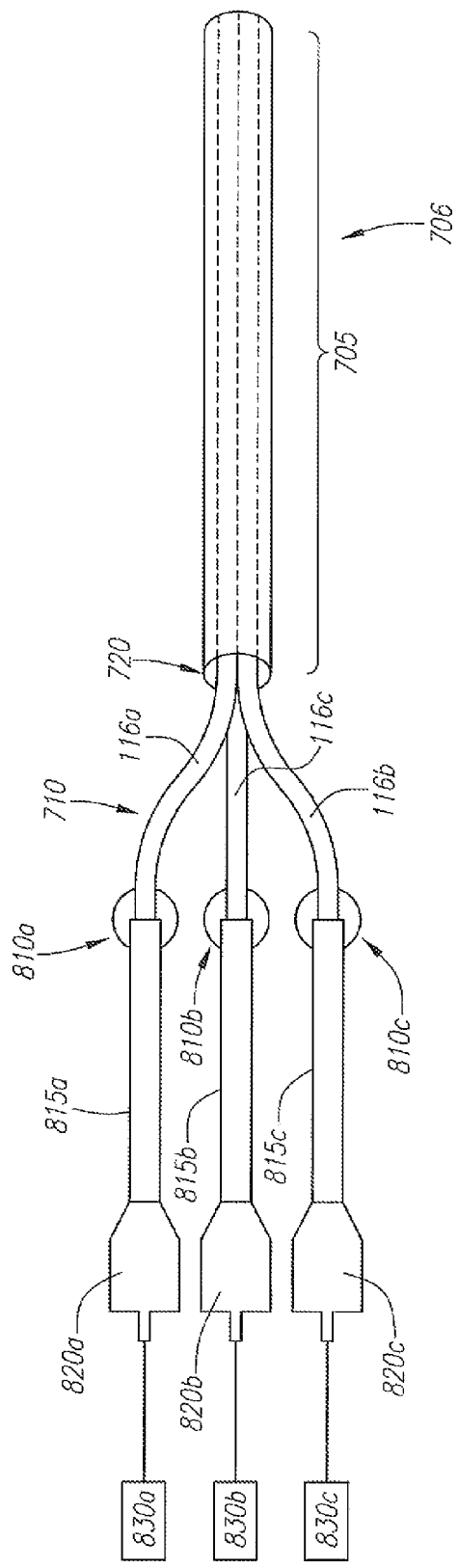
FIG. 9 illustrates components shown in FIGS. 6-8 in further detail and an output unit operably coupled to each fiber.

The standard fiber 815 to which a smaller diameter fiber 116 is fused may then be coupled to another fiber or optical component using a standard connector 820 or other device, as generally illustrated in FIG. 8, and as illustrated in further detail in FIG. 9. As shown in FIG. 9, connectors 820a-c and associated standard optical fibers 815a-c are spliced, connected or fused 810a-c to corresponding optical fibers 116 that include gratings 302. The connectors 820a-c are configured to serve as interfaces between one or more fibers 116 and one or more output or read out units 830a-c (generally referred to as output units 830). Although FIG. 8 illustrates an output unit dedicated to each connector 820/fiber 116, other output units 830 may be configured for coupling to multiple connectors 820/fibers 116. Output units 830 that may be utilized with embodiments are available from Micron Optics in Atlanta, Ga. and Ibsen Photonics of Denmark.

Figure 10:
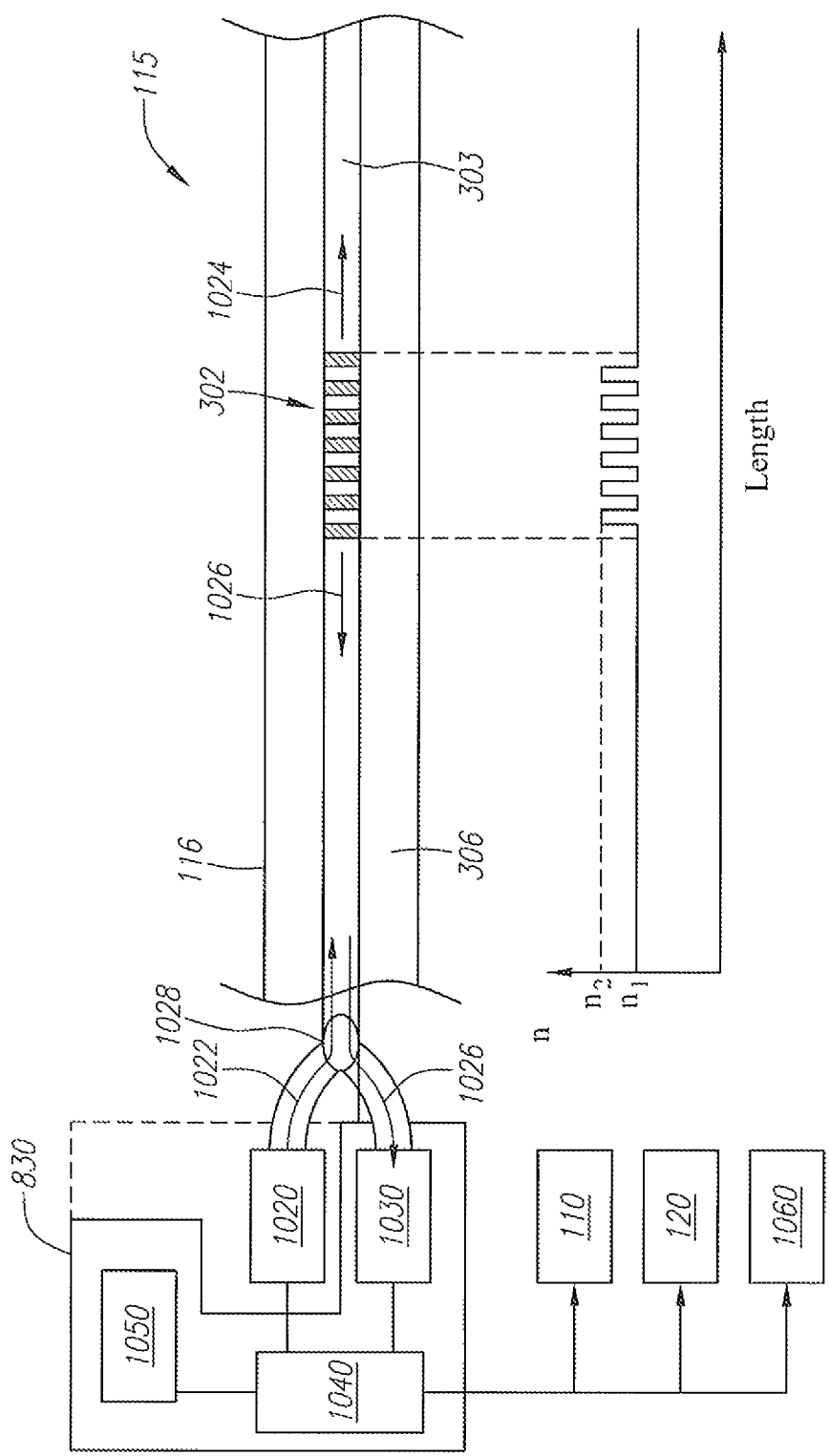
FIG. 10 schematically illustrates a system that can be utilized with an optical fiber sensor operably coupled to or associated with one or more components of a robotic surgical system or operably coupled to or associated with one or more components of another system for use in non-surgical applications.

FIG. 10 generally illustrates a system in which embodiments of an optical fiber sensor 115 including multiple fibers 116 having one or more respective gratings 302 can be utilized, e.g., for applications involving localization, registration, calibration, force calculation and feedback, improved accuracy, mechanical interfacing or "connectorization" and/or fiber-based diagnostics. For this purpose, one or more fibers 116 may be operably coupled to a catheter 110, a sheath 120, and/or another component 1060 of a robotic surgical system. For example, an optical fiber sensor 115 may be coupled to an operating table, an instrument driver or a control arm of a robotic instrument system (discussed in further detail with reference to FIGS. 22A-C).

For ease of illustration, FIG. 10 illustrates a single fiber 116 having a single grating 302 and how a fiber 116 is operably coupled to or associated with other optical components and components of a robotic surgical system. However, it should be understood that the system generally illustrated in FIG. 10 may be utilized with an optical fiber 116 that includes multiple fiber gratings 302, multiple fibers 116, e.g., three fibers 116a-c, and that additional systems and associated optical components can be provided for each fiber 116 as necessary. For example, as is understood in the art, each fiber 116 may have a dedicated output unit 830, or multiple fibers 116 may share an output unit 830. Further, although FIG. 10 illustrates a separate light source 1020 and output unit 830, the light source 1020 may also be a part of the output unit 830 (represented by dotted line). Other system configurations and/or components may be utilized, examples of which are described in further detail in U.S. patent application Ser. Nos. 11/678,001, 11/678,016 and 11/690,116 and U.S. Provisional Application Nos. 60/785,001 and 60/788,176, the contents of which were previously incorporated by reference in their entirety for all purposes. Thus, FIG. 10 is provided to generally illustrate system components and how they may be implemented in a robotic surgical system, but other numbers and configurations and components may be utilized as necessary.

A light source 1020, which may be a broadband light source or a tunable laser, emits a laser beam or optical energy 1022 that is directed into a core 303 of a fiber 116 through one or more suitable interfaces, couplers, circulators, beam splitters or connectors (generally illustrated as 1028). One connector 1028 is shown for ease of illustration, but as explained above, it should be understood that the system may include multiple couplers, connectors or beam splitters for directing light or optical energy 1022 into one or multiple cores 303 of one or multiple fibers 116 as necessary.

Light or optical energy 1022 may be partially transmitted 1024 through one or more gratings 302 and partially reflected 1026. FIG. 10 illustrates one grating for ease of illustration, but a core 303 may also include a plurality of axially spaced gratings 302. Reflected light 1026 propagates in the opposite direction through the core 303, through one or more suitable interfaces, couplers or connectors 1028, and is detected by a detector element 1030. For example, when a broadband light source 1020 is utilized, the detector element 1030 may be a dispersive element such as a bulk grating in combination with a detector array. When a tunable laser 1020 is utilized, the detector element 1030 may be linked to the tunable light source 1020 and include a calibrated gas cell to monitor the absolute wavelength of the fiber grating 302.

A controller 1040, which may be implemented as hardware, software or a combination thereof, such as a processor, a micro-controller, or a computer, which is part of, or associated with, a robotic surgical system, is configured to process data received by, or derived from, reflected light 1026. In one embodiment, the controller 1040 is configured for applications involving bending, positioning and/or orientation of various robotic surgical system components, calibration and therapeutic and diagnostic procedures. Data regarding light 1026 reflected by a grating 302 may also be displayed 1050 to a user.

Figure 11:
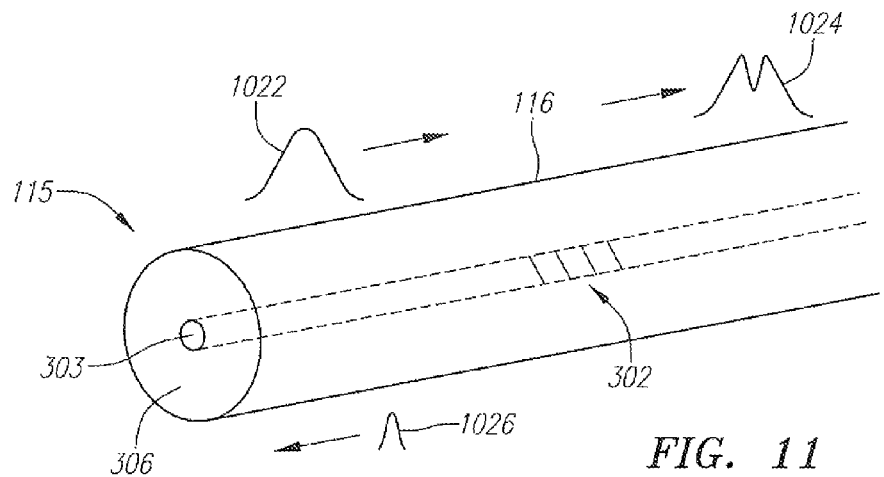
FIG. 11 illustrates transmission of optical energy through and reflection of optical energy by a grating of an optical fiber.
Figure 12A:
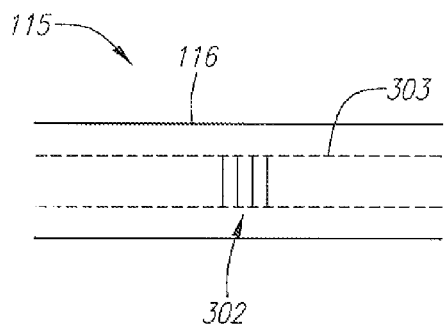
FIGS. 12A-B illustrate a fiber grating that is placed in compression as a result of forces placed upon a fiber such that a peak reflection wavelength of the reflected optical energy shifts to a shorter wavelength.
Figure 12B:
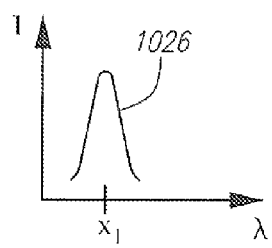

FIG. 11 illustrates in further detail how optical energy reflected 1026 by a grating 302 or an array of gratings 302 of an optical fiber 116 is processed. In the illustrated embodiment, the grating 302 is a linear FBG having a constant pitch or spacing along its length. The spectrum of the reflected light 1026 is expressed by a Bragg condition $\lambda_B = 2nx$, wherein x=grating pitch. FIGS. 12A-13B illustrate effects of different grating spacings on the reflected light 1026. As shown in FIGS. 12A-B, a grating 302 with spacing d1 results in reflected light 1026 having a peak at $\lambda 1$, and a grating 302 with spacing d2 that is greater than d1 has reflects light 1026 having a peak at $\lambda 2$ that is longer than $\lambda 1$.

FIGS. 12A-B illustrate a grating 302 spacing that may result from compression of the optical fiber 116 that results in a reduction in length of the fiber 116 which, in turn, compresses or reduces grating 302 spacing. Such compression may result, for example, when a distal end of a surgical device including a fiber sensor 115 encounters cardiac tissue. As a result, the distance between index variations of the fiber grating 302 are reduced, thereby causing the wavelength of the reflected optical energy 1026 to shift to shorter wavelength.

Figure 13A:
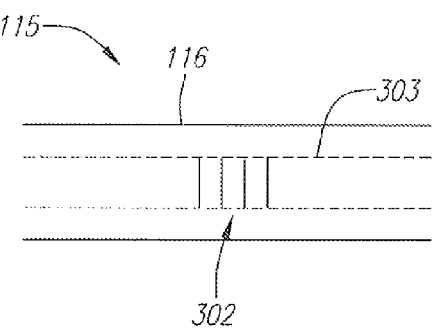
FIGS. 13A-B illustrate a fiber grating placed in tension as a result of forces placed upon a fiber such that a peak reflection wavelength of the optical energy shifts to a longer wavelength.
Figure 13B:
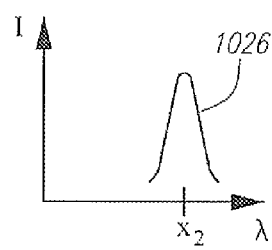

FIGS. 13A-B illustrate a grating 302 spacing that may result from tension applied to the fiber that results in a lengthening of the fiber 116 which, in turn, increases grating 302 spacing. As a result, the distance between index variations of the fiber grating 302 are increased, thereby causing the wavelength of the reflected optical energy 1026 to shift to a longer wavelength.

Certain embodiments are implemented such that the optical fiber sensor 115 includes a fiber 116 that includes an array of axially spaced fiber Bragg gratings 302 that function as a sensor 115 using amplitude and/or spectral shape multiplexing. A wavelength division multiplexing readout system 830, such as sm125 optical sensing interrogator read out unit, available from Micron Optics in Atlanta, Ga., or a unit built around the IMON 400 system available from Ibsen Photonics in Denmark, may be utilized to detect light reflected 1026 by the fiber gratings 302 at different wavelengths. In the case of the Micron Optics sm125 unit, the amplitude and spectral shape of the fiber gratings 302 are measured by a tunable laser whose absolute wavelength is calibrated using a NIST traceable gas cell. In the case of the Ibsen IMON 400, a broad band light source is used to illuminate the fiber grating and a beamsplitter directs the reflection from the fiber gratings into a pair of bulk optic gratings that spreads the spectrum across a 400 element detector array that allow accurate measurements of the amplitude and spectral shape of the reflected light signal from the fiber gratings.

Figure 15:
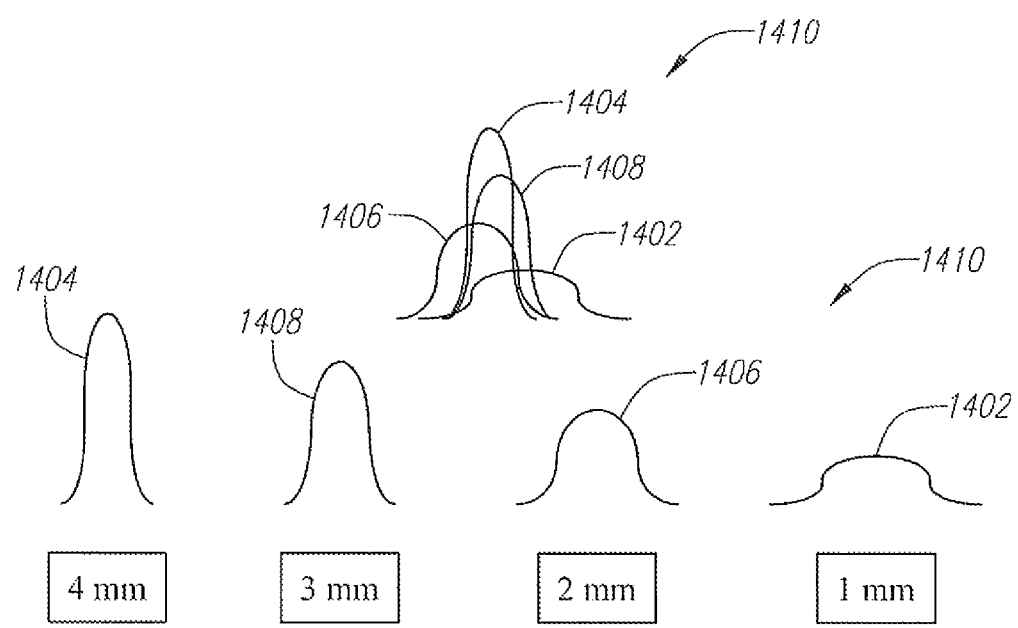
FIG. 15 further illustrates different amplitudes and spectral profiles of optical energy associated with the grating structure shown in FIG. 14.

In one embodiment, an array of fiber gratings 302 is multiplexed based on amplitude or spectral profiles of the gratings 302. FIGS. 14-15 illustrate one embodiment in which an array of four fiber gratings 302a-d is written into a core 303 of an optical fiber 116 at the same wavelength.

Gratings 302a-d that have different lengths may also have substantially the same index of refraction variation. This may result from similar exposures to UV light, e.g., as a result of exposure to UV light of the same or substantially similar intensity and the same or substantially similar periods of UV light exposure to form fiber gratings. It may also result from chemical etching processes, or ion beam milling to form fiber gratings with similar periods and reflectivity. Such gratings 302a-d can be "amplitude" multiplexed based on the amplitude of the spectral profile of reflected optical energy 1026 as determined by the respective lengths of the gratings 302a-d. In another embodiment, multiplexing can be performed based on the corresponding spectral characteristics or tags of the gratings 302a-d having different lengths.

In the illustrated embodiments, the lengths of the fiber gratings 302a-d vary and are 1 mm, 4 mm, 2 mm and 3 mm, respectively. Optical energy 1026 reflected by the fiber gratings 302a-d shown in FIG. 14 have the corresponding amplitude and spectral profiles illustrated in FIG. 15. As shown in FIGS. 14-15, fiber gratings 302 of different lengths have distinct amplitude and spectral shape attributes, and these unique attributes are used for purposes of multiplexing.

For example, during use of gratings 302a-d constructed as shown in FIGS. 14-15, a broadband light beam 1024 enters the optical fiber 116, and a beam 1026 is reflected by one or more of the fiber gratings 302a-d. If only fiber grating 302a were present in the optical fiber 303, then the optical energy 1026 reflected by this grating 302a would have a spectral profile 1402 illustrated in FIG. 15. If only fiber grating 302b were present in the optical fiber 303, then the optical energy 1026 reflected by this grating 302b would have a spectral profile 1404 illustrated in FIG. 15. Similarly, if only fiber grating 302c were present in the optical fiber 303, then the optical energy 1026 reflected by this grating 302c would have a spectral profile 1406 illustrated in FIG. 15. Further, if only fiber grating 302d were present in the optical fiber 303, then the optical energy 1026 reflected by this grating 302d would have a spectral profile 1408 illustrated in FIG. 15.

However, as shown in FIGS. 14-15, when all of the fiber gratings 302a-d are present in the optical fiber core 303, the spectrum of the reflected optical energy 1026 includes a combination of all of the individual spectral signatures shown in FIG. 15, thereby generating a unique combination spectral profile 1410 since the spectral profiles 1402, 1404, 1406, 1408 corresponding to the respective fiber gratings 302a-d are unique and do not completely overlap. By measuring the spectral profile 1410 of the reflected optical energy 1026, and knowing the spectral profiles 1402, 1404, 1406 and 1408 associated with each of the gratings 302a-d, the wavelength position of each fiber grating 302 can be de-convolved through signal processing of the profile assuming that the spectral profiles are not distorted by environmental effects. In this manner, when "amplitude" is controlled based on the length of a grating 302, and the index variation is nearly constant, then both of the amplitude and the spectral profile change and can be utilized in multiplexing applications. Embodiments so configured may be particularly useful in cases where axial strain and temperature change while other effects are isolated, thereby resulting in minimally changed spectral profiles and allowing for accurate measurements.

In certain applications that include shape sensing to support surgical operations, it is desirable to increase the density of fiber gratings 302 that can be used for axial strain measurements and to minimize fabrication costs as disposable units are typically utilized for patient safety. FIG. 14 illustrates how an array of fiber gratings 302a-d can be multiplexed in a single wavelength band with center to center spacing of the fiber gratings 302a-d of about 5 mm.

In the illustrated embodiment, a first grating 302a is written with a length of 1 mm, a second grating 302b is written with a length of 4 mm, and the spacing between gratings 302a and 302b is about 2.5 mm. A third grating 302c is written with a length of 2 mm, and the spacing between gratings 302b and 302c is about 2 mm. A fourth grating 302d is written with a length of 3 mm, and the spacing between 302c and 302d is about 2.5 mm. In general, similar sequences of fiber gratings 302 can be written in other wavelength bands in a similar manner to effectively increase the number of fiber gratings 302 that can be supported by a read out unit 830 having a fixed spectral range by a factor of four.

Figure 40:
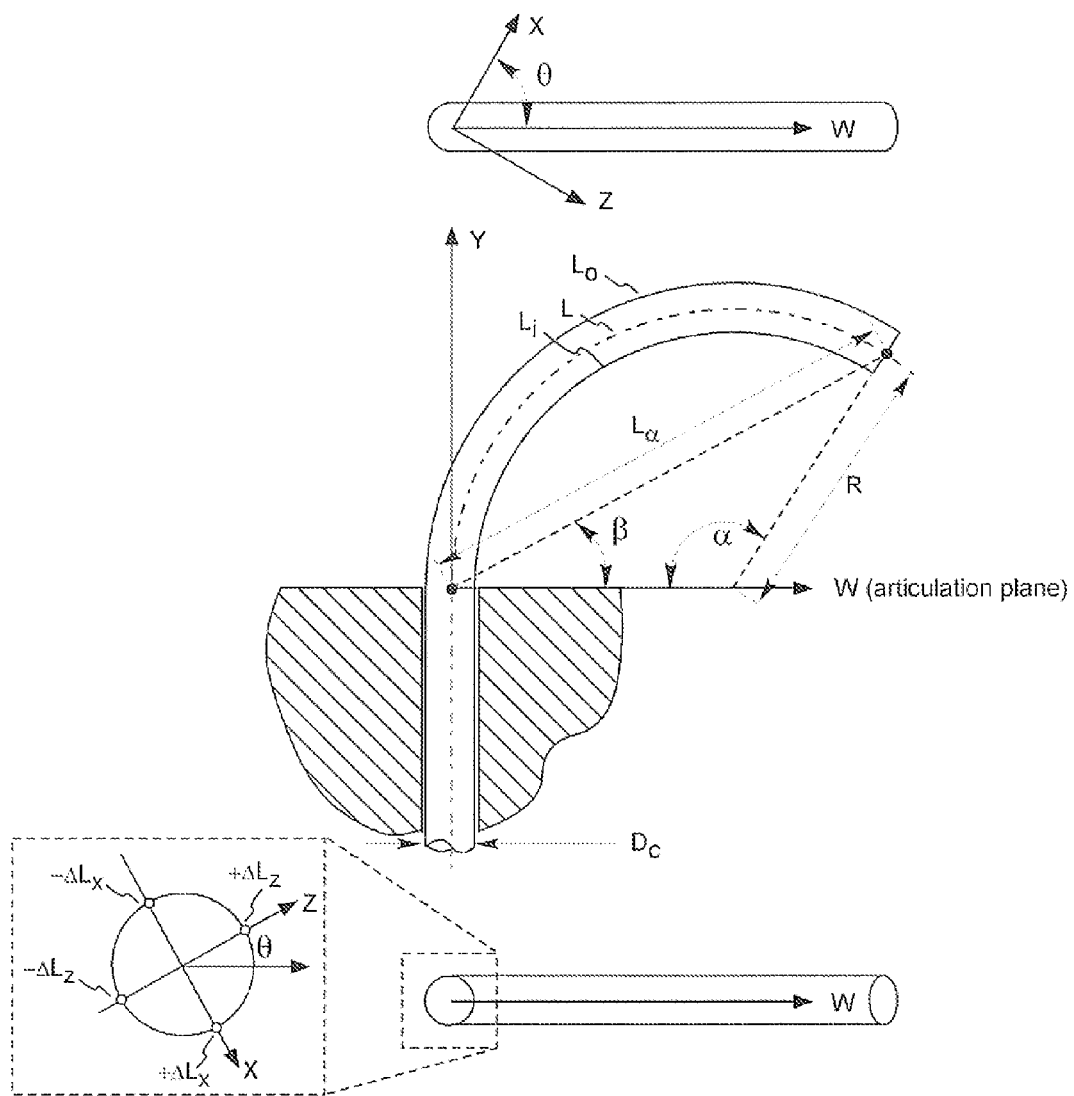
Figure 41:
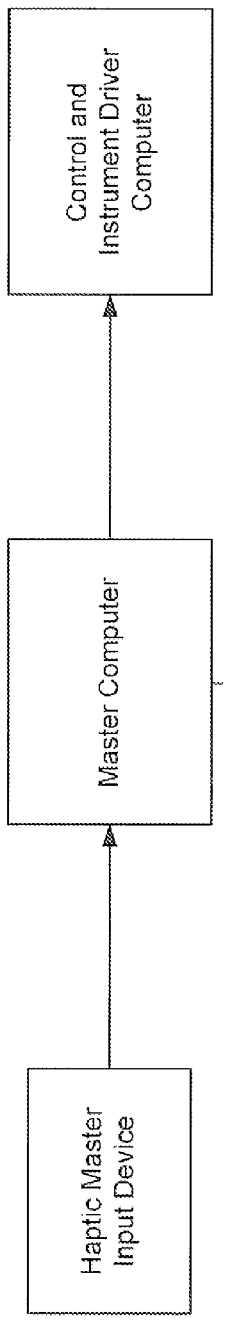

As an example, assume that the spectral range supported by a fiber grating read out system 830 is 100 nm in the 1550 nm wavelength band, and the application requires each fiber grating 302 to have an environmental strain range of 8000 microstrain for an effective wavelength range of 10 nm with a small safety wavelength band. In this example, the 100 nm fiber grating read out unit 830 can support 10 fiber gratings 302, thus requiring a 10 nm wavelength range using conventional wavelength division multiplexing. Using the amplitude and spectral profile multiplexing as shown in FIGS. 14-15, 40 fiber gratings could be supported. Thus, embodiments can be utilized to support other numbers of gratings 302 in a given wavelength band, e.g., two, three, four, five, six and other numbers of fiber gratings 302 in each wavelength band. Embodiments also advantageously provide for reduction in the requirements on the spectral range of the read out system 830.

Additionally, once the sequence of fiber gratings 302 is known in terms of spacing and length, a custom phase mask can be generated for a sequence of high density fiber gratings 302 that may be written at the same time with the same exposure intensity to minimize fabrication costs.

Other embodiments may involve a first array of fiber gratings 302 corresponding to a first wavelength, and a second array of fiber gratings 302 corresponding to a second wavelength and axially spaced from the first grating array. The first and second grating arrays may have the same number individual fiber gratings 302, and gratings 302 of the respective first and second grating arrays may have substantially equal lengths. For ease of explanation, reference is made to an array having fiber gratings 302, but it should be understood that a single fiber 116 can include a plurality of arrays of fiber gratings 302.

In another embodiment, multiplexing of reflected optical energy 1026 can be performed based on wavelength multiplexing. One embodiment involves writing axially spaced apart Bragg gratings 302 at different wavelengths such that reflected optical energy 1026 reflected by these gratings 302 can be multiplexed based on different wavelengths utilizing a wavelength division multiplexing output unit. Further, as shown in FIG. 15, as the amplitude of the grating 302 decreases, the spectral "spread" and "shape" changes. For example, if the full width half maximum of the 4 mm fiber grating is 200 nm, the 2 mm fiber grating spectral profile has a full width have maximum of 400 nm, and the 1 mm fiber grating has a full width half maximum of 800 nm. These attributes and differences or tags may be utilized for wavelength multiplexing, further aspects of which are described by E. Udd, Fiber Optic Smart Structures, Wiley, 1995, the contents of which are incorporated herein by reference.

According to another embodiment, multiplexing can be performed based on a combination of amplitude and spectral profiles as discussed above with reference to FIGS. 14 and 15. Such embodiments may be particularly useful for supporting dense packing of gratings 302 in a fiber 116. For example, this embodiment provides significant advantages by allowing for high packing density of less than 0.5 cm between fiber gratings 302 and using gratings 302 that are written with uniform exposure intensity and annealed in the same manner. This allows each fiber grating 302 in the same wavelength band to be tagged or associated with an amplitude. Further, this results each grating being associated with a spectral profile having a different shape or slope. Thus, embodiments advantageously provide a combination of two different multiplexing methods—one based on amplitude, another based on spectral profiles. These advantages provide more effective output readings when the fiber gratings 302 are nominally at the same strain values.

Another example that illustrates application of the combination of "amplitude" and wavelength division multiplexing involves supporting 40 fiber gratings over a 20 cm span on 0.5 cm centers for bend sensing applications. Thus, while use of 10 fiber gratings 302 may still be suitable (as described with reference to wavelength multiplexing above), the grating 302 density or the number of gratings 302 in a given space that can be supported can be significantly increased using a combination of amplitude and wavelength multiplexing.

As another example, consider a case in which it is desired to double the number of fiber grating strain sensor locations supported by a single spectral band defined by the strain range of the fiber grating strain sensor system. Assume that it is desired to measure 28 strain locations spaced 0.5 cm apart over a distance of 14 cm. Each of these fiber grating strain sensors 115 experiences a strain range of +/−4000 microstrain which at 1500 nm corresponds to a spectral window of about 10 nm. Using a known wavelength division multiplexed readout approach would require that the 28 fiber grating sensors 115 be supported by 280 nm of spectral width. However, as discussed above with reference to FIGS. 14-15, amplitude and spectral profile multiplexing can be utilized, and in the illustrated embodiment, fiber gratings 302 of 1, 2, 3, and 4 mm can be used to support this type of system.

According to another embodiment, multiplexing of reflected optical energy 1026 can be performed based on a combination of multiplexing based on the amplitude and spectral shape of the spectrum of reflected optical energy 1026 (as determined by grating 302 length as discussed above) as discussed above with reference to FIGS. 14 and 15, and wavelength attributes of the reflected optical energy 1026 as described above.

Figure 16:
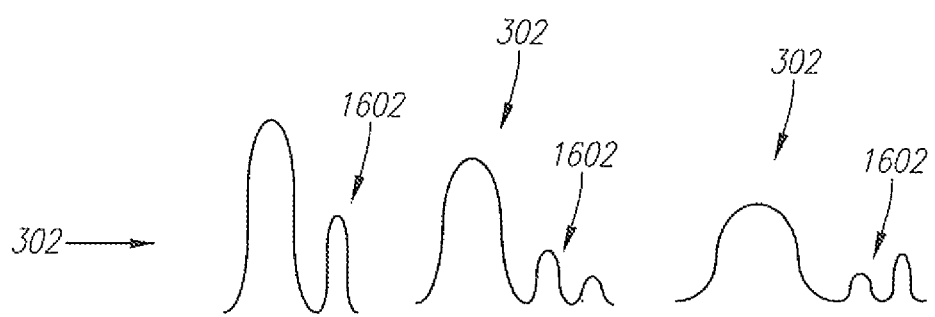
FIG. 16 illustrates writing of gratings with a non-uniform grating period to form side lobes, which may be utilized to distinguish fiber gratings that are written at similar wavelengths for use in surgical and other applications.

Referring to FIG. 16, while the spectral profiles shown in FIGS. 14-15 may be distinguished by using amplitude, wavelength and/or spectral profiles, in another embodiment, each profile is tagged based on "side lobes" 1602 in the profile that are formed by non-uniform index of refraction variations to sequential fiber gratings 302. More particularly, an optical sensor 115 may be formed of or include a grating 302 profile that is formed by intentionally introducing non-uniform index of refraction variations to sequential fiber gratings 302 such that gratings 302 can be written on a single optical fiber core with non uniform spacing between refractive index periods. These variations are unique to each grating 302 such that the spectrum of the optical energy 1026 reflected thereby has unique characteristic sidelobe spectrums 1602 elements.

The intensity/amplitude and the spectral location of a side lobe 1602 can be selected by forming these characteristics into phase masks that are used to write the fiber gratings 302. This results in formation of distinctive side lobes 1602 associated with a particular grating 302. Sidelobe structures 1602 may have various numbers of peaks, and different sidelobe structures can have different numbers of peaks and different amplitudes. Fiber grating 302 profiles that have been "tagged" with distinctive side-lobes 1602 allows for use of similar wavelengths to write fiber gratings 302. Thus, fiber gratings 302 that reflect optical energy 1026 having a spectrum that includes side lobes 1602 with their principal peaks at the same wavelength without strain can be tracked by noting the position of their side lobes 1602.

According to another embodiment, side lobe 1602 multiplexing as described with reference to FIG. 16 is used in combination with amplitude multiplexing as described above with reference to FIGS. 14-15 to provide for higher density multiplexing.

According to another embodiment, side lobe 1602 multiplexing as described with reference to FIG. 16 is used in combination with spectral profile multiplexing as described above with reference to FIGS. 14-15.

According to another embodiment, side lobe 1602 multiplexing as described with reference to FIG. 16 is used in combination with the combination of amplitude and spectral profile multiplexing as described above with reference to FIGS. 14-15.

According to another embodiment, side lobe 1602 multiplexing as described with reference to FIG. 16 is used in combination with wavelength to provide for higher density multiplexing.

According to another embodiment, side lobe 1602 multiplexing as described with reference to FIG. 16 is used in combination with wavelength multiplexing and one or more of amplitude and spectral profile multiplexing as described above with reference to FIGS. 14-15 to provide for higher density multiplexing.

According to another embodiment, multiplexing is based on spectral shaping, which involves design of unique, customized spectral profiles that can be extracted from other spectral profiles. Various unique, customized attributes can be utilized to implement embodiments, and such shaping such attributes, or spectral shaping, may be used to increase the number of fiber gratings in the same spectral band and maintain their same spatial location. Examples of spectral shaping may involve customized spectral profiles (as described above with reference to FIGS. 14-15) and customized side lobes (as described with reference to FIG. 16.

Figure 17:
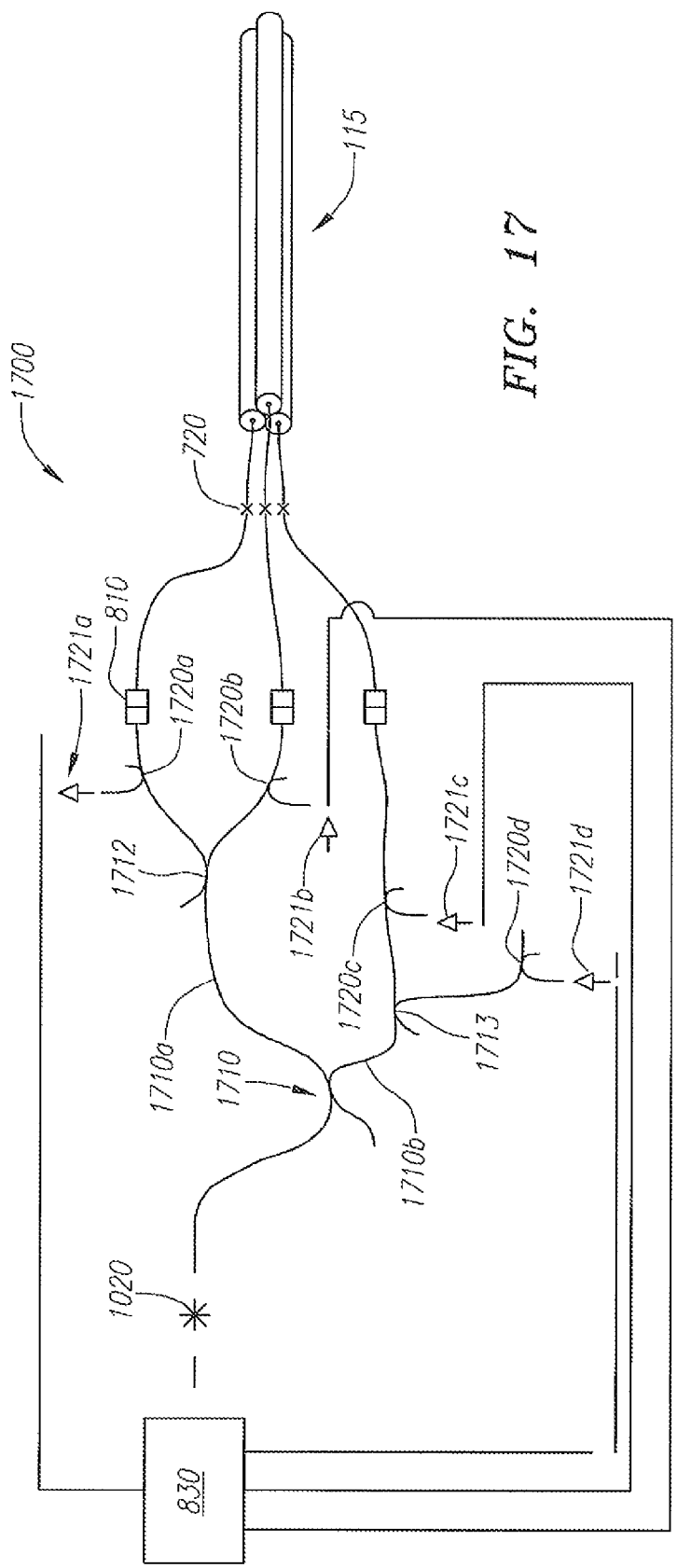
FIG. 17 schematically illustrates a fiber grating bend sensor system constructed according to one embodiment that includes a tunable light source and an array of output units or detectors configured to monitor each optical fiber containing a fiber grating sensor array.

FIG. 17 illustrates a system 1700 that may be utilized with, for example, a combination of three multiplexing methods: amplitude multiplexing, spectral profile multiplexing and wavelength division multiplexing. Embodiments advantageously allow for the realization of low cost output units. Light 1022 emitted by a tunable light source 1020 (e.g., available from Micron Optics, inc., 1852 Century Place NE, Atlanta, Ga.) is coupled into a fiber beam splitter 1710 that has outputs 1710a and 1710b that are connected to two more fiber beam splitters 1711, 1712. In this manner, up to four fiber grating array lines 1721a-d may be supported. In one embodiment, the multi-fiber sensor array 115 is a three fiber 115 arrangement that includes a hard coating 706 such as a polyimide or a fusion bond. Outputs of three fibers 115 are connected via standard fiber connectors 810 to the leads directed to the multi-fiber grating bend sensor array 115. The transition from the larger fiber 815 diameter input to the smaller fiber 115 diameter associated with the sensing region of the array is supported by fusion splices 720. The reflection 1026 from the individual fiber grating arrays 302 is obtained via an output coupler/detector combination 1720a-c associated with each of the arrays 1721a-c that is used to determine wavelength shifts of fiber gratings in the array. These measured wavelength shifts are then in turn used to measure strain and bend. Embodiments may also utilize a fourth fiber or array that is coupled at 1720d. In these embodiments, a fourth port 1721d may be utilized to measure a temperature of a fourth fiber grating array 1721d. The outputs from 1721a, 1721b, 1721c and 1721d are connected to the fiber grating readout unit 830 that also controls the tunable light source 1020.

Figure 18:
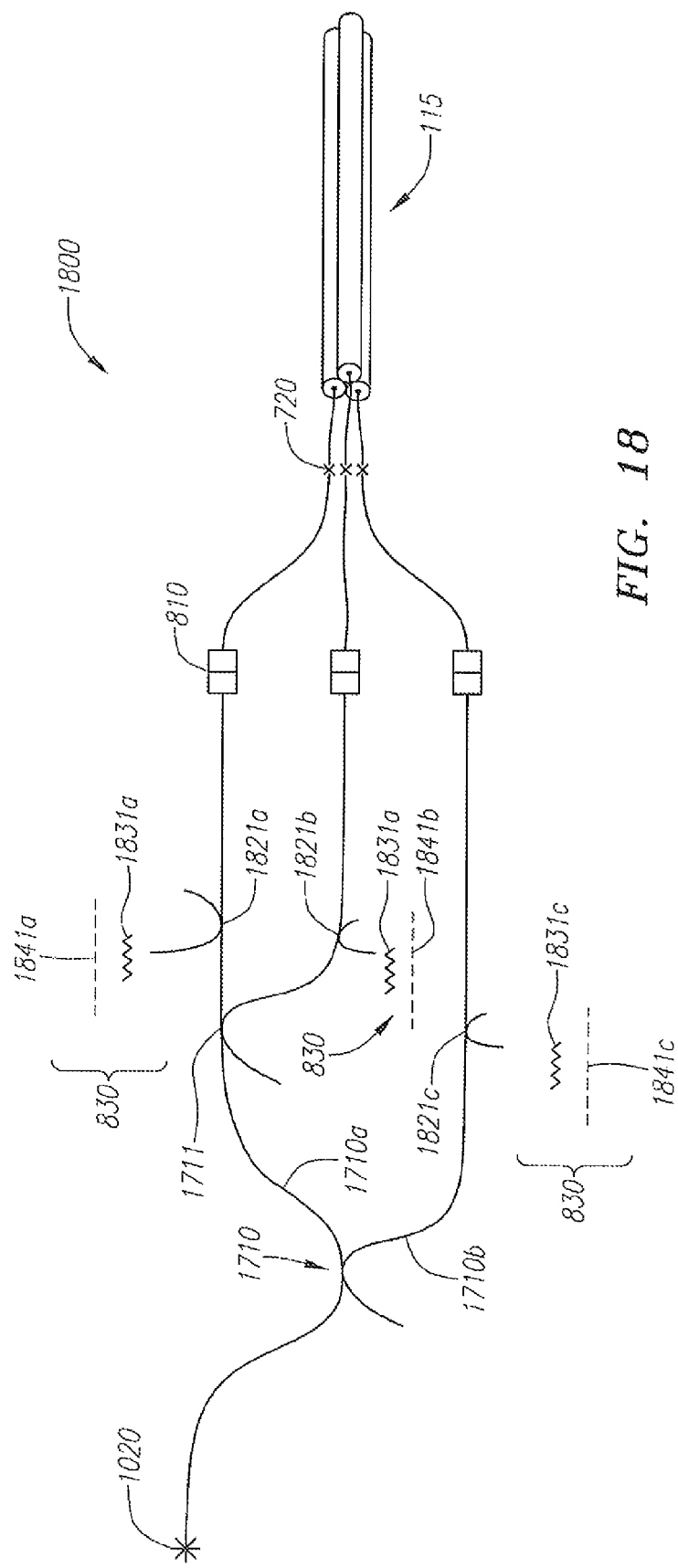
FIG. 18 schematically illustrates a fiber grating bend sensor system constructed according to one embodiment that includes a broadband light source and an output or read out unit that includes dispersion elements and charge coupled device arrays to monitor each optical fiber containing fiber grating sensor arrays.

FIG. 18 illustrates a system 1800 that is also configured for a combination of three different multiplexing methods: amplitude multiplexing, spectral profile multiplexing, and wavelength division multiplexing. The system 1800 includes a broadband light source 1020 such as a fiber light source. Light 1022 emitted by the light source 1020 is split by a series of splitters or couplers 1710, 1711 into three fiber lines (although another splitter coupler could be used to support a fourth fiber line in a manner similar to that shown in FIG. 17). These three lines are in turn connected via standard fiber connectors 810 to the three fibers 116a-c associated with the fiber grating bend sensor array 302. Fusion splices 720 are used to match the larger standard diameter optical fibers 815 to the smaller diameters associated with the fiber bend sensor array. Reflections 1026 from the fiber grating strain sensors 302 in each line of the bend sensor array are monitored by couplers 1821a-c directing light through an output or read out unit 1830 which, in the illustrated embodiment, is a dispersive output unit 1830 that includes one or more bulk gratings or dispersive element 1831a-c, such as a bulk grating or prism, and a detector array, such as a CCD array 1841a-c (generally 1841) that is used to monitor the spectrum associated with all the fiber gratings in that line of the array. Examples of calibrated CCD arrays 1841 that may be utilized for this purpose are available from Ibsen Photonics A/S, Ryttermarken 15-21, DK-3520, Farum, Denmark, and BaySpec, Inc., 101 Hammond Avenue, Fremont Calif.

Figure 19:
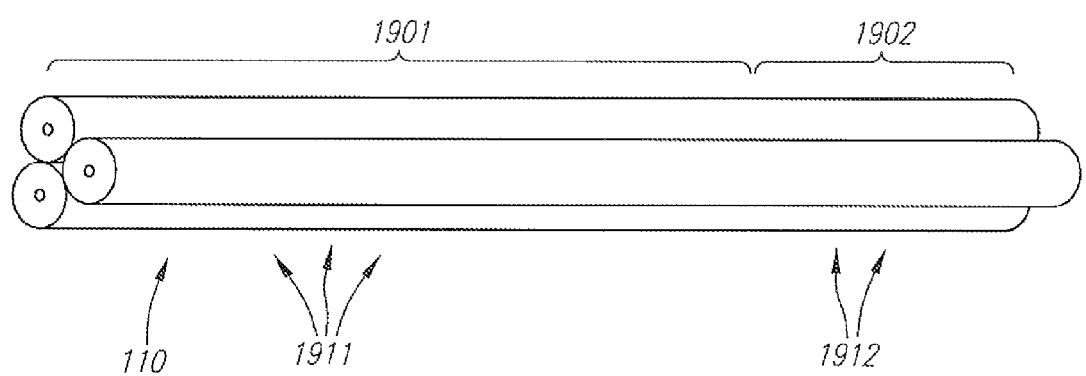
FIG. 19 illustrates one embodiment in which different sections of a multi-fiber optical bend sensor that have different bending characteristics include different densities of fiber gratings and that may be used in surgical and other applications.

Referring to FIG. 19, in cases in which embodiments are utilized in a catheter 110 used during a robotic surgical procedure, the catheter 110 may have two distinct sensing regions 1901, 1902. In the first region 1901, bends are relatively small, and the catheter 110 is relatively stiff. The first region 1901 has sufficiently accurate bend measurements and may be made with a relatively low density 1911 of fiber grating sensors 302, e.g., about 4 cm spacing. The second region 1902 or distal end 111 of the catheter 110 may require a greater flexibility leading to a requirement for a very high density 1912 of fiber gratings in this area, e.g., about 0.5 cm spacing. Thus, in this embodiment, an optical fiber sensor 115 including one or more gratings is configured such that the number of gratings in a portion of the fiber core coupled to the proximal (less flexible) portion of the catheter instrument is less than a number of gratings in a portion of the fiber core coupled to the distal (more flexible) portion of the catheter, and the multiplexed fiber gratings may be supported by each of amplitude, spectrum and wavelength measurements.

Figure 20:
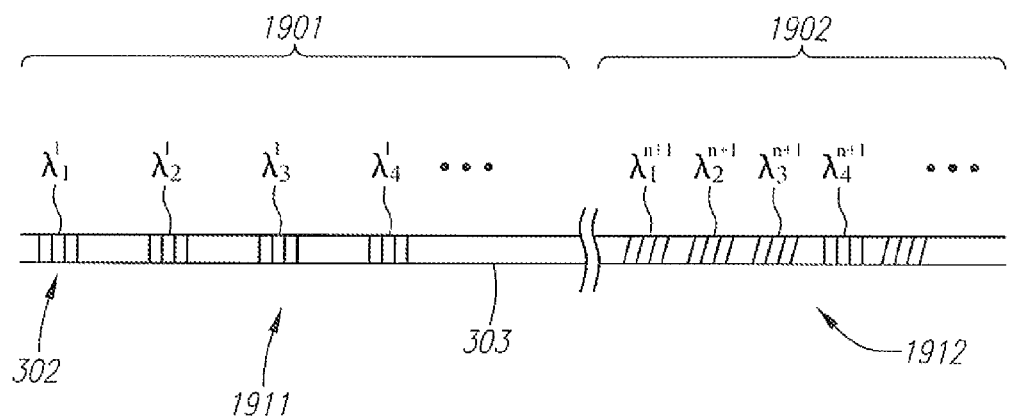
FIG. 20 illustrates one manner in which a variable density array can be implemented utilizing wavelength and amplitude multiplexing for use in surgical and other applications.

For example, in one embodiment as illustrated in FIG. 20, amplitude multiplexing or tagging (as described with reference to FIG. 15) is combined with wavelength division multiplexing to allow the configuration shown in FIG. 19 to be implemented using fiber gratings 302 with higher reflectivity. This configuration provides for lower cost read out approaches, reduced power consumption, smaller component sizes.

More particularly, FIG. 20 illustrates one line of the multi-fiber grating bend sensor array that may be used to realize variable density arrays without loss of accuracy. With these embodiments, an optical fiber sensor 115 includes one or more optical fiber cores 303 having a distribution of Bragg gratings 302 in which a number of gratings 302 in a portion of the fiber core 303 coupled to the proximal portion of the catheter instrument is lower than a number of gratings 302 in a portion of the fiber core 303 coupled to the distal portion of the catheter.

In the illustrated embodiment, fiber gratings 302 at wavelength one and four different amplitudes are used the support the first portion of the array. Additional wavelengths up to n could also be used for this section. In the higher density area 1902, the first wavelength used is labeled n+1 and it also has four amplitudes associated with it. It is possible that an output unit might support more than four amplitude levels. Side lobes 1602 associated with tagging fiber gratings 302 via "chirp" might also be used to extend each wavelength band. These techniques have the potential to considerably extend the capabilities of many fiber grating output units that are currently utilizing only wavelength division multiplexing capabilities that may be extended to support additional elements.

In another embodiment, overlaying fiber grating spectral profiles is done when the fiber gratings 302 are not strained. For example, in an embodiment illustrated in FIGS. 21A-D, two fiber gratings 302 have lengths of 2 mm and 4 mm for providing high density multiplexing and less complex signal processing. Other examples may involve other ratios of lengths, and there may be more than two gratings 302 to have more grating sensors supported by a single spectral band. Thus, the lengths of gratings 302 shown in FIGS. 21A-B and FIGS. 21C-D are provided as examples of how embodiments may be implemented.

In embodiments illustrated in FIGS. 21A-D, an optical fiber sensor 115 that includes multiplexed Bragg gratings 302 utilizes substantially the same spectral space. With these embodiments, a first grating may be written at a wavelength $\lambda_1$, and a second or other grating may be written at wavelengths that are symmetrically displaced from the central wavelength $\lambda_1$ such that overlaid gratings are written at $\lambda_1+\epsilon$ and $\lambda_1-\epsilon$. In this manner, multiple fiber gratings 302 having different periods may be written at the same physical location. Such fiber gratings 302 may be of the same or different lengths. These overlaid gratings 302 can operate at the same location providing two signals. Further aspects of overlaid gratings 302 and fabrication thereof are provided in U.S. Pat.

Nos. 5,591,965 and 5,627,927, the contents of which are incorporated herein by reference in their entirety for all purposes.

Embodiments may also include one or more additional symmetrical, spatially displaced sets of overlaid gratings. In these embodiments, the spectral spacing of the overlaid gratings may be at $\lambda_1+\epsilon$ and $\lambda_1-\epsilon$, or at $\lambda_1+2\epsilon$ and $\lambda_1-2\epsilon$. Thus, for example, a first grating may be written at a wavelength $\lambda_1$, a second spatially displaced set of overlaid gratings 302 may be written at $\lambda_1+\epsilon$ and $\lambda_1-\epsilon$, and a third spatially displaced set of overlaid gratings 302 may be written at $\lambda_1+2\epsilon$ and $\lambda_1-2\epsilon$. Other "n" numbers of spatially displaced set of overlaid gratings at $\lambda_1+n\epsilon$ and $\lambda_1$ may also be utilized.

In one embodiment, $\epsilon$ is about 0.5 nm to about 2 nm, e.g., about 2 nm. Thus, in the embodiment illustrated in FIGS. 21A-B, a fiber grating having a length of 4 mm 2101 can be written at a wavelength of 1550 nm 2111, a fiber grating having a length of 2 mm 2102 can be written at a wavelength of 1552 nm 2112, and another grating having a length of 2 mm 2103 can be written at a wavelength of 1548 nm 2113. Thus, the 2 mm gratings 2102 and 2103 are overlaid or applied on top of each other, whereas the 4 mm grating 2101 is not.

Figure 21A:
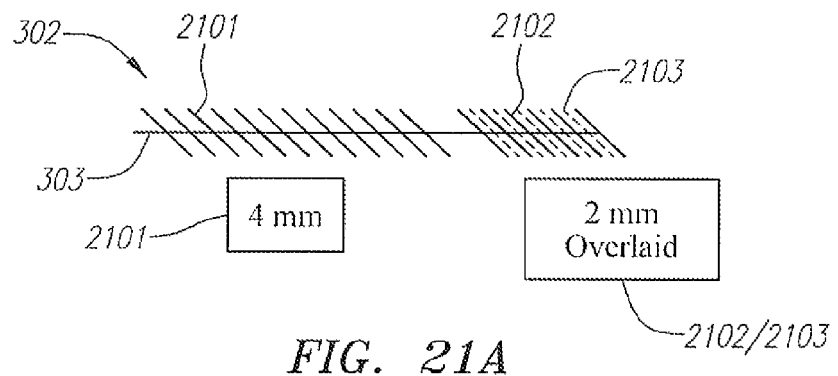
Figure 21B:
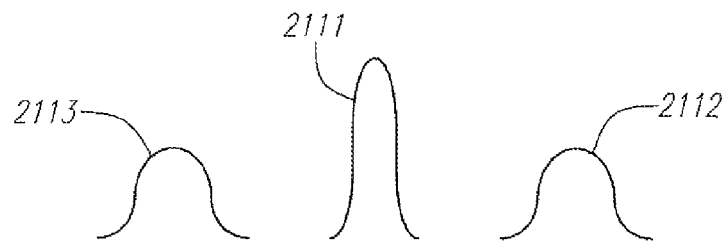
Figure 21C:
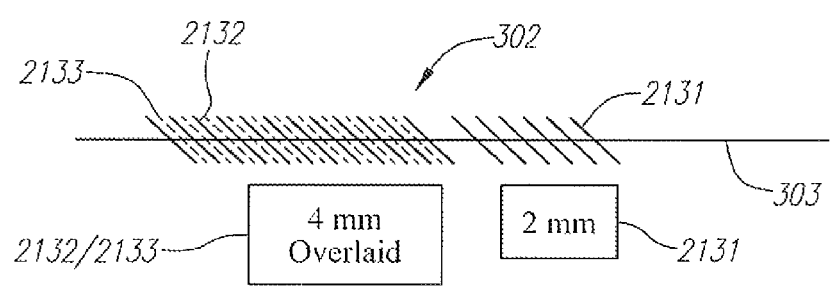
Figure 21D:
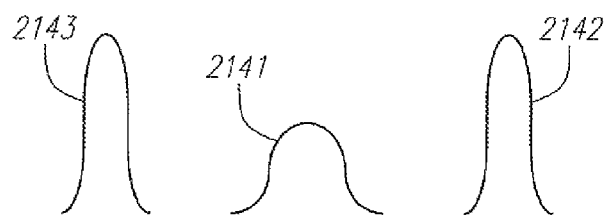

Referring to FIGS. 21C-D, in another embodiment, a fiber grating having a length of 2 mm 2131 is written at a wavelength of 1550 nm 2141, a grating having a length of 4 mm 2132 is written at a wavelength of 1552 nm 2142, and another grating having a length of 4 mm 2133 is written at a wavelength of 1548 nm 2143. Thus, the 4 mm gratings 2132 and 2133 are overlaid or applied on top of each other, whereas the 2 mm grating 2131 is not.

In the embodiments illustrated in FIGS. 21A-D, the spectral spacing utilized for overlaid gratings is symmetrical about a central wavelength $\lambda_1$ (1550 nm as an example), and the wavelength used for preparing other overlaid gratings has a spectral spacing $\epsilon$ from this wavelength. In the embodiments described above, spectral spacing $\epsilon$ is 2 nm such that overlaid gratings are written at wavelengths of 1048 nm and 1052 nm. Other embodiments may involve other wavelengths $\lambda_1$ and spectral spacings $\epsilon$.

Both of the embodiments illustrated in FIGS. 21A-B and 21C-D increase spatial density as a result of utilizing fiber gratings that are written over each other. In these embodiments, since the outer spectral profiles represent fiber gratings that are written on top of each other, they will "track" each other with axial strain. Also, the outer fiber gratings 2112, 2113 and 2142, 2143 are spaced about respective central grating profiles 2111 and 2141 and have a known spectral separation that will be fixed with axial strain. By monitoring the "centroid" of the two outer spectral profiles the axial strain of that strain sensor location may be monitored, and if there is any overlay with the central spectral profile, the interacting peak has a "known" position that would simplify processing. One advantage of this configuration is that it allows for use of less complex algorithms such that "peak" detection can be applied more effectively. It should also be noted that these configurations and methods may be applied or extended where the quantity of overlaid fiber gratings is, for example, greater than two, such that single, dual and tri-overlaid gratings occupy the same spectral space in order to increase grating density by doubling or tripling density, or increasing by other degrees depending on the number of overlaid gratings.

In another embodiment, both amplitude and side lobe tagging (as shown in FIG. 16) may be utilized. Such embodiments may allow for even higher density multiplexing. In terms of signal process the overlaid fiber grating approach described in association with FIG. 21 has the advantage that only peaks need be tracked to separate out fiber gratings. Since this simplifies signal processing for conventional commercially available read out units this means the system can support significantly higher operational speeds.

While the embodiments illustrated in FIGS. 21A-D are symmetrical or have uniform displacement $\epsilon$ from a wavelength $\lambda_1$ (which is 1550 nm in the illustrated embodiments), in other embodiments, the displacement may vary or be non-uniform such that overlaid gratings are written at wavelengths that are not equally displaced, or are asymmetrical relative to, a given wavelength $\lambda_1$. More specifically, in another embodiment involving dual overlaid gratings (as generally illustrated in FIGS. 21A-D), an optical fiber sensor 115 including multiplexed Bragg gratings using a substantially same spectral space includes a first grating that is written at a wavelength $\lambda_1$ and a second spatially displaced set of dual overlaid gratings (second and third gratings) written at wavelengths of $\lambda_1+\alpha_1$ and $\lambda_1-\beta_1$. The spatial distribution is asymmetrical as a result of $\alpha_1$ not being equal to $\beta_1$. Thus, for example, a first grating having a length of 4 mm can be written at a wavelength $\lambda_1$ of 1550 nm, and second and third overlaid gratings having a length of 2 mm can be written at wavelengths of 1045 nm and 1052 nm.

Other embodiments include a third spatially displaced set of dual overlaid gratings written at wavelengths of $\lambda_1+\alpha_2$ and $\lambda_1-\beta_2$, where $\alpha_2$ is not equal to $\beta_2$, and other embodiments may include other numbers "n" of spatially displaced sets of dual overlaid gratings that are written at $\lambda_1+\alpha_n$, and $\lambda_1-\beta_n$, where $\alpha_n$ is not equal to $\beta_n$. Thus, for example, a first grating having a length of 4 mm can be written at a wavelength $\lambda_1$ of 1550 nm, second and third overlaid gratings having a length of 2 mm can be written at wavelengths of 1045 nm and 1052 nm, and fourth and fifth overlaid gratings having a length of 2 mm can be written at wavelengths of 1047 nm and 1054 nm. Other embodiments may involve other wavelengths $\lambda_1$ and spectral spacings $\epsilon$. Similar configurations can be implemented using a third spatially displaced set of three overlaid gratings at $\lambda_1+\alpha_2$, $\lambda_1-\beta_2$ and $\lambda_1-\omega_2$, where $\alpha_2$, $\beta_2$, and $\omega_2$ are not equal, and "n" additional spatially displaced sets of n overlaid gratings $\lambda_1+\alpha_n$, $\lambda_1-\beta_n$, $\lambda_1-\omega_n$ ... $\lambda_1-\zeta_n$, where the spectral displacements of the overlaid gratings from $\lambda_1$ are not equal.

Thus, it should be understood that gratings of different lengths can be written at different wavelengths, certain gratings may be overlaid with other gratings, whereas other gratins are single or stand alone gratings, and the distribution of wavelengths that are used to write gratings may be uniform or non-uniform or asymmetrical.

Having described various apparatus and method embodiments in detail, further details of an example of a robotic surgical system and components thereof in which embodiments of the invention may be implemented are described with reference to FIGS. 22A-26B. As explained above, one application of embodiments is surgical applications, e.g., minimally invasive surgical applications. Thus, it should be understood that embodiments can be used in other applications and for other purposes, and that the following description is provided as one example of how embodiments may be implemented.

FIGS. 23A-B and 26A-B illustrate how embodiments of the invention can be implemented and within a robotic surgical system. A description a system and methods for utilizing localization data for closed-loop control of a robotic catheter system in which embodiments may be implemented is provided with reference to FIGS. 22A-25F.

Certain figures illustrate an optical fiber sensor 115 coupled to or associated with a component of a robotic surgical system. During use, such fiber sensors 115 may be integrated within components, e.g., positioned within a lumen 205 defined in a wall of a catheter 110. For ease of illustration, certain figures generally illustrate an optical fiber sensor 115 coupled to or associated with components of a robotic surgical system, but it should be understood that the optical fiber sensor 115 can be positioned on or within various components and may be connected to various other components of the robotic surgical system and optical systems and units.

Figure 22A:
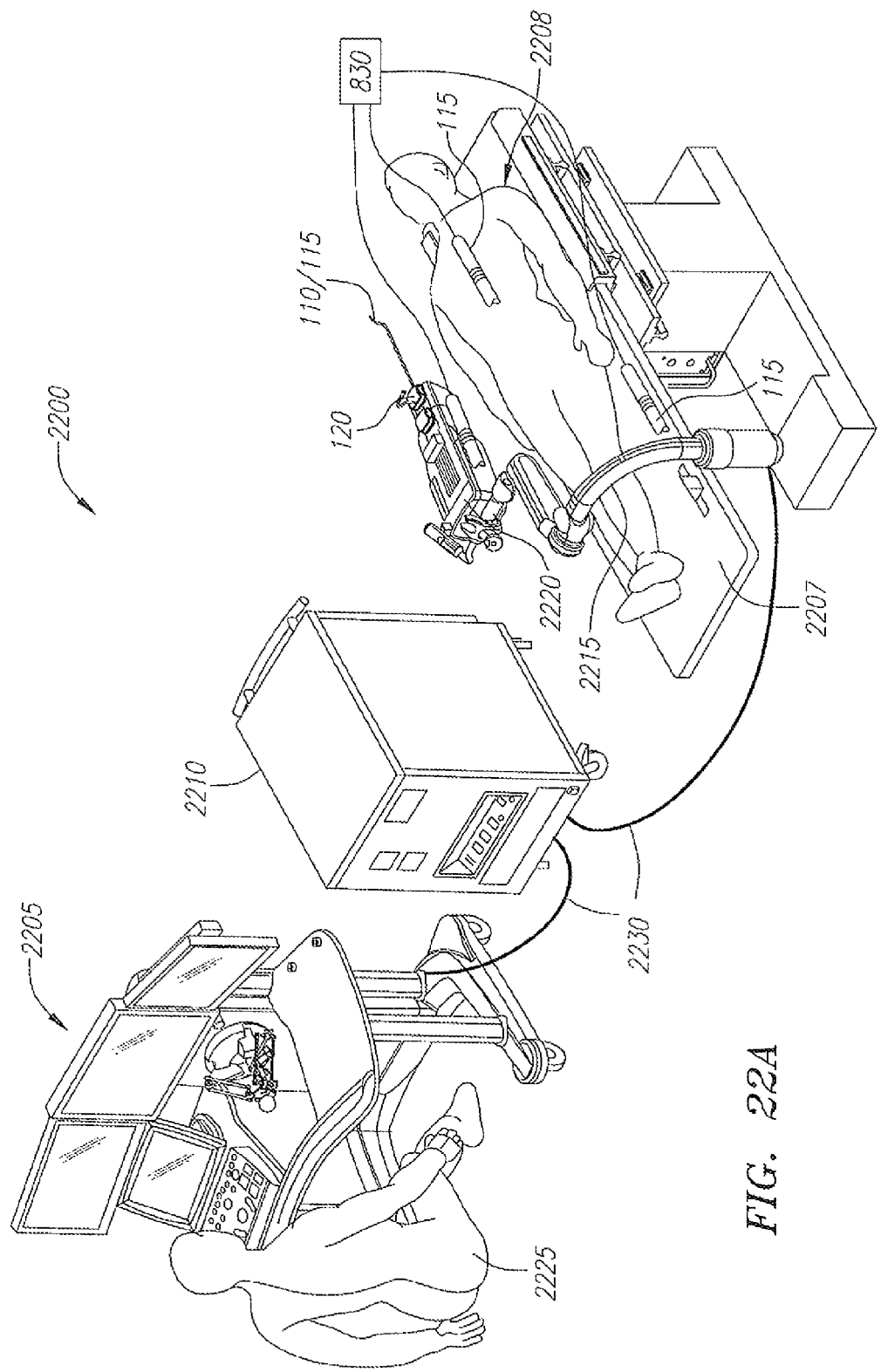
Figure 22B:
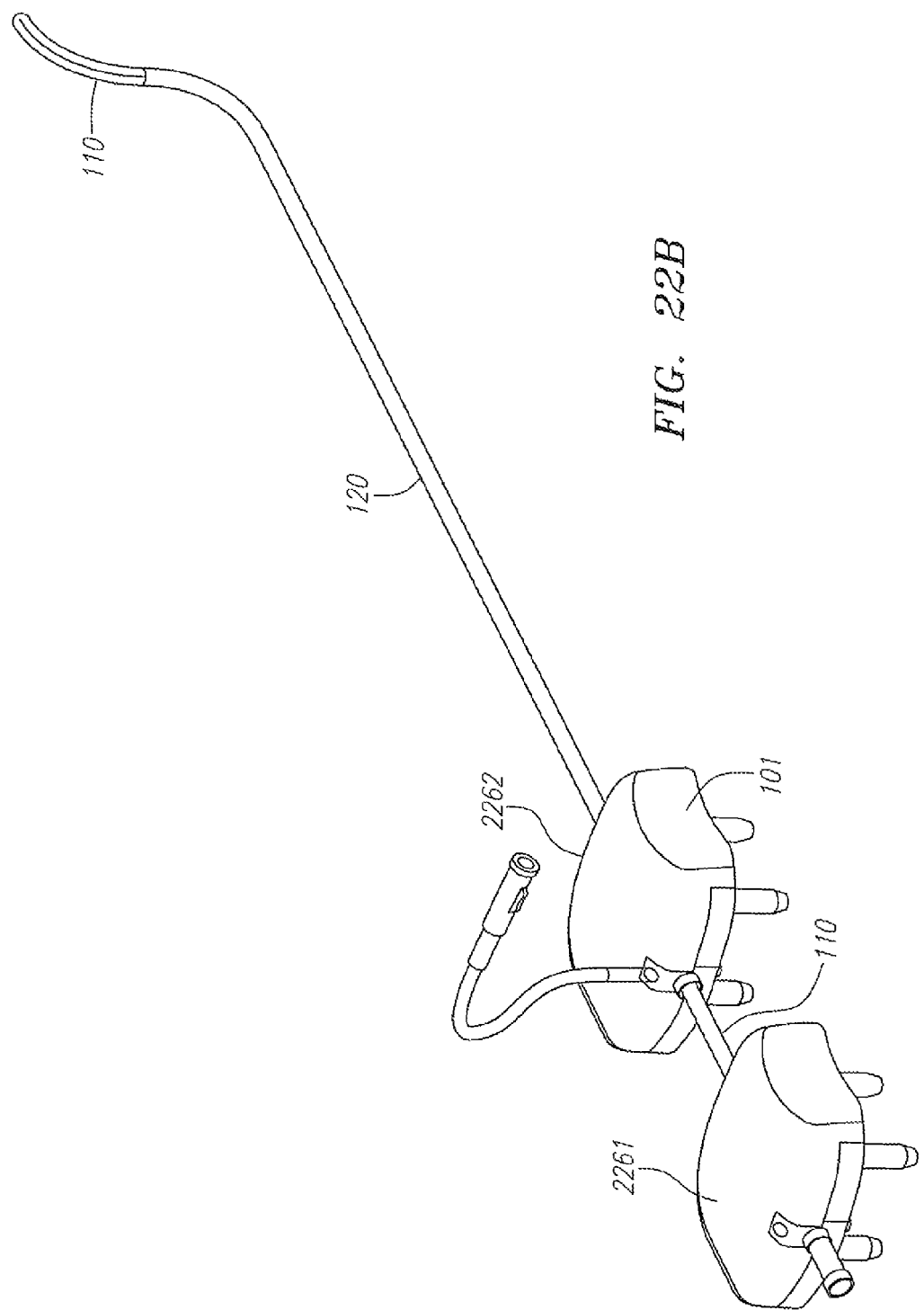
Figure 22C:
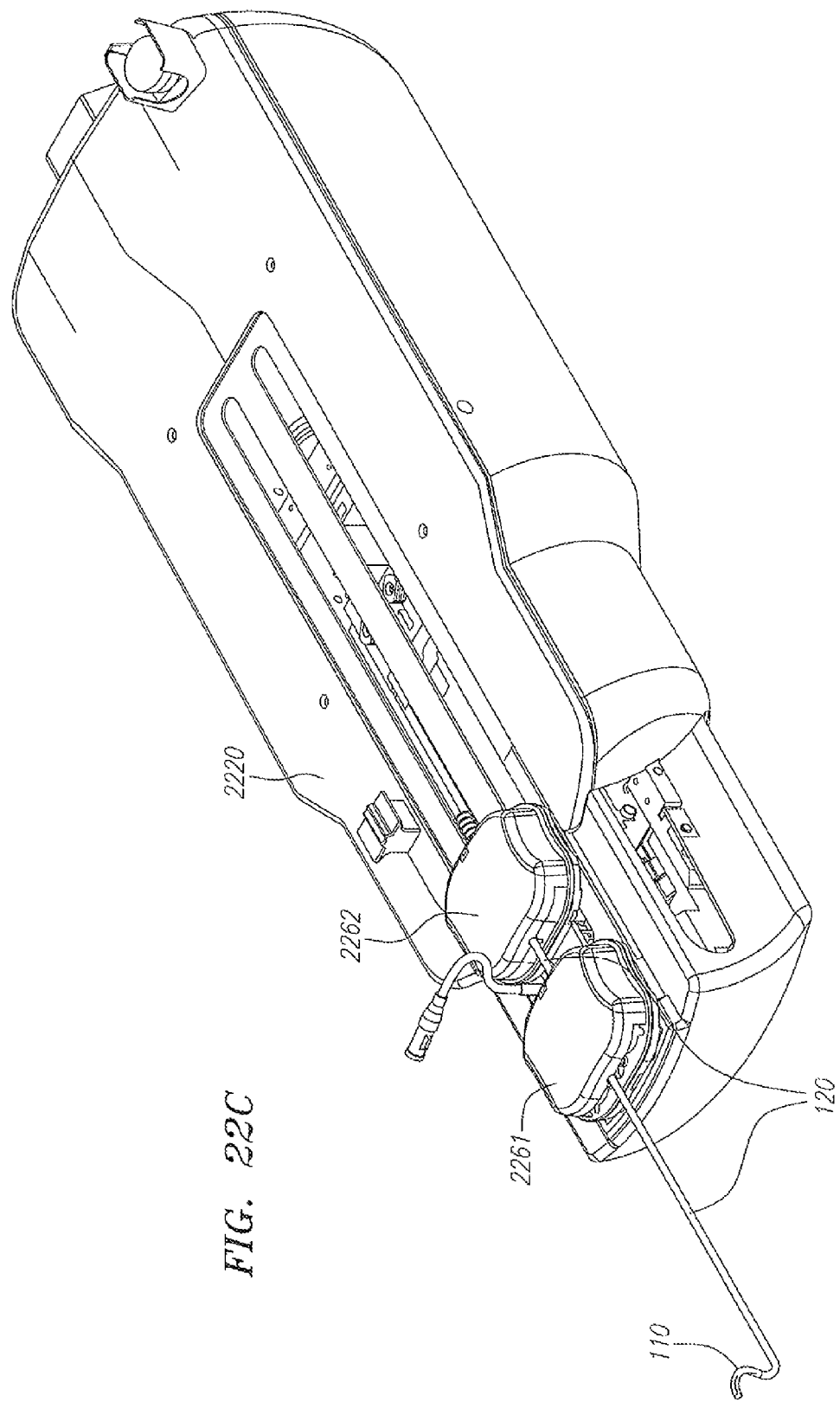

Referring to FIGS. 22A-C, one example of a robotic surgical system 2200 in which embodiments of the invention that utilize an optical fiber sensor 115 may be implemented includes an operator work or control station 2205, which may be configured as, or include control, processor or computer software and/or hardware to be configured as, a controller 1040. Of course, the controller 1040 and control station 2205 may be different control components. The workstation 2205 is located remotely from an operating table 2207, an electronics rack 2210, a setup joint mounting brace 2215, and motor-driven controller in the form an instrument driver 2220. A surgeon or operator 2225 seated at the operator workstation 2205 monitors a surgical procedure, patient 2208 vitals, and controls one or more flexible catheter assemblies that may include a coaxially-associated instruments of an outer sheath catheter 120, an inner coaxially-associated catheter 110 such as a guide catheter, and a working instrument 240 such as a guidewire, a pusher wire, an ablation catheter, a laser ablation fiber, a grasper, a collapsible basket tool, etc., which is positioned within the working lumen defined by the inner catheter 110.

Although the various components of the system 2200 are illustrated in close proximity to each other, components may also be separated from each other, e.g., in separate rooms. For example, the instrument driver 2220, the operating table 2207 and a bedside electronics box may be located in the surgical area, whereas the operator workstation 2205 and the electronics rack 2210 may be located outside of the surgical area behind a shielded partition. System 2200 components may communicate with other components via a network, thus allowing for remote surgery such that the surgeon 2225 may be in the same or different building or hospital site. For this purpose, a communication link may be provided to transfer signals between the operator control station 2205 and the instrument driver 2220. Components may be coupled together via cables 2230 as necessary for data communication. Wireless communications may also be utilized.

One suitable operator workstation 2205 includes a console having one or more display screens, which may serve as display 1040, a master input device (MID) and other components such as a touchscreen user interface, and data glove input devices. The MID may be a multi-degree-of-freedom device that includes multiple joints and associated encoders. MID software may be a proprietary module packaged with an off-the-shelf master input device system, such as the Phantom® from SensAble Technologies, Inc., which is configured to communicate with the Phantom® Haptic Device hardware at a relatively high frequency as prescribed by the manufacturer. Other suitable MIDs are available from suppliers such as Force Dimension of Lausanne, Switzerland. The MID may also have haptics capability to facilitate feedback to the operator, and software modules pertinent to such functionality may be operated on the master computer. An example of data glove software is a device driver or software model such as a driver for the 5DT Data Glove. In other embodiments, software support for the data glove master input device is provided through application drivers such as Kaydara MOCAP, Discreet 3D Studio Max, Alias Maya, and SoftImage|XSI.

The instrument driver 2220 and associated flexible catheter assembly and working instruments may be controlled by an operator 2225 via the manipulation of the MID 2234, data gloves, or a combination of thereof. During use, the operator 2225 manipulates a pendant and MID to cause the instrument driver 2220 to remotely control flexible catheters that are mounted thereon. Inputs to the operator workstation 2205 to control the flexible catheter assembly can entered using the MID and one or more data gloves. The MID and data gloves, which may be wireless, serve as user interfaces through which the operator 2225 may control the operation of the instrument driver 2220 and any instruments attached thereto. It should be understood that while an operator 2225 may robotically control one or more flexible catheter devices via an inputs device, a computer or other controller of the robotic catheter system 2200 may be activated to automatically position a catheter instrument 110 and/or its distal extremity 111 inside of a patient 2208 or to automatically navigate the patient anatomy to a designated surgical site or region of interest.

A system architecture of a robotic catheter system 2200 includes a controller 1040 in the form of a master computer that manages operation of the system 2200. The master computer is coupled to receive user input from hardware input devices such as a data glove input device and a haptic MID. The master computer may execute MID hardware or software, data glove software and other software such as visualization software, instrument localization software, and software to interface with operator control station buttons and/or switches. Data glove software processes data from the data glove input device, and MID hardware/software processes data from the haptic MID. In response to the processed inputs, the master computer processes instructions to instrument driver computer to activate the appropriate mechanical response from the associated motors and mechanical components of the driver 2220 to achieve the desired response from the flexible catheter assembly including a sheath 120 and catheter or elongate instrument 110.

An example of a setup joint, instrument mounting brace or support assembly 2215 (generally referred to as a support assembly 2215) that supports the instrument driver 2220 above the operating table 2207 is an arcuate-shaped structure configured to position the instrument driver 2220 above a patient 2208 lying on the table 2207 for convenient access to desired locations relative to the patient 2208. The support assembly 2215 may also be configured to lock the instrument driver 2220 into position. In this example, the support assembly 2215 is mounted to the edge of a patient bed 2207 such that an assembly including a catheter 110 mounted on the instrument driver 2220 can be positioned for insertion into a patient 2208 and to allow for any necessary movement of the instrument driver 2220 in order to maneuver the catheter assembly during a surgical procedure.

As shown in FIGS. 22A-C, and as illustrated in FIG. 2, a flexible catheter assembly for use in embodiments includes three coaxially-associated instruments including an outer sheath catheter 120, an inner coaxially-associated catheter or guide catheter 110, and a working instrument (not illustrated in FIGS. 22A-C) such as a guidewire, pusher wire, ablation catheter, laser ablation fiber, grasper, collapsible basket tool, etc—a myriad of small working tools may be utilized and localized) positioned through the working lumen formed by the inner catheter 110.

In the illustrated example, a splayer 2261 has one or more control elements and is configured to controllably manipulate a flexible catheter 110, and a splayer 2262 has one or more control elements and is configured to controllably manipulate a sheath 120, which as a central lumen for receiving the catheter 110. The catheter instrument 110 also defines a lumen for passage of a working element or instrument 140. Prior to use, the catheter 110 is inserted into the sheath 120 such that these components are coaxially positioned. Both splayers 2261, 2262 are mounted to respective mounting plates on the instrument driver 2220, and the splayers 2261, 2262 are controlled to manipulate the catheter and sheath instruments 110, 120.

In one embodiment, a system includes an elongate instrument or catheter 110 having one or more control elements or pull wires operatively coupled to at least one servo motor of the instrument driver 2220 (e.g. as generally illustrated in FIG. 12) such that the instrument 110 moves in response to actuation of the at least one servo motor. The optical fiber sensor 115 supplies localization data indicative of a spatial position of at least a portion of the instrument 110, and the controller 1040 or other system control element controls actuation of the at least one servo motor in order to control movement of the instrument 210 based at least in part upon a comparison of an actual position the instrument 110 derived from the localization data to a projected position of the instrument derived from, for example, a kinematic model of the instrument 210.

As shown in various system figures, embodiments of optical fiber sensors 115 can be coupled to or integral with various system components. In various embodiments, an optical fiber sensor 115 can be coupled to or integral with a catheter or elongate instrument 110, a sheath 120, the instrument driver 2220, the patient's bed 2207, and/or attached to the patient 2208. For example, FIG. 22A illustrates an embodiment in which optical fiber sensors 115 are coupled to two system components (instrument driver 2200 and a bed or table 2207) and the patient 2208. A catheter or other elongate instrument 110 may also include an optical fiber sensor 115.

Figure 23B:
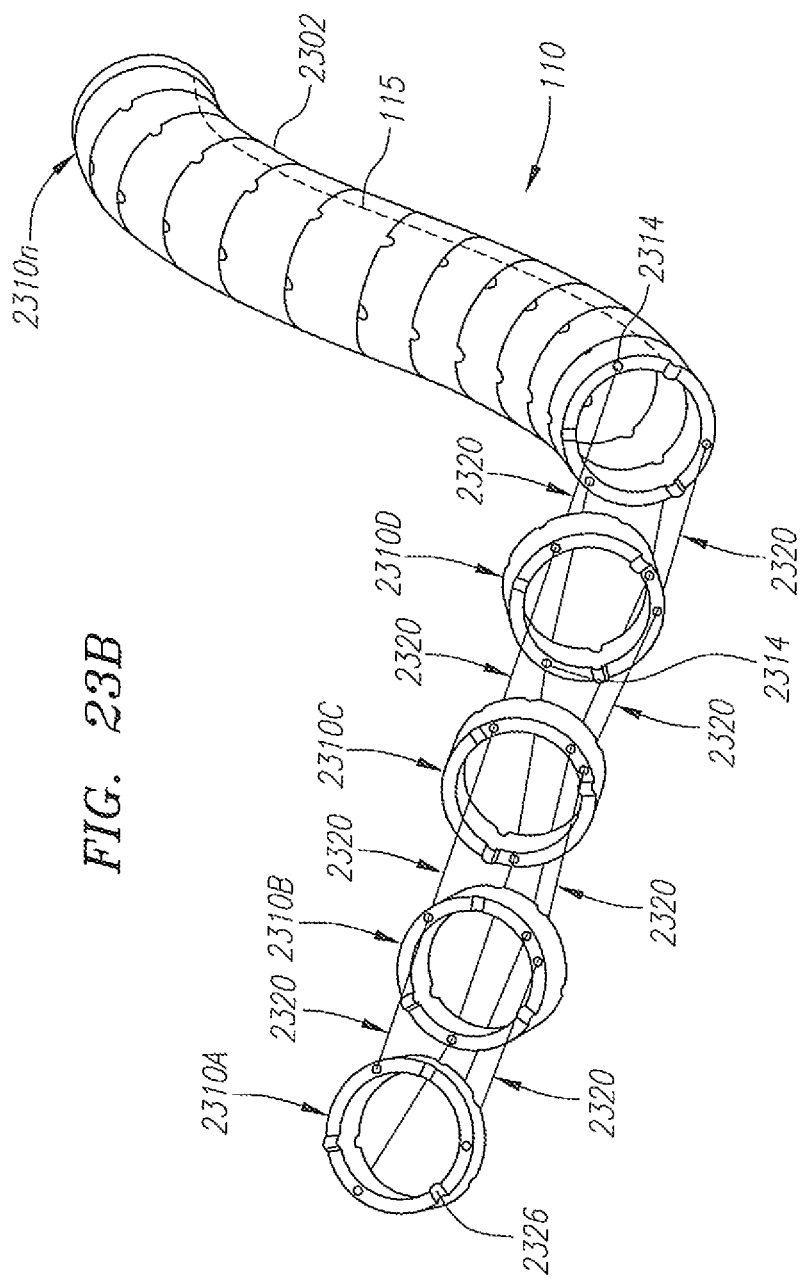
Figure 23C:
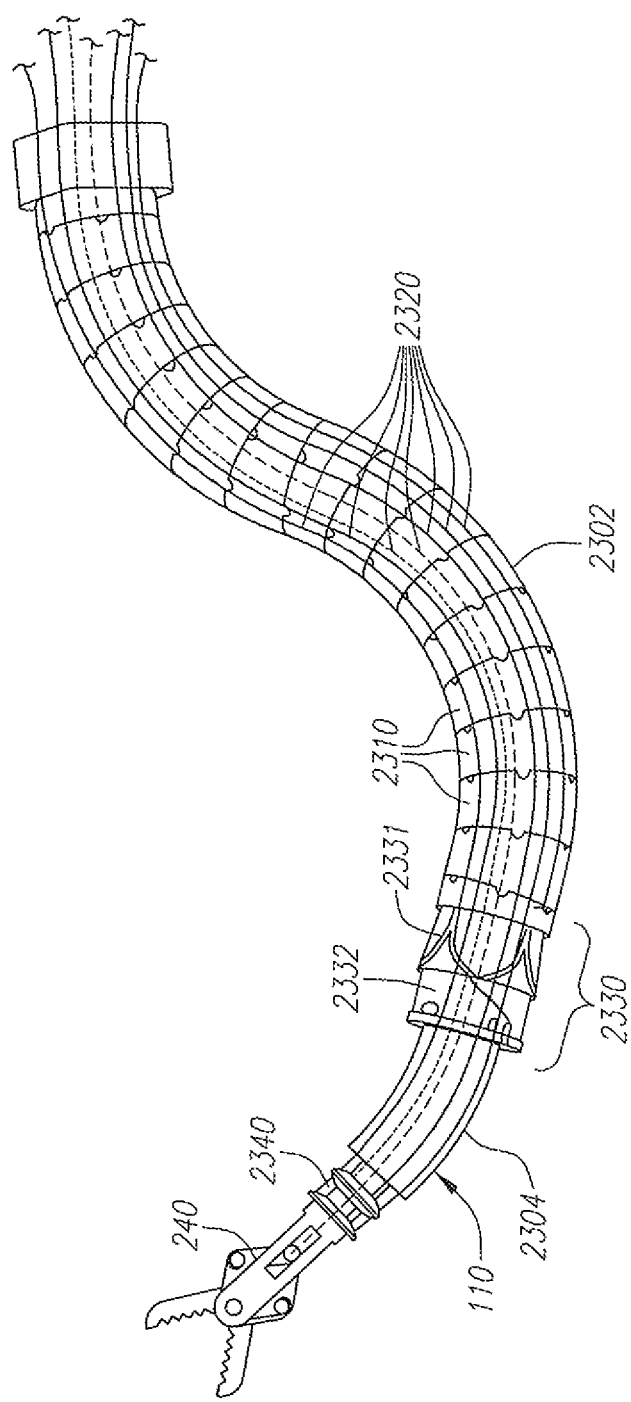

FIGS. 23A-C illustrate an elongate catheter 110 in the form of a sheath catheter 2302 through which another instrument such as a guide catheter 2304 may extend. According to embodiments, optical fiber sensors 115 can be coupled to or integral with the sheath catheter 2302 and/or the guide catheter 2304. In the illustrated embodiment, the sheath catheter 2302 includes multiple segments 2310(*a-n*) (generally segment 2310). Each segment 2310 may be generally the same shape, e.g. round ring-like structures, but may differ to some degree. Segments 2310 can also be other shapes, e.g., square, rectangular, triangular, pentagonal, hexagonal, octagonal, circular, spherical, elliptical, star, etc. Pull wires 2320 are operably coupled to each segment 2310 and extend through aligned passages, apertures or channels 2314 defined by a wall of each segment 2310. For example, a pull wire 2320 may be coupled to a distal most segment 2310 such that placing the pull wire 2320 in tension also places more proximal segments 2310 in tension. In another embodiment, the pull wires 2320 can be attached to some or all of the segments 2310, e.g., attached to an exterior surface of a segment 2310.

The wall of each segment 2310 can also define an aperture 213 (as illustrated in FIG. 2) for an optical fiber sensor 115. In this manner, control element s or pull wires 2320 and optical fiber sensors 115 are advantageously routed through the body or wall of segments 2320 rather than through an inner or central lumen defined by a collection of segments 2320. In this manner, embodiments advantageously reduce the components extending through the inner or central lumen, thereby providing more space through which other instruments and devices, such as a guide catheter 2304 and/or working instrument 240 may be inserted. Instruments can also be advanced through the sheath catheter 2302 more easily since the control elements 2320 and optical fiber sensor 115 do not interfere with these components.

Individual segments 2320 of a sheath catheter 2302 having shaped, interlocking top and bottom surfaces that allow segment 2320 to matingly engage adjacent segments 2320. In the illustrated embodiment, each segment 2320 includes mating teeth or protrusions 2326 and notches or grooves 2328 that matingly engagement each other such that interlocking segments 2320 are not rotatable relative to each other. In this manner, aligned interlocking segments 2320 collectively define a catheter or elongate body structure 120 that defines a lumen that extends through the plurality of segment 2320 bodies. While the figures illustrate a structural configuration of one embodiment of a segment 2320, other numbers and arrangements of teeth or protrusions 2326, notches or grooves 2328 and apertures 2314, 213 for control elements 2320 and optical fiber sensors 215 may be utilized. Further, individual segments 2320 may have different numbers of teeth or protrusions and notches depending on the need to provide additional stability, support, and rigidity to the sheath catheter 2302 when the sheath catheter 2302 is deployed.

With the sheath 2302 configuration illustrated, segments 2320 and be placed in tension to place the group of segments 2320 in tension or a rigid state, or placed in a relaxed, low tension or flexible state. Thus, one embodiment of a catheter or elongate instrument 120 in the form of a sheath catheter 2302 that may include an optical fiber sensor has controllable rigidity and can form a platform from which other instruments can extend and be controlled and provide rigidity and resistance to twisting or rotational loads on the sheath catheter 2302.

In addition to having an optical fiber sensor 115 as shown in FIG. 23A, a reference sensor may be utilized for purposes of system calibration. The reference sensor may, for example, be on a patient table or on an arm of a robotic surgical system. With this configuration, one or more position and/or orientation variables of the distal end portions of the respective instrument bodies are determined relative to the reference sensor.

Figure 24A:
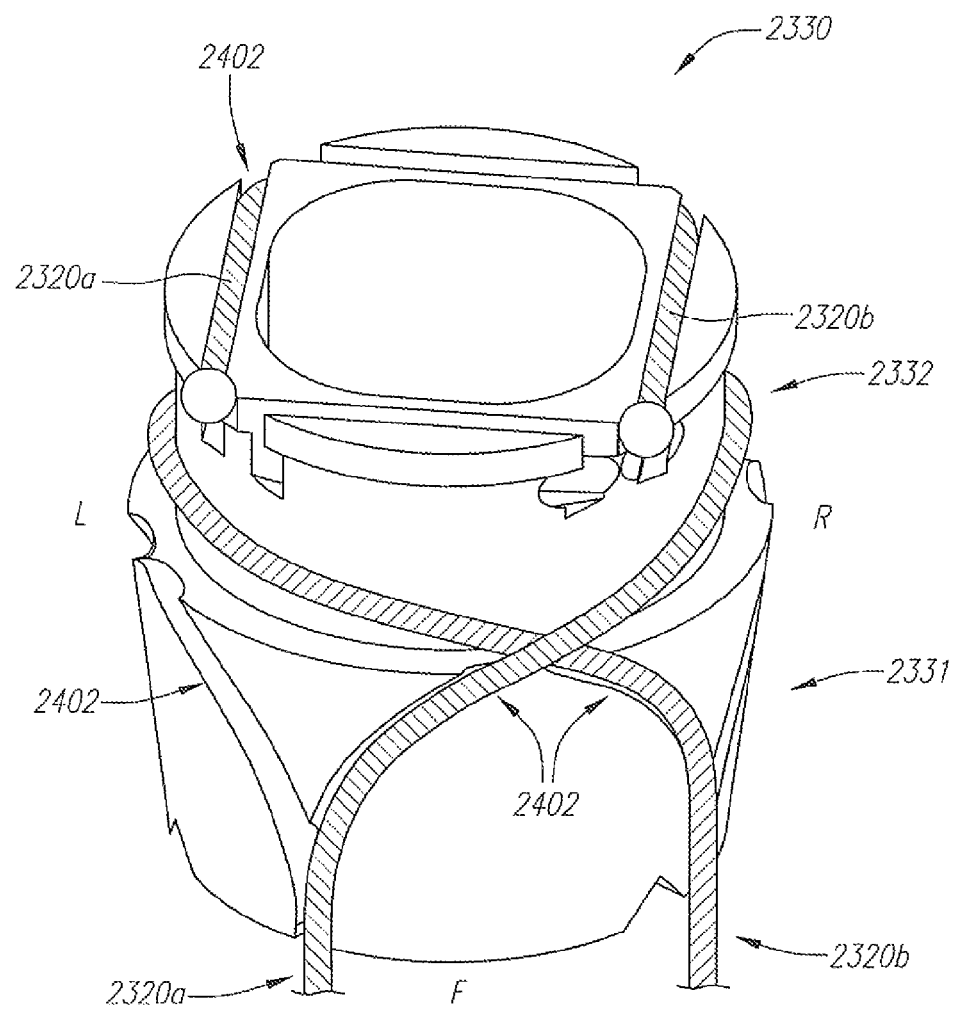
FIGS. 24A-D illustrate different views of a rotatable apparatus that interfaces with the sheath catheter illustrated in FIGS. 23A-C.
Figure 24B:
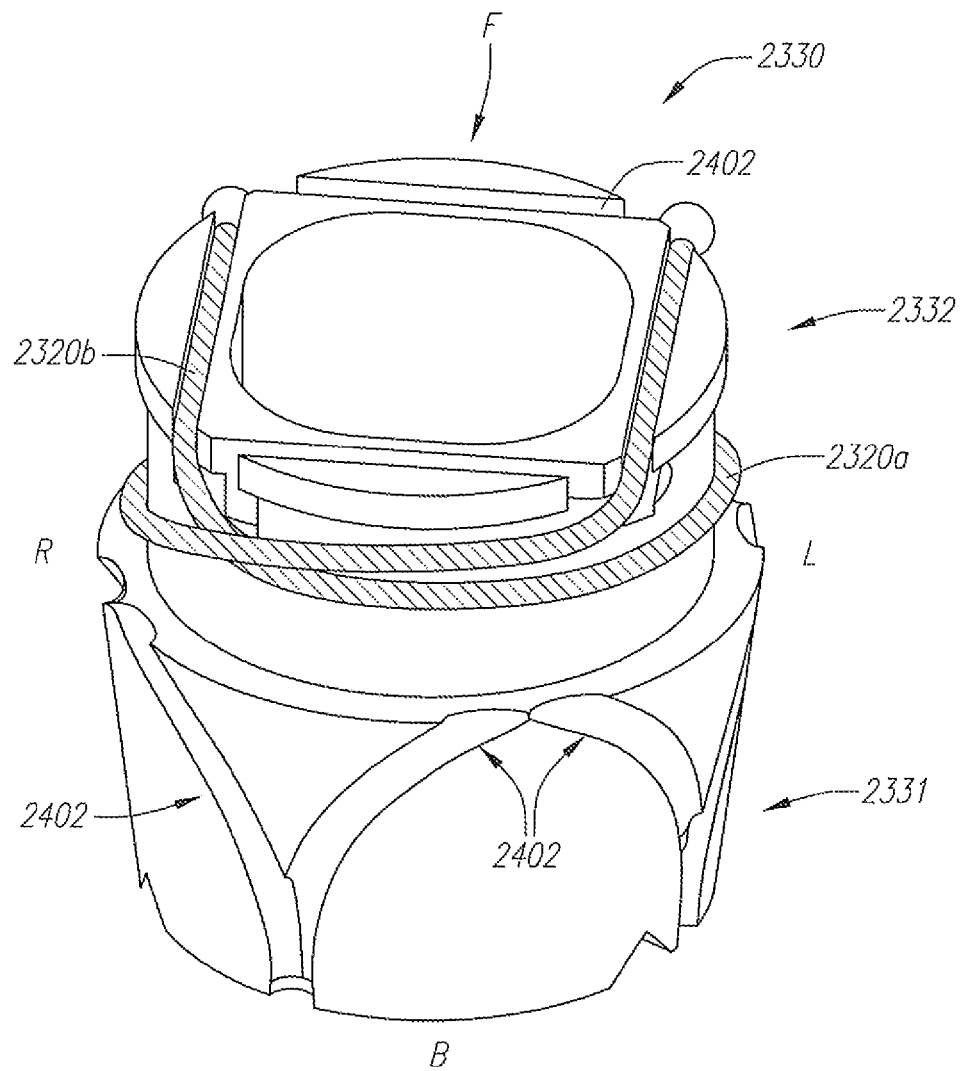
Figure 24C:
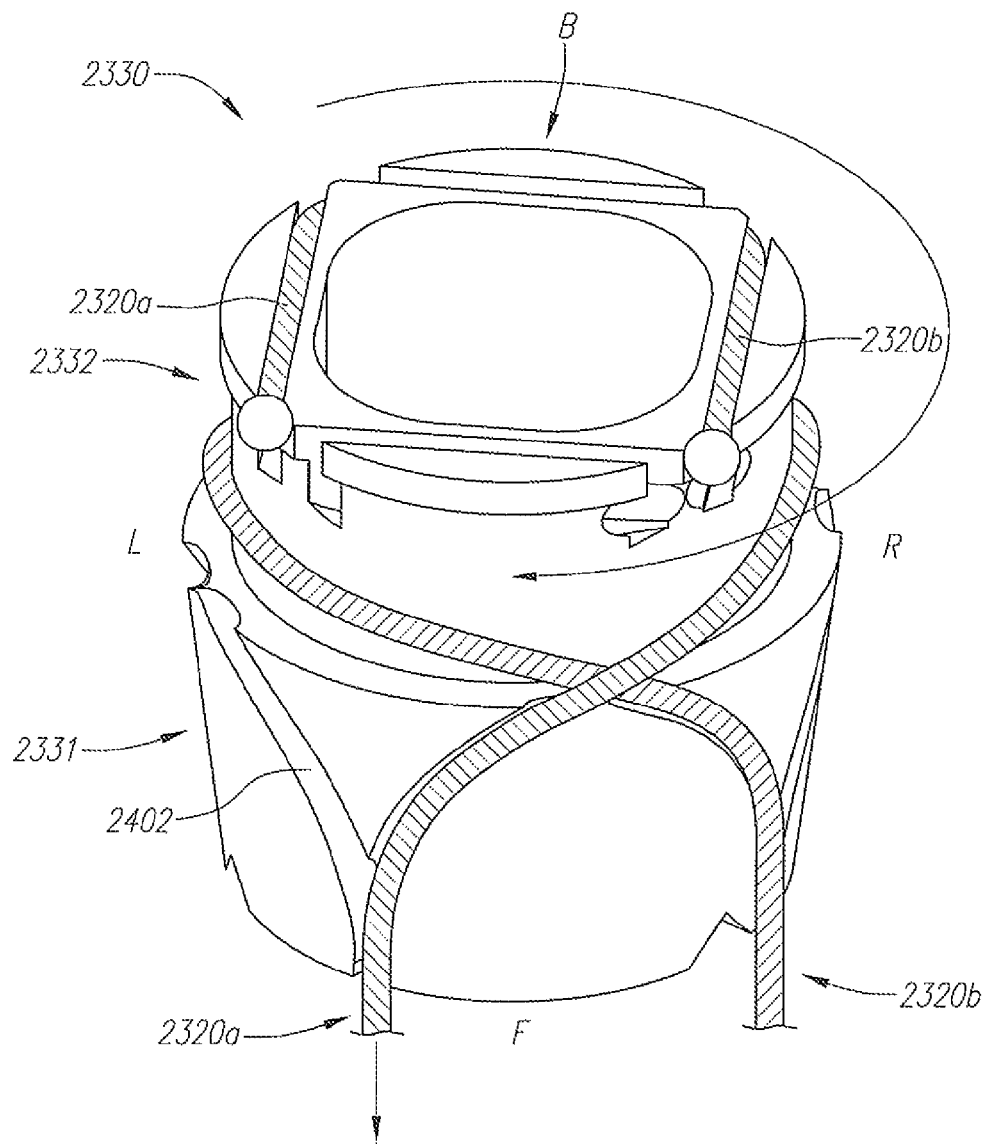
Figure 24D:
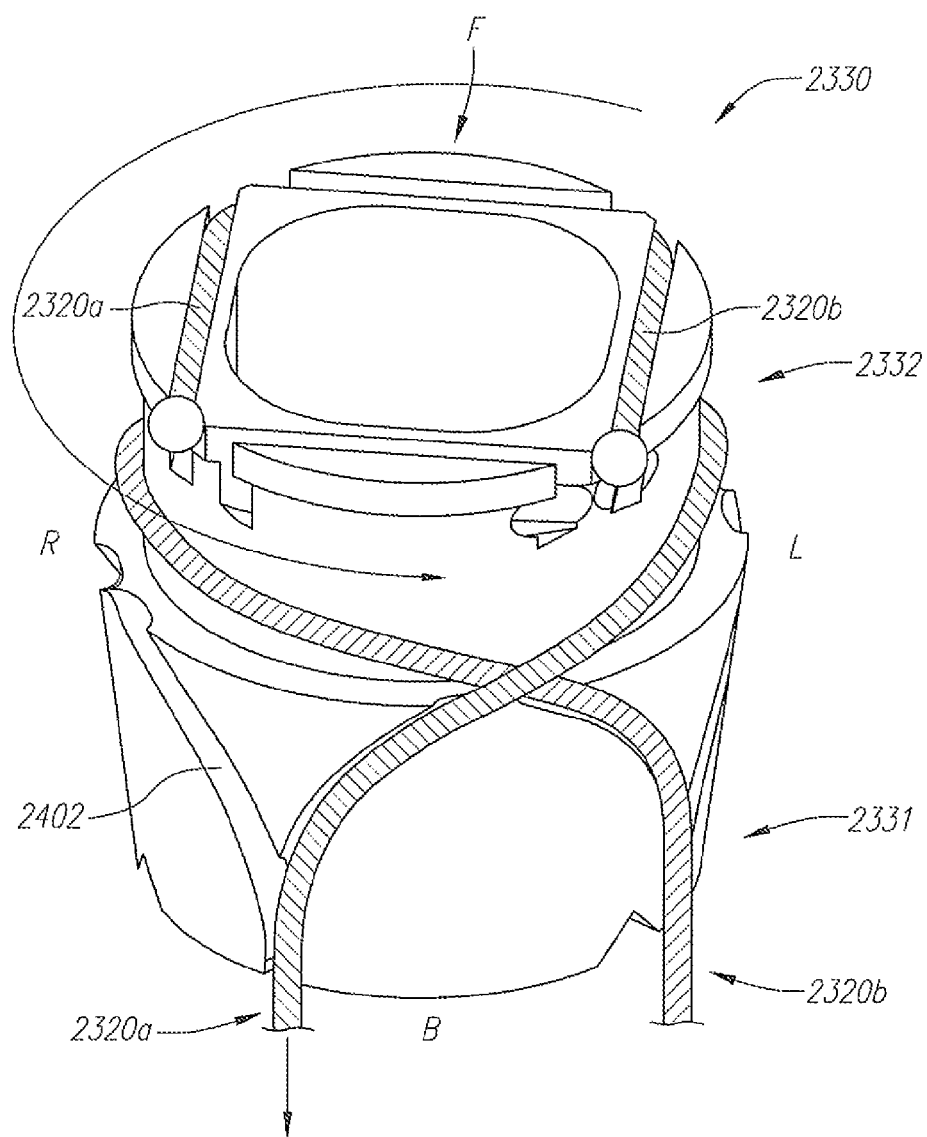
Figures 25A, 25B:
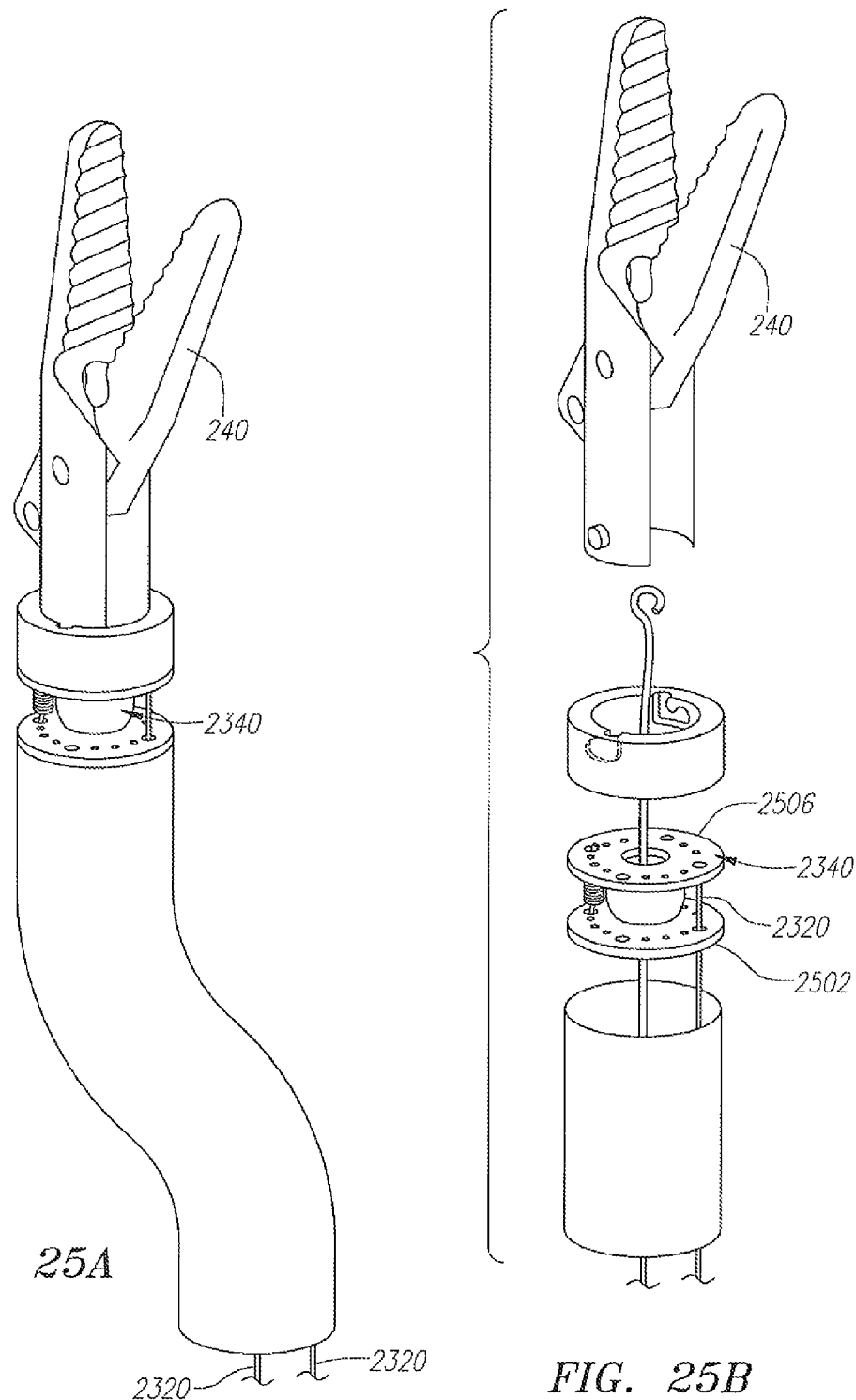

With continuing reference to FIG. 23A, and with further reference to FIGS. 24A-D, a rotatable apparatus 2330 is coupled to the sheath catheter 2302 and provides greater degrees of freedom and movement of a guide catheter 2304, an orientation platform 2340 and/or working instrument 140 coupled thereto or associated therewith. A rotatable apparatus 2330 may include an interface or wire guide apparatus 2331 and a rotatable collar, tool base or wire receive apparatus 2332 which are rotatably coupled together. Thus, a tool or other system component may be rotatably coupled to a distal end portion of a medical instrument, such as a sheath or guide catheter 2302, by manipulation of one or more control elements 2320 that extend through grooves formed within rotatable apparatus 2330 to rotate the collar component 2332 clockwise (FIG. 24C) and counter-clockwise (FIG. 24D).

As shown in FIGS. 24A-D, outer surfaces of the interface and collar components 2331, 2332 defines one or more guides, channels or grooves 2402 that serve to guide, direct or route control element 2320 (two control elements 2320*a,b* are illustrated). In the illustrated embodiment, control elements 2302 wrap around a substantial portion of the rotatable collar 2331 such that manipulation of control elements 2320 results in rotation of the rotatable collar 2332. FIG. 23C further illustrates how various control elements 2320 may extend through a sheath catheter 2302 are connected to different components. Thus, pulling or placing tension on the control element 2320 rotates the collar 2332 and associated instruments such as a guide catheter 2304 and working instrument 140, thereby advantageously providing rotational control as well as articulation control of system components.

Referring to FIG. 23A, and with further reference to FIGS. 25A-F, an orientation platform 2340 of a robotic instrument system is configured to control a working instrument 140 (one example of which is illustrated) coupled to a distal end of a catheter instrument 2304 or other instrument of a robotic medical system, e.g., a sheath 120 covered catheter 110. In the illustrated example, the interface or platform 2340 includes a base member or socket plate 2502 configured for coupling to a distal end of catheter instrument member, a spacer element 2504 and another socket plate or platform member 2506. The spacer element 2504 is retained or interposed between, and separates, the base member 2502 and the platform member 2506. The platform member 2506 is movable relative to the base member 2502 about the spacer element 2504. The interface or platform 2506 also includes a control element 2320, such as a pull wire, that extends through the catheter member, through an aperture defined by the base member 2502, and terminating at the platform member 2506. The platform 2340 may be used to control an orientation of the platform member 2506 and an orientation of the working instrument 140 are controllably adjustable by manipulation of the control element 2320.

Further aspects of system components illustrated in FIGS. 23A-25F are described in various applications previously incorporated by reference.

Figure 26A:
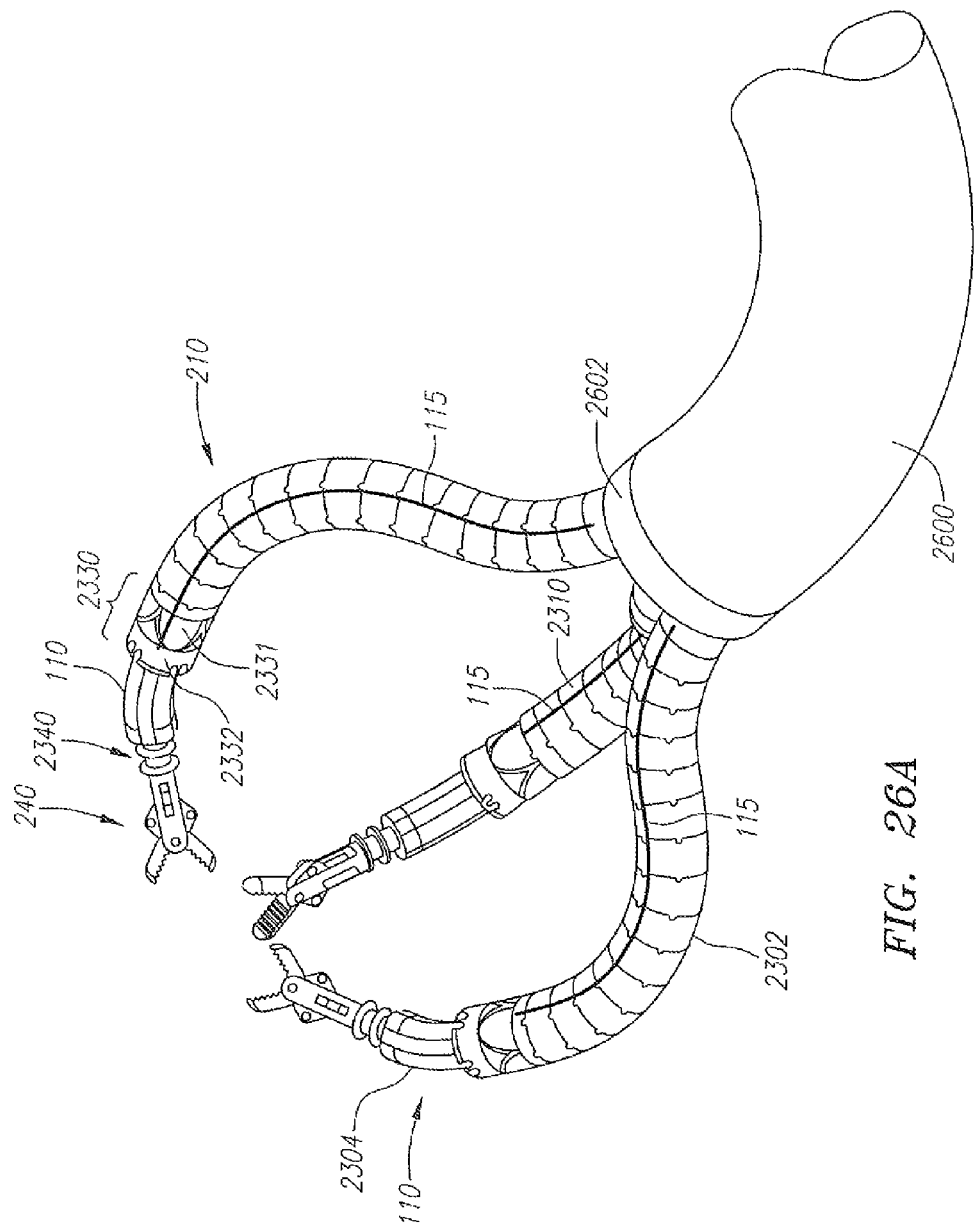

FIG. 26A illustrates another manner in which embodiments may be implemented in which multiple optical fiber sensors 115 are coupled to or integral with multiple catheters coupled to respective rotatable apparatus and orientation apparatus components described above, and which are advanced through an outer or master sheath 2600.

In the illustrated embodiment, each sheath catheter 2302 or a sub-portion thereof is localized utilizing an optical fiber sensor 115 which may be a Fiber Bragg Grating localization sensor. Other system components, such as an image capture device, may also be localized with an optical fiber sensor 115. Further, similar to other embodiments discussed above, other system components, such as an instrument driver 2220 and patient bed 2208 may also have optical fiber sensors 115. With this configuration, embodiments enable the entire environment (image capture device, each flexible arm, the main proximal arm, etc.) to be well characterized in near-real time, and the images from the image capture device, such as a fluoroscopy device, may be appropriately associated with representations, cartoons and images produced from the depicted devices. Thus, embodiments provide apparatus and methods for combining or fusing a shape and localization measuring fiber 115 and robotic surgical system components.

Additionally, similar to apparatus and method embodiments discussed above, optical fiber sensors 115 coupled to each system component may provide for determining and displaying the orientation and the roll of the tip of the elongate instruments. This is particularly useful when planning surgery or placing leads.

Figure 26B:
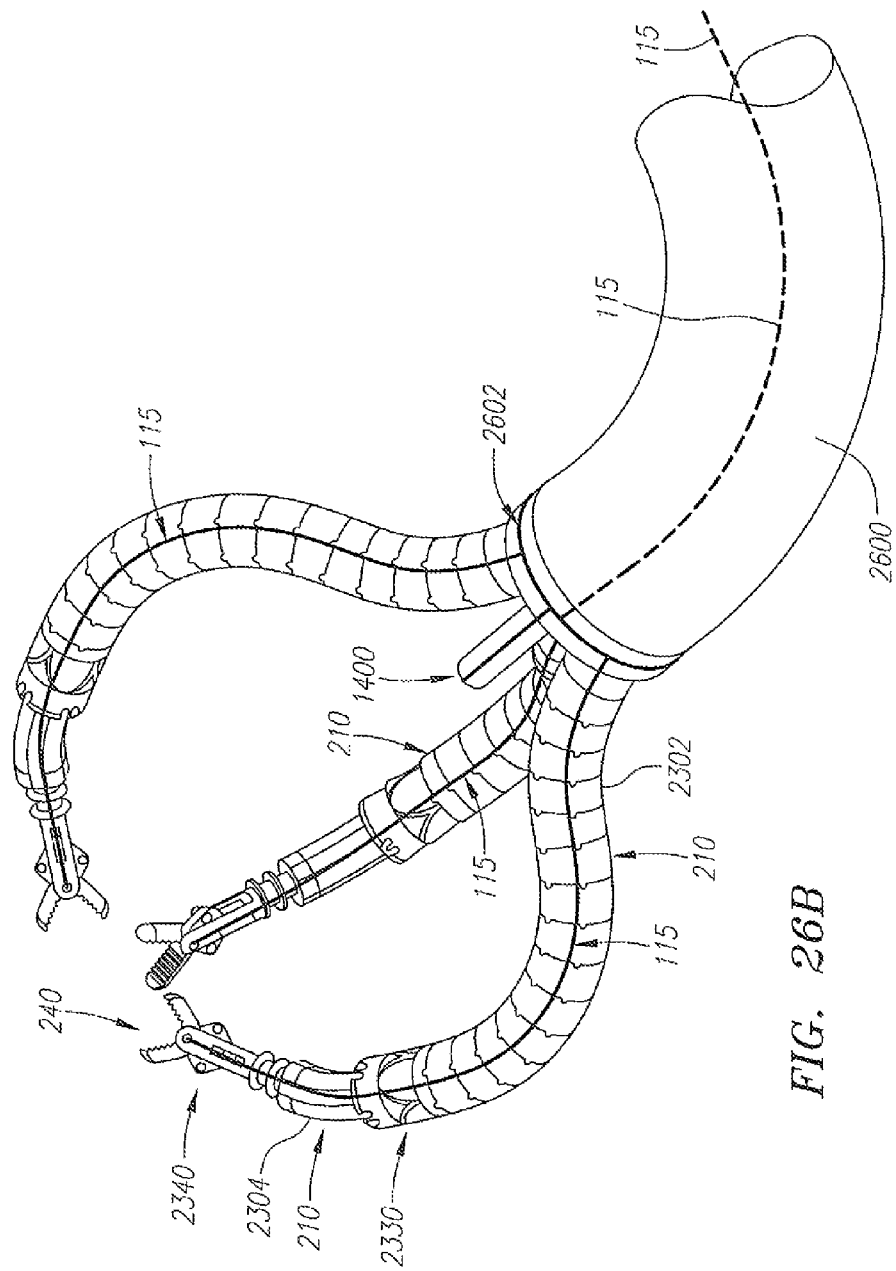

Further, as shown in FIGS. 26A-B, a common reference device, or "control ring" 2602 is provided at the distal end of the master sheath 2600 or sheath like structure that carries the elongate instruments including sheath catheters 2302 and guide catheters 2304. This control ring 2602 can be used as a common reference for all the fibers 115 on elongate instruments, image capture devices, and the like which may extend distally from the control ring 2602 location. This common reference establishes a common coordinate frame for all the fibers 115 such that the shape and location of the fibers 115 may be measured in relation to the control ring 2602. This arrangement is particularly advantageous because the accuracy at the tip will be high due to the short length of the fiber 115 run, the twist and roll of the elongate instruments may result in smaller errors since the distance between the control ring 2602 and the tip is short, and the elongate instruments are all in the same coordinate frame, which also improves accuracy compared to use of different coordinate frames.

The location of the control ring 2602 may be localized in the world coordinate system by a separate fiber 115 (single or multiple core), which is helpful if elongate instruments, such as catheters 2302, 2304, image capture device platforms, and the like, which extend distally beyond the control ring 2602, are coordinated with other external medical imaging or data processing systems, such as fluoroscopy systems, magnetic resonance imaging systems, or geometric and/or electronic mappings and datasets.

For embodiments in which multiple elongate instruments 2302 and/or 2304 carry single tools, a single elongate instrument carries multiple tools, or multiple elongate instruments each carry multiple tools, fiber based shape and location measurement devices 115 may be mechanically associated with each tool or each elongate instrument or to both. It is not necessary that all tools or elongate instruments have a fiber 115 attached or coupled thereto. Each fiber 115 could be a single core Bragg grating sensor fiber or a multiple core fiber Bragg grating sensor. More than one fiber may be used per tool or per elongate instrument or catheter.

Accordingly, FIGS. 23A-C and 26A-B are provided to illustrate different ways embodiments can be implemented. It should be understood that an instrument may include other numbers of sheath catheters 2302, other numbers of guide catheters 2304, and that each catheter 110 having an optical fiber sensor 115 coupled thereto may have fibers of various lengths, positions and configurations.

Additionally, embodiments described above can be utilized with various manually or robotically steerable instruments, various localization systems and rendering of images to assist an operator, including those systems and methods described in the aforementioned patent application, U.S. application Ser. No. 11/637,951, the contents of which were previously incorporated herein by reference. FIGS. 27-43 are provided for reference and illustrate one example of a localization system that utilizes localization data for closed-loop control of a robotic catheter system in which embodiments of the invention may be implemented, and FIGS. 44-49 are provided for reference and illustrate one example of user interface presentation of captured or "cartoon" rendered images that are used to assist the operator in controlling a robotic catheter system or the like. Additional details regarding these systems are omitted for clarity and described in further detail in application Ser. No. 11/637,951. Embodiments may also utilize other known localization and user interface presentation systems, and the systems and related methods shown in FIGS. 27-43 are provided as illustrative examples that may be used with embodiments.

FIGS. 27-37 depict various aspects of one embodiment of a SimuLink® software control schema for an embodiment of a physical system, with particular attention to an embodiment of a "master following mode." In this system, an instrument is driven by following instructions from a MID, and a motor servo loop embodiment, which comprises key operational functionality for executing upon commands delivered from the master following mode to actuate the instrument.

Figure 27:
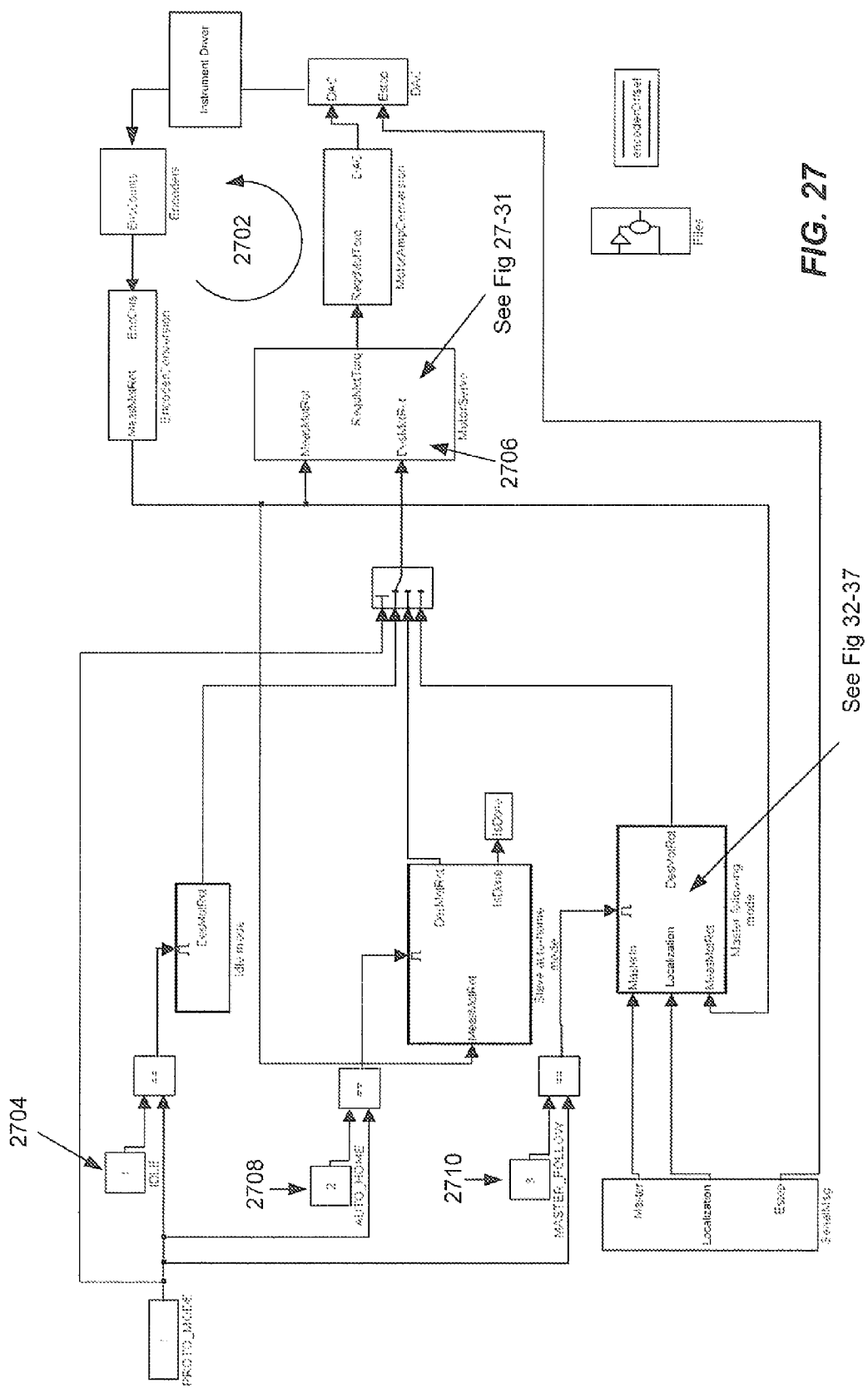
FIGS. 27-43 illustrate various aspects of a control schema, kinematics, actuation coordinates for kinematics, a block diagram of a system including a master input device, and a sample flowchart of transforming a position vector to a haptic signal, and a block diagram of a system including haptics capability of robotic surgical systems in which embodiments of the invention may be implemented.

FIG. 27 depicts a high-level view of an embodiment wherein any one of three modes may be toggled to operate the primary servo loop 2702. In idle mode 2704, the default mode when the system is started up, all of the motors are commanded via the motor servo block 2706 to servo about their current positions, their positions being monitored with digital encoders associated with the motors. In other words, idle mode 2704 deactivates the motors, while the remaining system stays active. Thus, when the operator leaves idle mode, the system knows the position of the relative components. In auto home mode 2708, cable loops within an associated instrument driver, such as the instrument driver 2220, are centered within their cable loop range to ensure substantially equivalent range of motion of an associated instrument, such as a catheter, in both directions for a various degree of freedom, such as + and −directions of pitch or yaw, when loaded upon the instrument driver. This is a setup mode for preparing an instrument driver before an instrument is engaged.

In master following mode 2710, the control system receives signals from the master input device, and in a closed loop embodiment from both a master input device and a localization system, and forwards drive signals to the primary servo loop 2702 to actuate the instrument in accordance with the forwarded commands. Aspects of this embodiment of the master following mode 2710 are depicted in further detail in FIGS. 32-37. Aspects of the primary servo loop and motor servo block 2706 are depicted in further detail in FIGS. 28-31.

Figure 32:
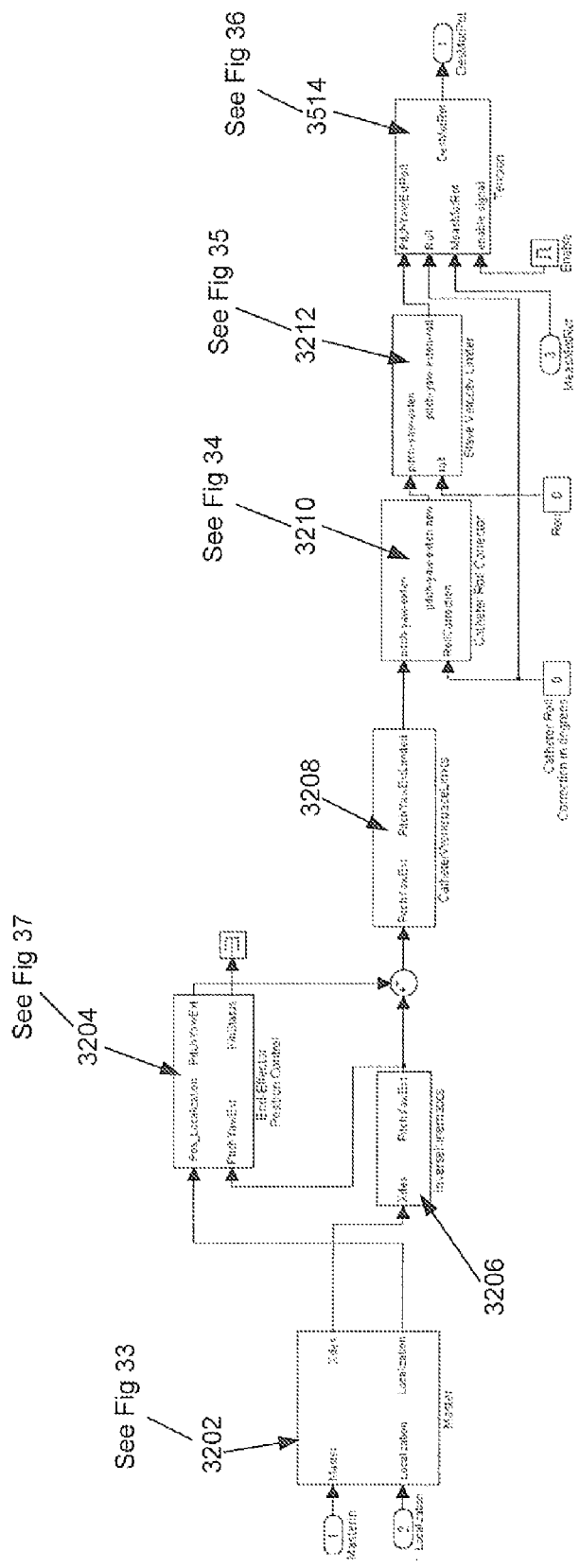
Figure 33:
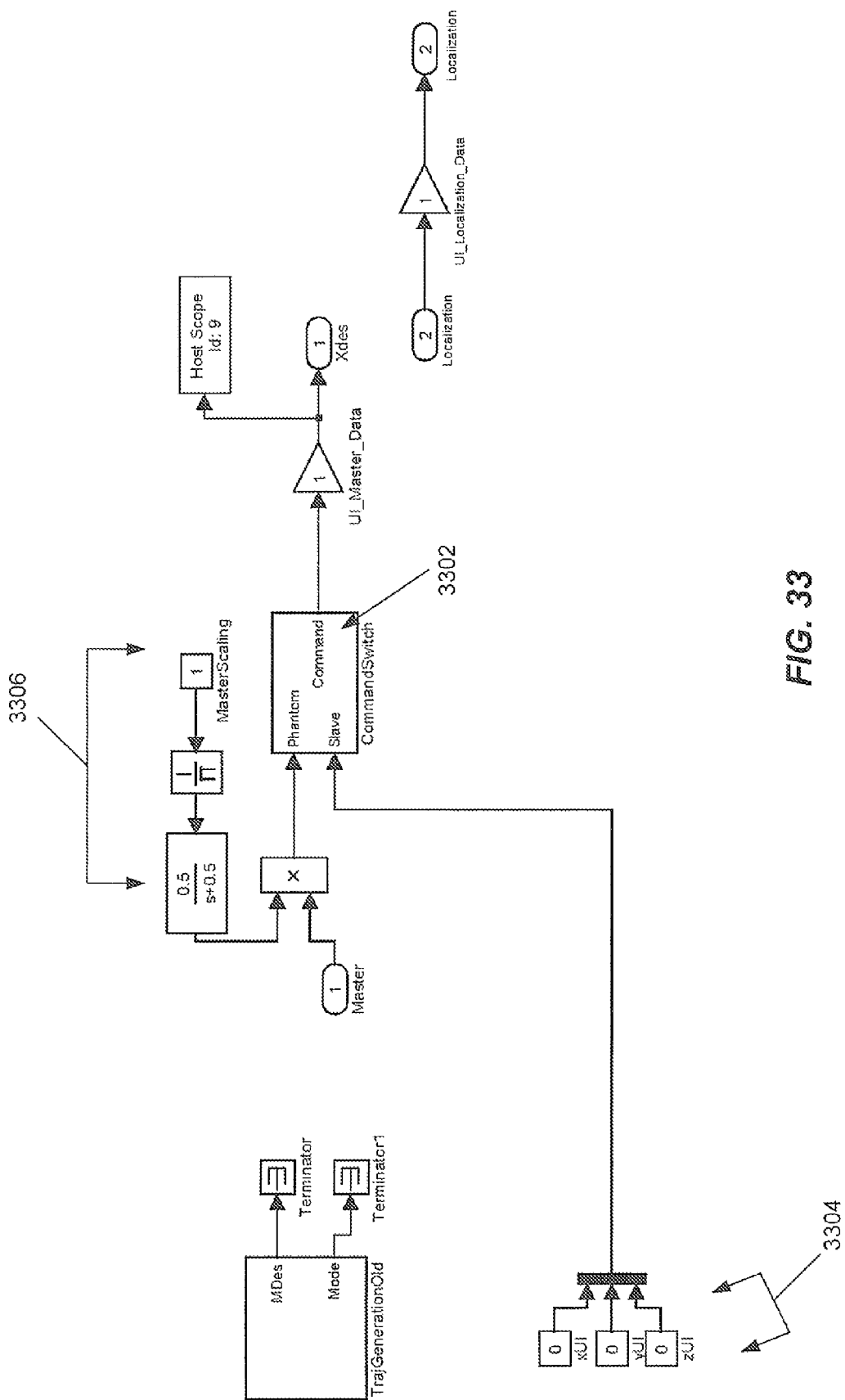

Referring to FIG. 32, a more detailed functional diagram of an embodiment of master following mode 2710 is depicted. As shown in FIG. 32, the inputs to functional block 3202 are XYZ position of the master input device in the coordinate system of the master input device which, per a setting in the software of the master input device may be aligned to have the same coordinate system as the catheter, and localization XYZ position of the distal tip of the instrument as measured by the localization system in the same coordinate system as the master input device and catheter. Referring to FIG. 33, for a more detailed view of functional block 3202 of FIG. 32, a switch 3302 is provided at block to allow switching between master inputs for desired catheter position, to an input interface 3304 through which an operator may command that the instrument go to a particular XYZ location in space. Various controls features may also utilize this interface to provide an operator with, for example, a menu of destinations to which the system should automatically drive an instrument, etc. Also depicted in FIG. 33 is a master scaling functional block 3306 which is utilized to scale the inputs coming from the master input device with a ratio selectable by the operator. The command switch 3302 functionality includes a low pass filter to weight commands switching between the master input device and the input interface 3304, to ensure a smooth transition between these modes.

Referring back to FIG. 32, desired position data in XYZ terms is passed to the inverse kinematics block 3206 for conversion to pitch, yaw, and extension (or "insertion") terms in accordance with the predicted mechanics of materials relationships inherent in the mechanical design of the instrument.

The kinematic relationships for many catheter instrument embodiments may be modeled by applying conventional mechanics relationships. In summary, a control-element-steered catheter instrument is controlled through a set of actuated inputs. In a four-control-element catheter instrument, for example, there are two degrees of motion actuation, pitch and yaw, which both have + and −directions. Other motorized tension relationships may drive other instruments, active tensioning, or insertion or roll of the catheter instrument. The relationship t, between actuated inputs and the catheter's end point position as a function of the actuated inputs is referred to as the "kinematics" of the catheter.

Figure 38:
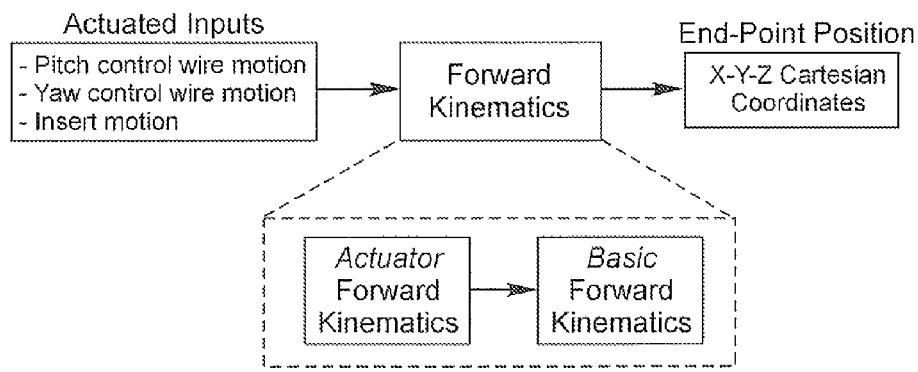
Figure 38:
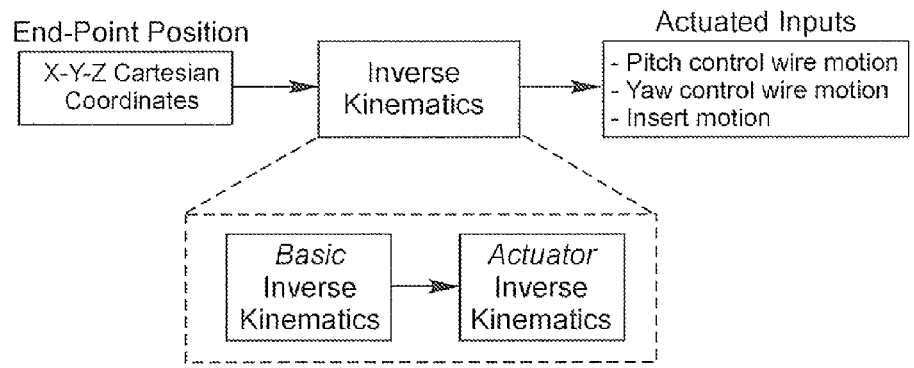
Figure 39:
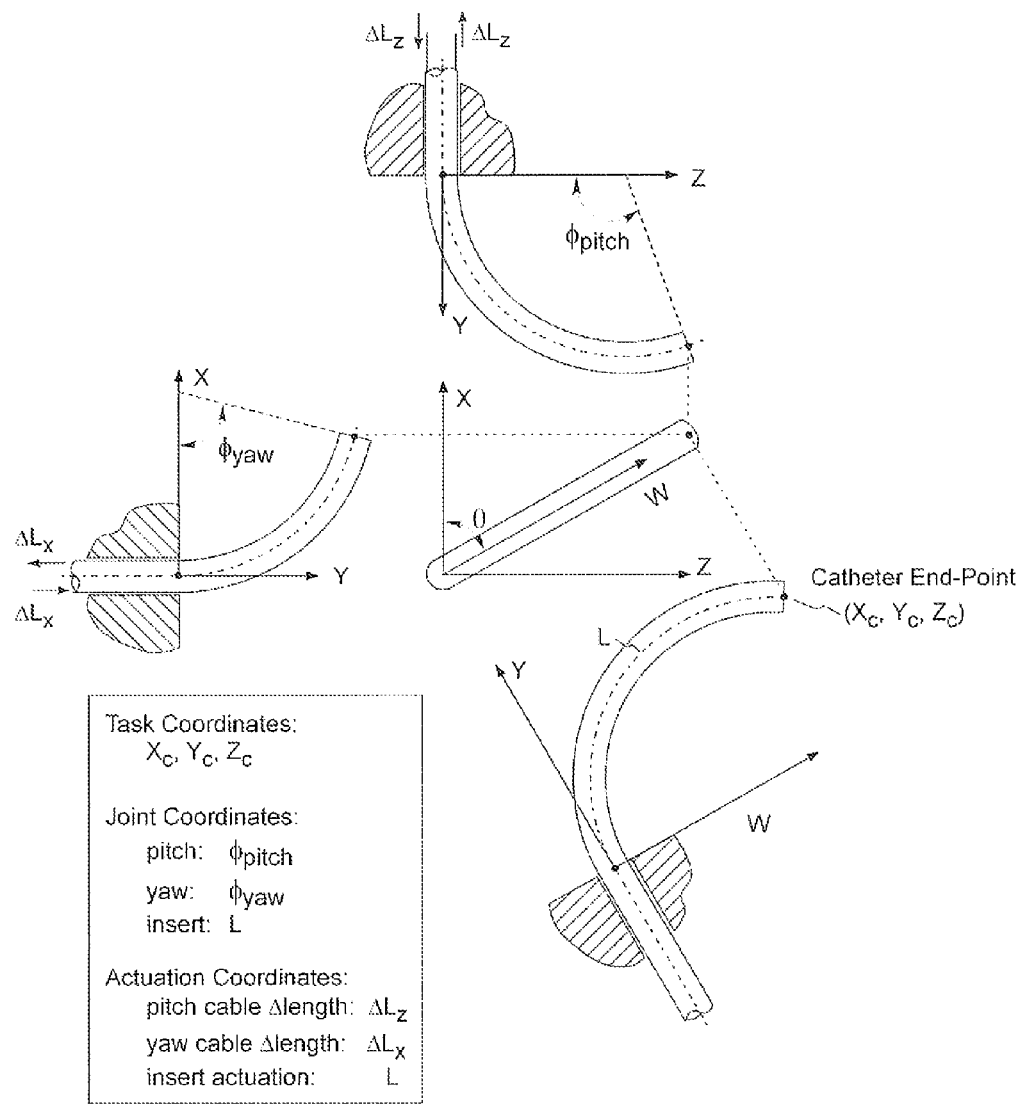

Referring to FIG. 38, the "forward kinematics" expresses the catheter's end-point position as a function of the actuated inputs while the "inverse kinematics" expresses the actuated inputs as a function of the desired end-point position. Accurate mathematical models of the forward and inverse kinematics are essential for the control of a robotically controlled catheter system. For clarity, the kinematics equations are further refined to separate out common elements, as shown in FIG. 38. The basic kinematics describes the relationship between the task coordinates and the joint coordinates. In such case, the task coordinates refer to the position of the catheter end-point while the joint coordinates refer to the bending (pitch and yaw, for example) and length of the active catheter. The actuator kinematics describes the relationship between the actuation coordinates and the joint coordinates. The task, joint, and bending actuation coordinates for the robotic catheter are illustrated in FIG. 39. By describing the kinematics in this way we can separate out the kinematics associated with the catheter structure, namely the basic kinematics, from those associated with the actuation methodology.

The development of the catheter's kinematics model is derived using a few essential assumptions. Included are assumptions that the catheter structure is approximated as a simple beam in bending from a mechanics perspective, and that control elements, such as thin tension wires, remain at a fixed distance from the neutral axis and thus impart a uniform moment along the length of the catheter.

In addition to the above assumptions, the geometry and variables shown in FIG. 40 are used in the derivation of the forward and inverse kinematics. The basic forward kinematics relates catheter task coordinates to joint coordinates, as explained in further detail in U.S. application Ser. No. 11/637, 951. The actuator forward kinematics, relating the joint coordinates to the actuator coordinates are also explained in application Ser. No. 11/637,951

As illustrated in FIG. 38, the catheter's end-point position can be predicted given the joint or actuation coordinates by using the forward kinematics equations described above. Calculation of the catheter's actuated inputs as a function of end-point position, referred to as the inverse kinematics, can be performed numerically, using a nonlinear equation solver such as Newton-Raphson. A more desirable approach, and the one used in this illustrative embodiment, is to develop a closed-form solution which can be used to calculate the required actuated inputs directly from the desired end-point positions.

As with the forward kinematics, the inverse kinematics are separated into the basic inverse kinematics, which relates joint coordinates to the task coordinates, and the actuation inverse kinematics, which relates the actuation coordinates to the joint coordinates. The basic inverse kinematics, relating the joint coordinates to the catheter task coordinates is explained in application Ser. No. 11/637,951. The actuator inverse kinematics, relating the actuator coordinates to the joint coordinates is also explained in application Ser. No. 11/637,951.

Figure 37:
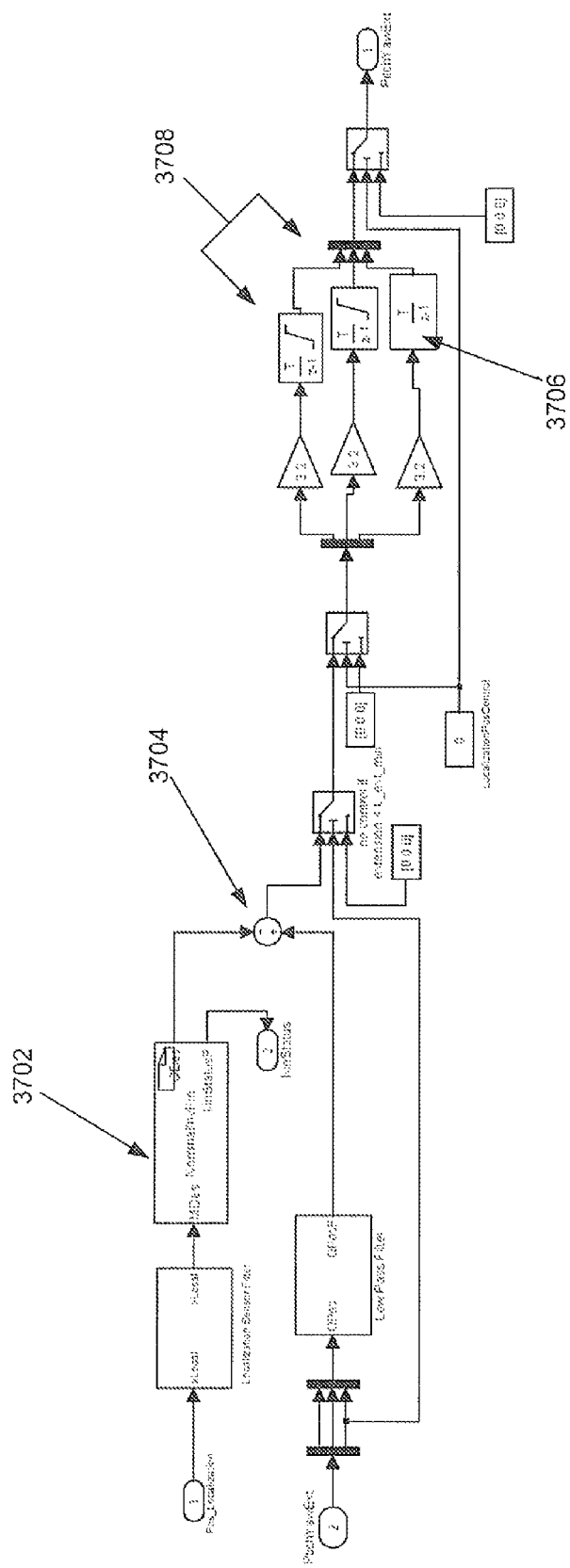

Referring back to FIG. 32, pitch, yaw, and extension commands are passed from the inverse kinematics block 3206 to a position control block 3204 along with measured localization data. FIG. 37 provides a more detailed view of the position control block 3204. After measured XYZ position data comes in from the localization system, it goes through a inverse kinematics block 3702 to calculate the pitch, yaw, and extension the instrument needs to have in order to travel to where it needs to be. Comparing 3704 these values with filtered desired pitch, yaw, and extension data from the master input device, integral compensation is then conducted with limits on pitch and yaw to integrate away the error. In this embodiment, the extension variable does not have the same limits 3706, as do pitch and yaw 3708. As will be apparent to those skilled in the art, having an integrator in a negative feedback loop forces the error to zero. Desired pitch, yaw, and extension commands are next passed through a catheter workspace limitation block 3208, which may be a function of the experimentally determined physical limits of the instrument beyond which componentry may fail, deform undesirably, or perform unpredictably or undesirably. This workspace limitation essentially defines a volume similar to a cardioid-shaped volume about the distal end of the instrument. Desired pitch, yaw, and extension commands, limited by the workspace limitation block, are then passed to a catheter roll correction block 3210.

Figure 34:
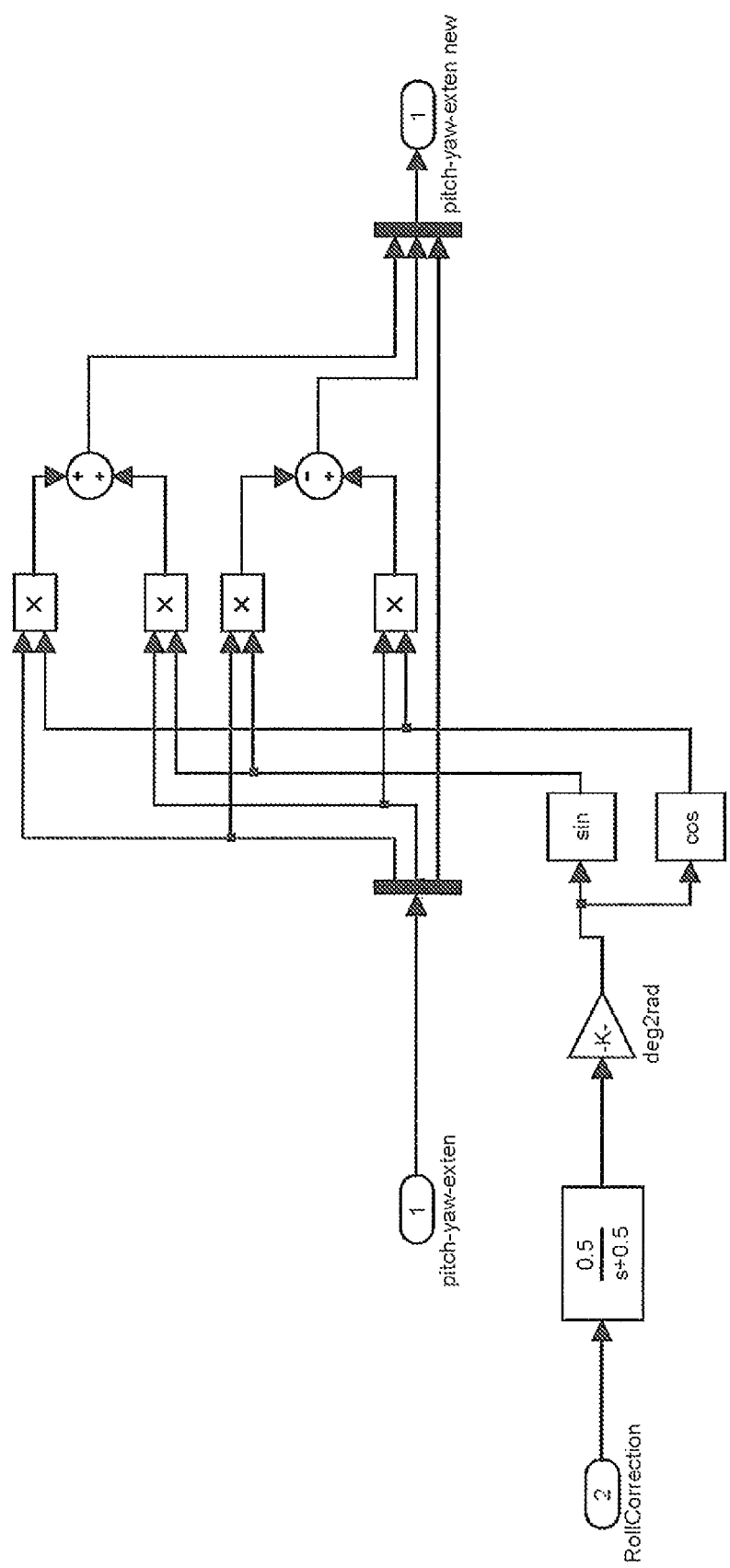

This functional block is depicted in further detail in FIG. 34, and essentially comprises a rotation matrix for transforming the pitch, yaw, and extension commands about the longitudinal, or "roll", axis of the instrument—to calibrate the control system for rotational deflection at the distal tip of the catheter that may change the control element steering dynamics. For example, if a catheter has no rotational deflection, pulling on a control element located directly up at twelve o'clock should urge the distal tip of the instrument upward. If, however, the distal tip of the catheter has been rotationally deflected by, say, ninety degrees clockwise, to get an upward response from the catheter, it may be necessary to tension the control element that was originally positioned at a nine o'clock position. The catheter roll correction schema depicted in FIG. 34 provides a means for using a rotation matrix to make such a transformation, subject to a roll correction angle, such as the ninety degrees in the above example, which is input, passed through a low pass filter, turned to radians, and put through rotation matrix calculations.

In one embodiment, the roll correction angle is determined through experimental experience with a particular instrument and path of navigation. In another embodiment, the roll correction angle may be determined experimentally in-situ using the accurate orientation data available from the preferred localization systems. In other words, with such an embodiment, a command to, for example, bend straight up can be executed, and a localization system can be utilized to determine at which angle the defection actually went—to simply determine the in-situ roll correction angle.

Figure 35:
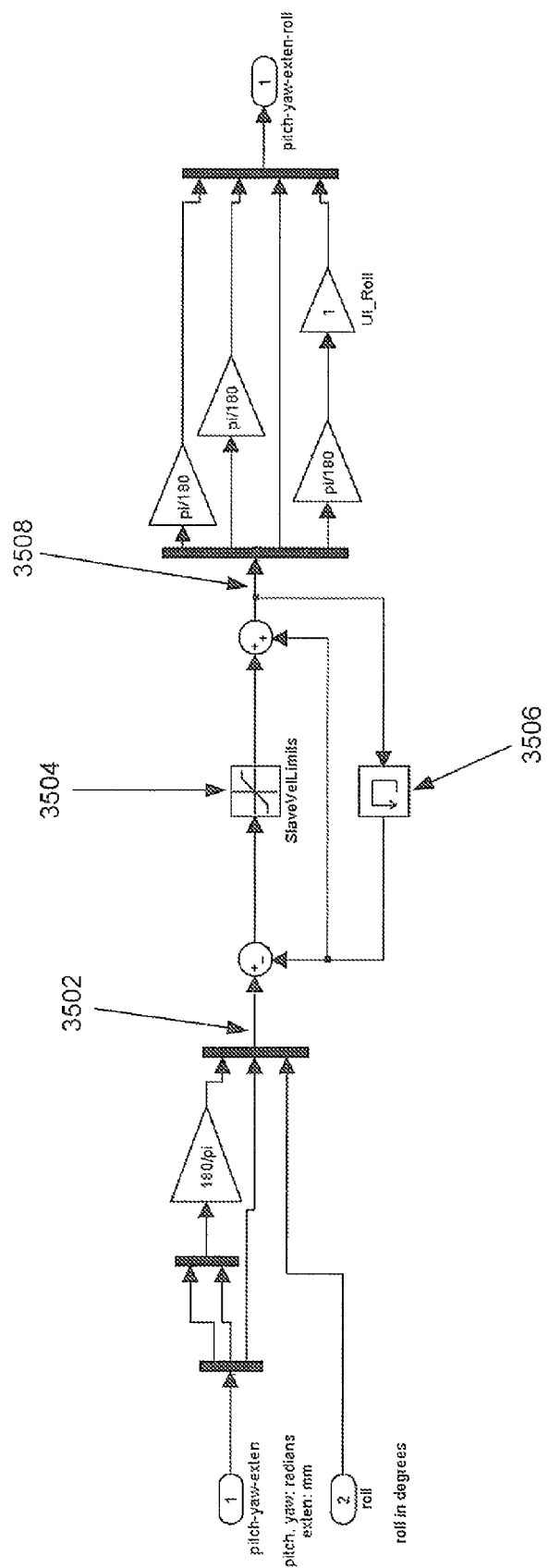

Referring briefly back to FIG. 32, roll corrected pitch and yaw commands, as well as unaffected extension commands, are output from the catheter roll correction block 3210 and may optionally be passed to a conventional velocity limitation block 3212. Referring to FIG. 35, pitch and yaw commands are converted from radians to degrees, and automatically controlled roll may enter the controls picture to complete the current desired position 3502 from the last servo cycle. Velocity is calculated by comparing the desired position from the previous servo cycle, as calculated with a conventional memory block calculation 3506, with that of the incoming commanded cycle. A conventional saturation block 3504 keeps the calculated velocity within specified values, and the velocity-limited command 3508 is converted back to radians and passed to a tension control block.

Figure 36:
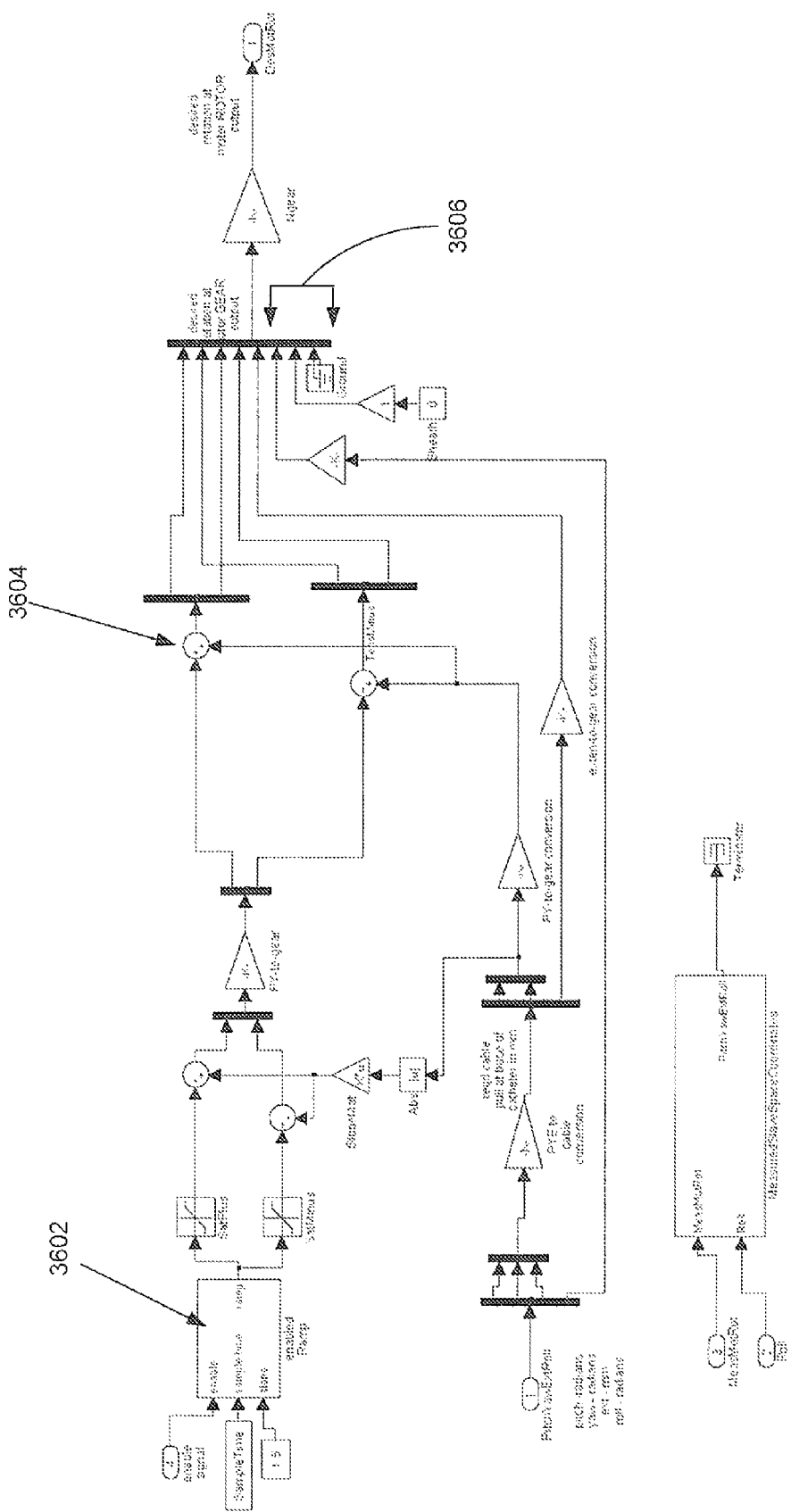

Tension within control elements may be managed depending upon the particular instrument embodiment, as described above in reference to the various instrument embodiments and tension control mechanisms. As an example, FIG. 36 depicts a pre-tensioning block 3602 with which a given control element tension is ramped to a present value. An adjustment is then added to the original pre-tensioning based upon a preferably experimentally-tuned matrix pertinent to variables, such as the failure limits of the instrument construct and the incoming velocity-limited pitch, yaw, extension, and roll commands. This adjusted value is then added 3604 to the original signal for output, via gear ratio adjustment, to calculate desired motor rotation commands for the various motors involved with the instrument movement. In this embodiment, extension, roll, and sheath instrument actuation 3606 have no pre-tensioning algorithms associated with their control. The output is then complete from the master following mode functionality, and this output is passed to the primary servo loop 2702.

Referring back to FIG. 27, incoming desired motor rotation commands from either the master following mode 2710, auto home mode 2708, or idle mode 2704 in the depicted embodiment are fed into a motor servo block 2706, which is depicted in greater detail in FIGS. 28-31.

Figure 28:
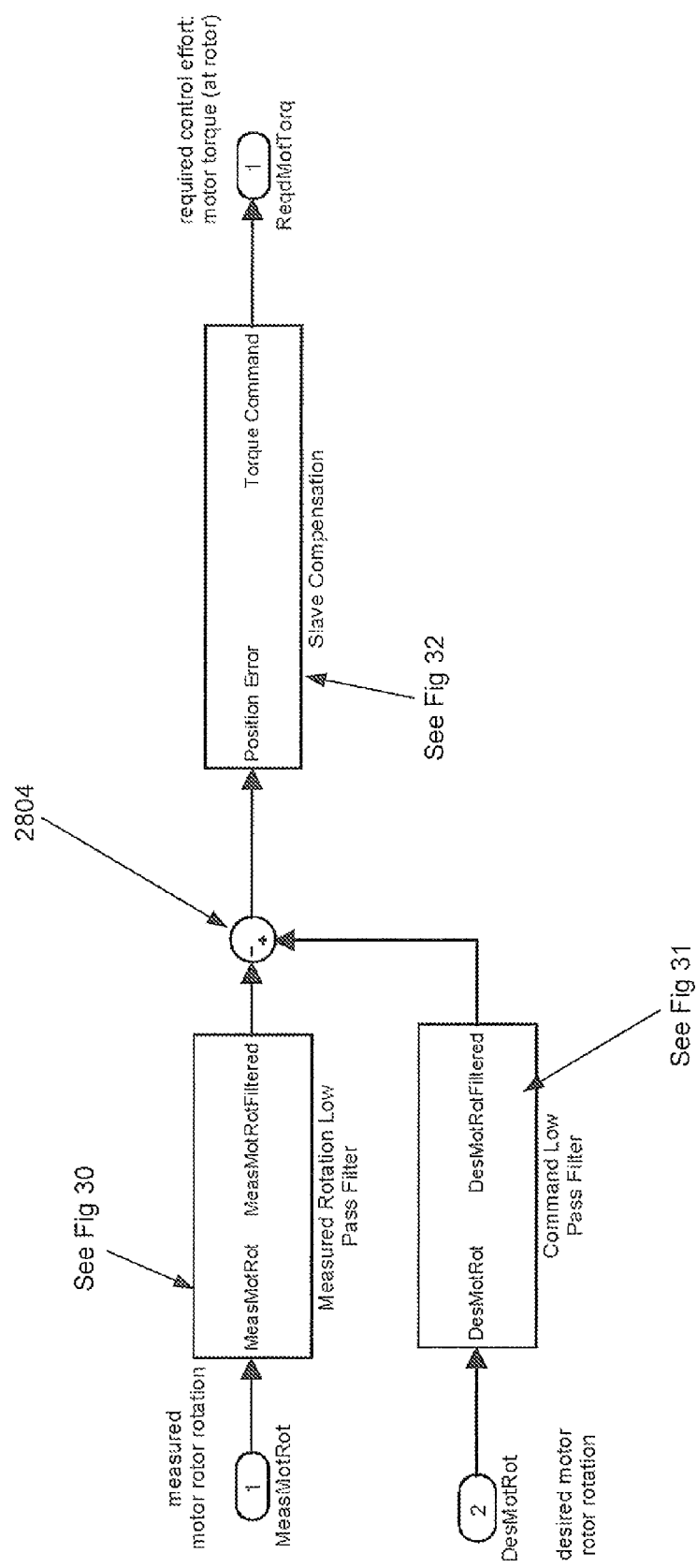
Figure 30:
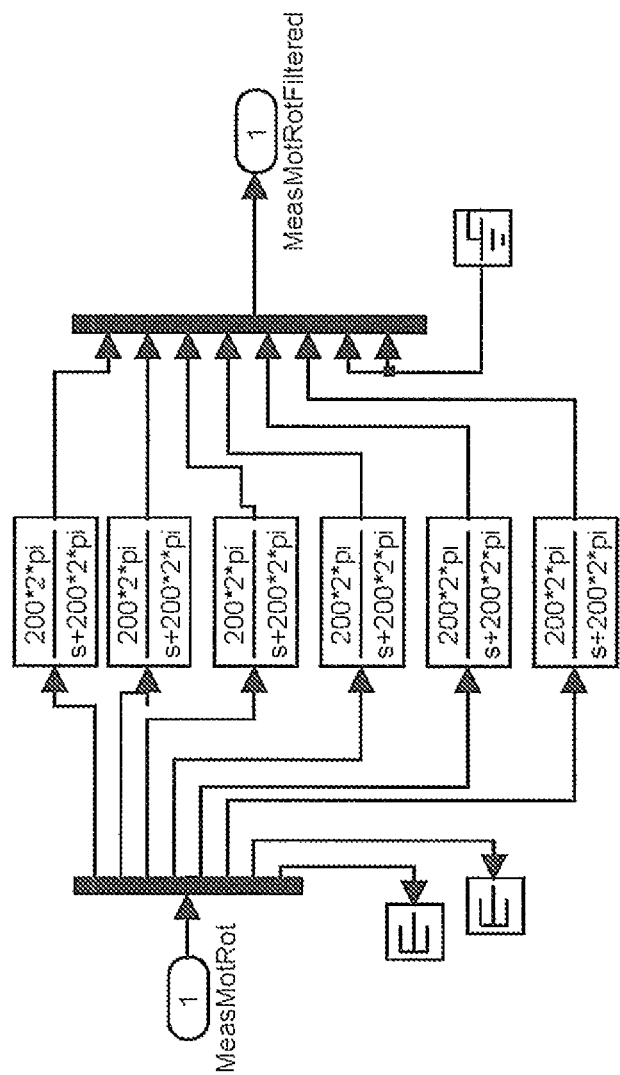
Figure 31:
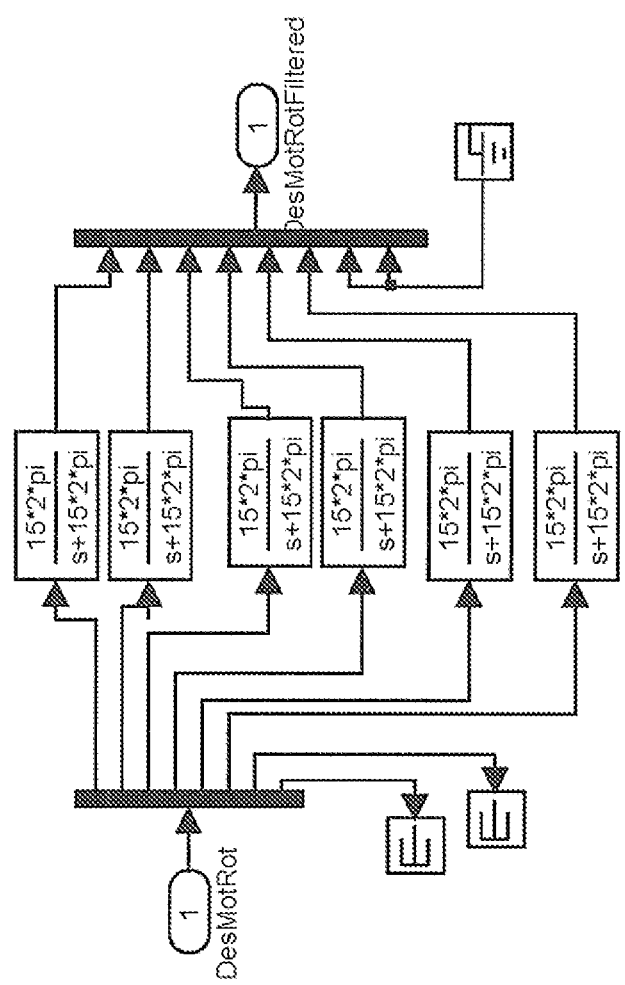

Referring to FIG. 28, incoming measured motor rotation data from digital encoders and incoming desired motor rotation commands are filtered using conventional quantization noise filtration at frequencies selected for each of the incoming data streams to reduce noise while not adding undue delays which may affect the stability of the control system. As shown in FIGS. 30-31, conventional quantization filtration is utilized on the measured motor rotation signals at about 200 hertz in this embodiment, and on the desired motor rotation command at about 15 hertz. The difference 2804 between the quantization filtered values forms the position error which may be passed through a lead filter, the functional equivalent of a proportional derivative ("PD")+low pass filter. In another embodiment, conventional PID, lead/lag, or state space representation filter may be utilized. The lead filter of the depicted embodiment is shown in further detail in FIG. 29.

Figure 29:
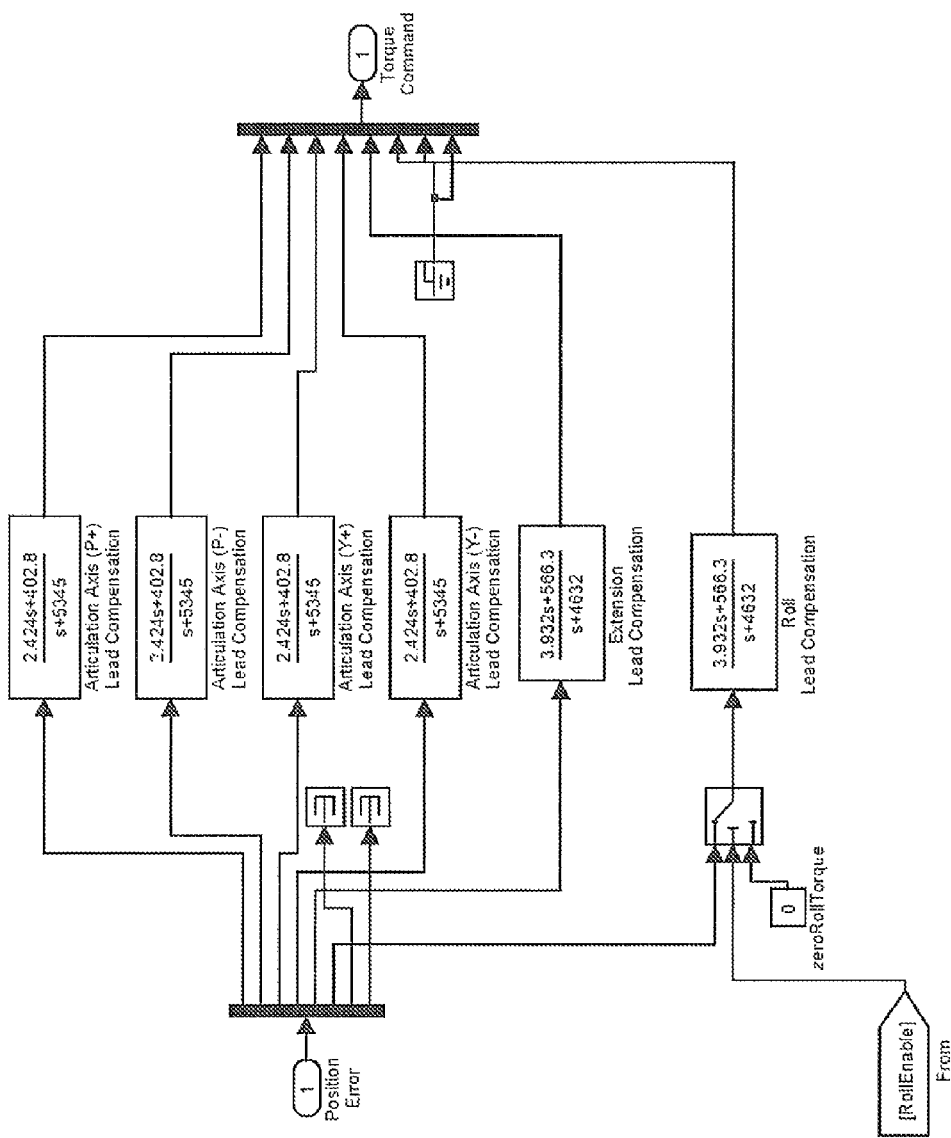

In particular, the lead filter embodiment in FIG. 29 comprises a variety of constants selected to tune the system to achieve desired performance. The depicted filter addresses the needs of one embodiment of a 4-control element guide catheter instrument with independent control of each of four control element interface assemblies for +/−pitch and +/−yaw, and separate roll and extension control. As demonstrated in the depicted embodiment, insertion and roll have different inertia and dynamics as opposed to pitch and yaw controls, and the constants selected to tune them is different. The filter constants may be theoretically calculated using conventional techniques and tuned by experimental techniques, or wholly determined by experimental techniques, such as setting the constants to give a sixty degree or more phase margin for stability and speed of response, a conventional phase margin value for medical control systems.

In an embodiment where a tuned master following mode is paired with a tuned primary servo loop, an instrument and instrument driver, such as those described above, may be "driven" accurately in three-dimensions with a remotely located master input device. Other preferred embodiments incorporate related functionalities, such as haptic feedback to the operator, active tensioning with a split carriage instrument driver, navigation utilizing direct visualization and/or tissue models acquired in-situ and tissue contact sensing, and enhanced navigation logic.

Referring to FIG. 39, in one embodiment, the master input device may be a haptic master input device, such as those available from SensAble Technologies, Inc., under the trade name Phantom® Haptic Devices, and the hardware and software required for operating such a device may at least partially reside on the master computer. The master XYZ positions measured from the master joint rotations and forward kinematics are generally passed to the master computer via a parallel port or similar link and may subsequently be passed to a control and instrument driver computer. With such an embodiment, an internal servo loop for a Phantoms® Haptic Device generally runs at a much higher frequency in the range of 1,000 Hz, or greater, to accurately create forces and torques at the joints of the master.

Figure 42:
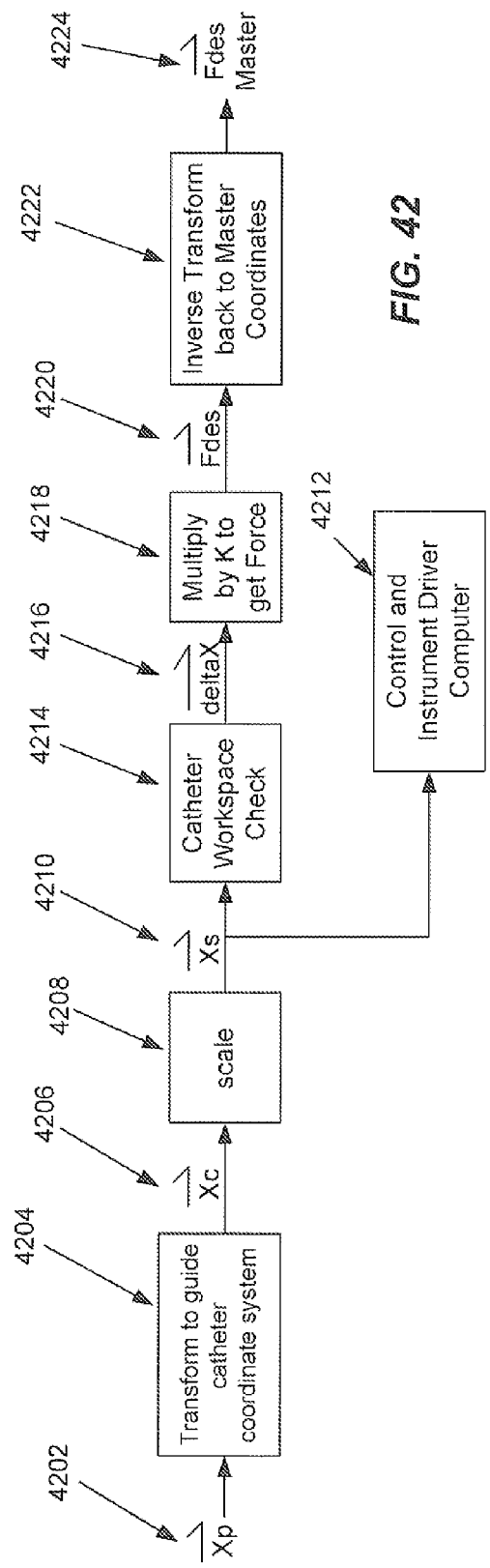

Referring to FIG. 42, a sample flowchart of a series of operations leading from a position vector applied at the master input device to a haptic signal applied back at the operator is depicted. A vector 4202 associated with a master input device move by an operator may be transformed into an instrument coordinate system, and in particular to a catheter instrument tip coordinate system, using a simple matrix transformation 4204. The transformed vector 4206 may then be scaled 4208 per the preferences of the operator, to produce a scaled-transformed vector 4210. The scaled-transformed vector may be sent to both the control and instrument driver computer 4212 preferably via a serial wired connection, and to the master computer for a catheter workspace check 4214 and any associated vector modification 4216. This is followed by a feedback constant multiplication 4218 chosen to produce preferred levels of feedback, such as force, in order to produce a desired force vector 4220, and an inverse transform 4222 back to a force vector 4224 in the master input device coordinate system for associated haptic signaling to the operator in that coordinate system.

A conventional Jacobian may be utilized to convert a desired force vector 4220 to torques desirably applied at the various motors comprising the master input device, to give the operator a desired signal pattern at the master input device. Given this embodiment of a suitable signal and execution pathway, feedback to the operator in the form of haptics, or touch sensations, may be utilized in various ways to provide added safety and instinctiveness to the navigation features of the system, as discussed in further detail below.

Figure 43:
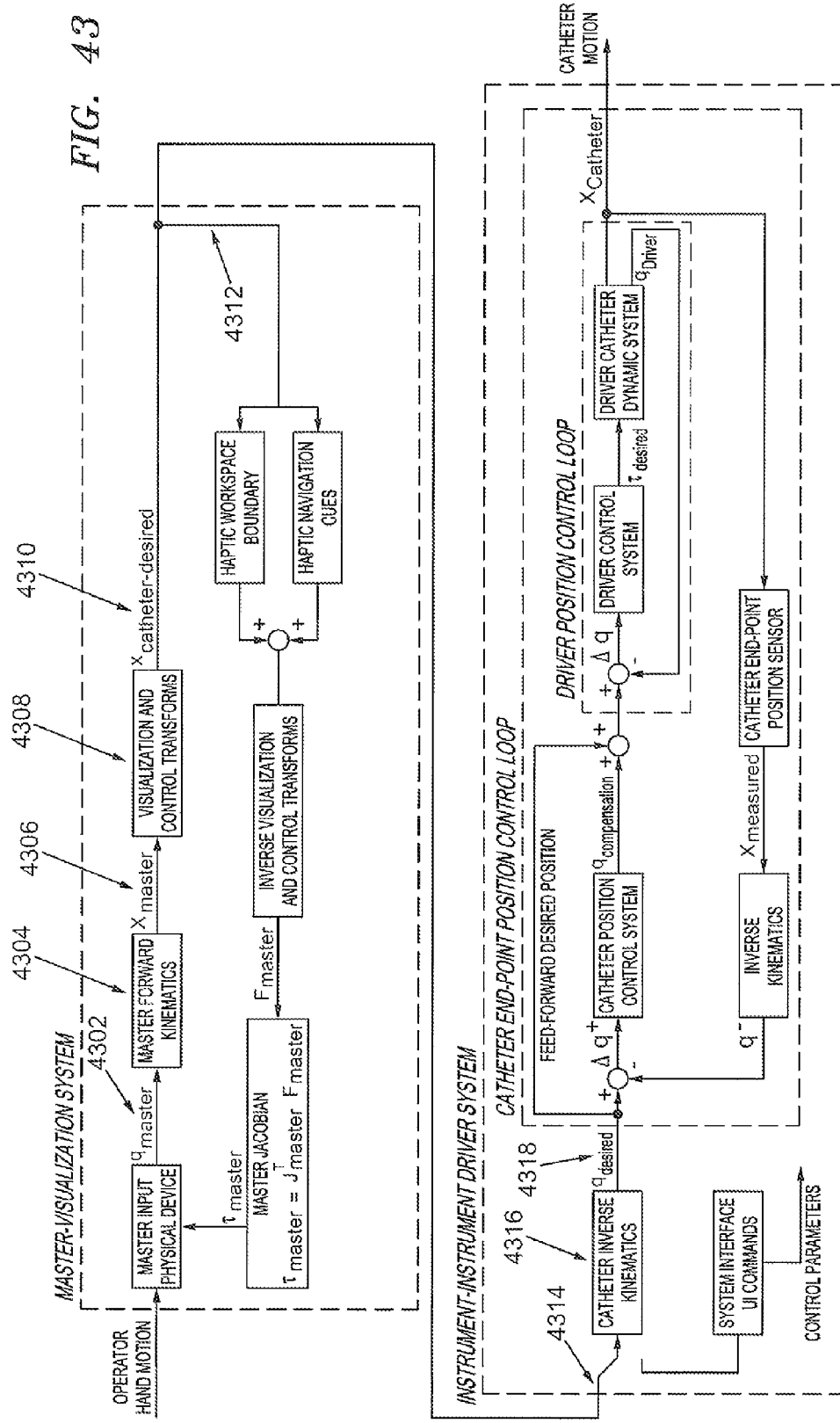

FIG. 43 is a system block diagram including haptics capability. As shown in summary form in FIG. 43, encoder positions on the master input device, changing in response to motion at the master input device, are measured 4302, sent through forward kinematics calculations 4304 pertinent to the master input device to get XYZ spatial positions of the device in the master input device coordinate system 4306, then transformed 4308 to switch into the catheter coordinate system and (perhaps) transform for visualization orientation and preferred controls orientation, to facilitate "instinctive driving".

The transformed desired instrument position 4310 may then be sent down one or more controls pathways to, for example, provide haptic feedback 4312 regarding workspace boundaries or navigation issues, and provide a catheter instrument position control loop 4314 with requisite catheter desired position values, as transformed utilizing catheter inverse 4316 kinematics relationships for the particular instrument into yaw, pitch, and extension, or insertion, terms 4318 pertinent to operating the particular catheter instrument with open or closed loop control.

Figure 44:
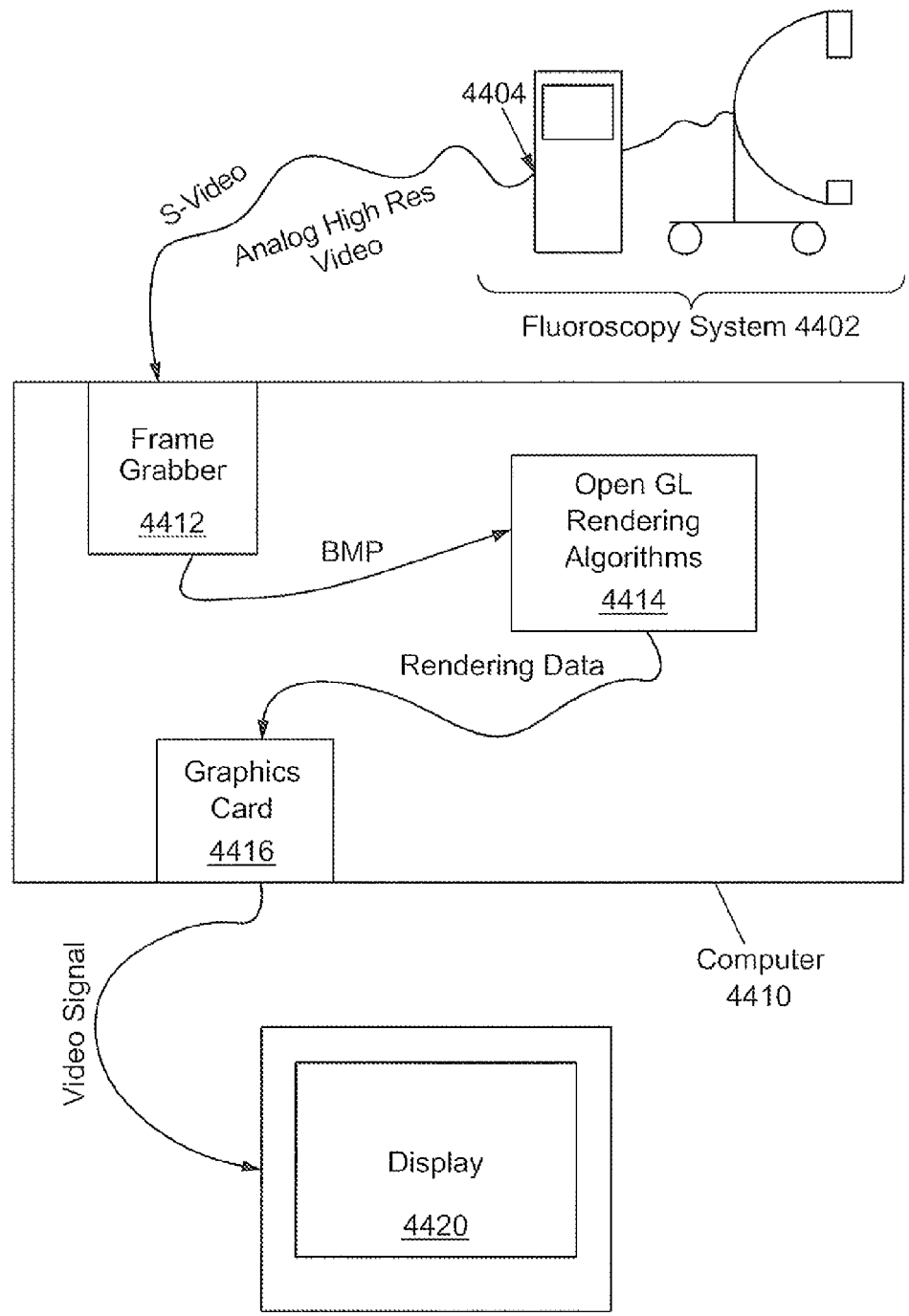
FIGS. 44-49 are provided for reference to illustrate examples of a system block diagram, a system configuration for visualization of tissue by overlaying images, a schematic for overlaying objects to the display, a distributed system architecture and hardware and software interfaces of robotic surgical systems in which embodiments may be implemented.

As further reference, referring to FIG. 44, a systemic view configured to produce an overlaid image is depicted. A known fluoroscopy system 4402 outputs an electronic image in formats such as those known as "S-video" or "analog high-resolution video". In image output interface 4404 of a fluoroscopy system 4402 may be connected to an input interface of a computer 4410 based image acquisition device, such as those known as "frame grabber" 4412 image acquisition cards, to facilitate intake of the video signal from the fluoroscopy system 4402 into the frame grabber 4412, which may be configured to produce bitmap ("BMP") digital image data, generally comprising a series of Cartesian pixel coordinates and associated grayscale or color values which together may be depicted as an image. The bitmap data may then be processed utilizing computer graphics rendering algorithms, such as those available in conventional OpenGL graphics libraries 4414. In summary, conventional OpenGL functionality enables a programmer or operator to define object positions, textures, sizes, lights, and cameras to produce three-dimensional renderings on a two-dimensional display. The process of building a scene, describing objects, lights, and camera position, and using OpenGL functionality to turn such a configuration into a two-dimensional image for display is known in computer graphics as rendering. The description of objects may be handled by forming a mesh of triangles, which conventional graphics cards are configured to interpret and output displayable two-dimensional images for a conventional display or computer monitor, as would be apparent to one skilled in the art. Thus the OpenGL software 4414 may be configured to send rendering data to the graphics card 4416, which may then be output to a conventional display 4420.

A triangular mesh generated with OpenGL software may be used to form a cartoon-like rendering of an elongate instrument moving in space according to movements from, for example, a master following mode operational state, may be directed to a computer graphics card, along with frame grabber and OpenGL processed fluoroscopic video data. Thus a moving cartoon-like image of an elongate instrument would be displayable. To project updated fluoroscopic image data onto a flat-appearing surface in the same display, a plane object, conventionally rendered by defining two triangles, may be created, and the updated fluoroscopic image data may be texture mapped onto the plane. Thus the cartoon-like image of the elongate instrument may be overlaid with the plane object upon which the updated fluoroscopic image data is texture mapped. Camera and light source positioning may be pre-selected, or selectable by the operator through the mouse or other input device, for example, to enable the operator to select desired image perspectives for his two-dimensional computer display. The perspectives, which may be defined as origin position and vector position of the camera, may be selected to match with standard views coming from a fluoroscopy system, such as anterior/posterior and lateral views of a patient lying on an operating table. When the elongate instrument is visible in the fluoroscopy images, the fluoroscopy plane object and cartoon instrument object may be registered with each other by ensuring that the instrument depicted in the fluoroscopy plane lines up with the cartoon version of the instrument. In one embodiment, several perspectives are viewed while the cartoon object is moved using an input device such as a mouse, until the cartoon instrument object is registered with the fluoroscopic plane image of the instrument. Because both the position of the cartoon object and fluoroscopic image object may be updated in real time, an operator, or the system automatically through image processing of the overlaid image, may interpret significant depicted mismatch between the position of the instrument cartoon and the instrument fluoroscopic image as contact with a structure that is inhibiting the normal predicted motion of the instrument, error or malfunction in the instrument, or error or malfunction in the predictive controls software underlying the depicted position of the instrument cartoon.

Referring back to FIG. 44, other video signals (not shown) may be directed to the image grabber 4412, besides that of a fluoroscopy system 4402, simultaneously. For example, images from an intracardiac echo ultrasound ("ICE") system, intravascular ultrasound ("IVUS"), or other system may be overlaid onto the same displayed image simultaneously. Further, additional objects besides a plane for texture mapping fluoroscopy or a elongate instrument cartoon object may be processed using OpenGL or other rendering software to add additional objects to the final display.

Figure 45A:
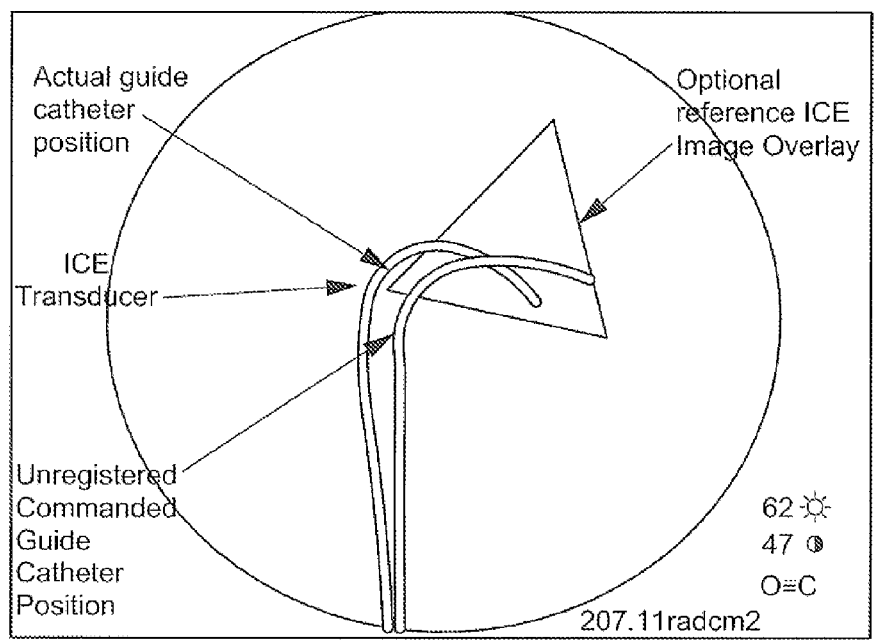
Figure 45B:
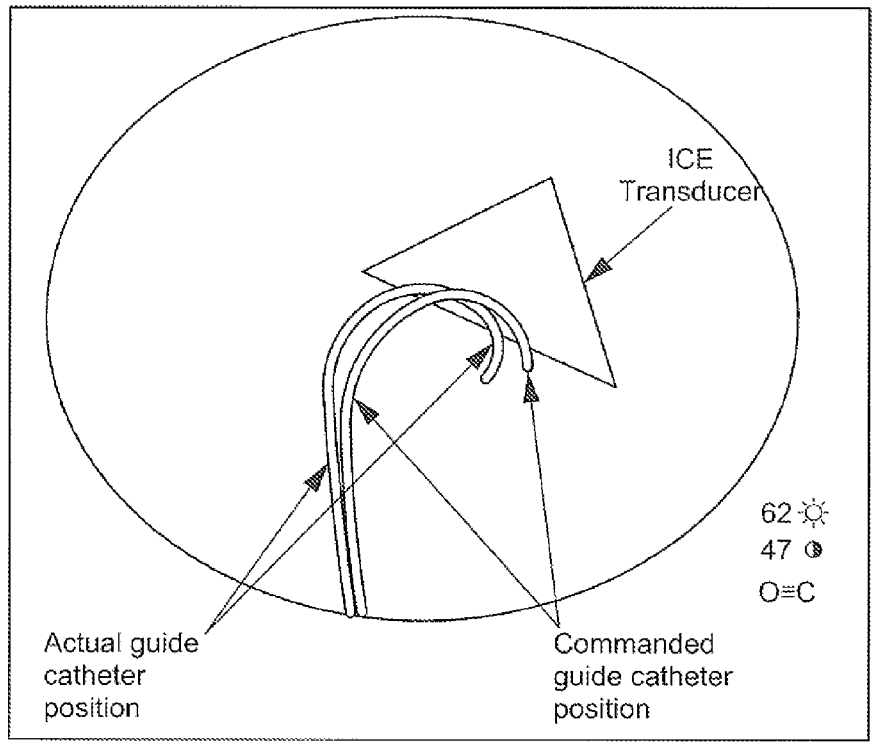
Figure 46:
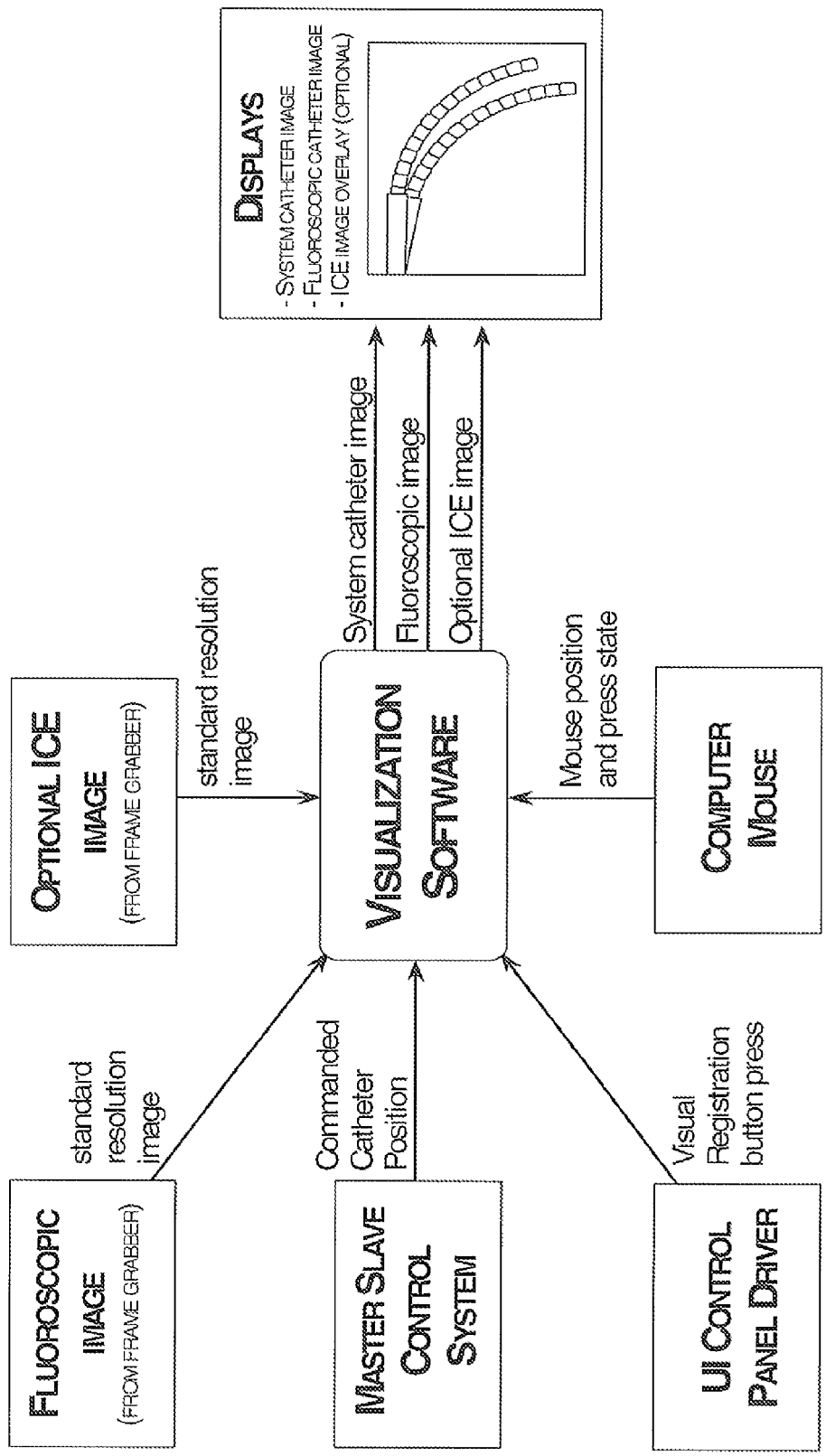

Referring to FIGS. 45A-B and 46, an elongate instrument is a robotic guide catheter, and fluoroscopy and ICE are utilized to visualize the cardiac and other surrounding tissues, and instrument objects. Referring to FIG. 45A, a fluoroscopy image has been texture mapped upon a plane configured to occupy nearly the entire display area in the background. Visible in the fluoroscopy image as a dark elongate shadow is the actual position, from fluoroscopy, of the guide catheter instrument relative to the surrounding tissues. Overlaid in front of the fluoroscopy plane is a cartoon rendering (white in color in FIGS. 45A-B) of the predicted, or "commanded", guide catheter instrument position. Further overlaid in front of the fluoroscopy plane is a small cartoon object representing the position of the ICE transducer, as well as another plane object adjacent the ICE transducer cartoon object onto which the ICE image data is texture mapped by a technique similar to that with which the fluoroscopic images are texture mapped upon the background plane object. Further, mouse objects, software menu objects, and many other objects may be overlaid. FIG. 45A shows a similar view with the instrument in a different position. For illustrative purposes, FIGS. 45A-B depict misalignment of the instrument position from the fluoroscopy object, as compared with the instrument position from the cartoon object. As described above, the various objects may be registered to each other by manually aligning cartoon objects with captured image objects in multiple views until the various objects are aligned as desired. Image processing of markers and shapes of various objects may be utilized to automate portions of such a registration process.

Referring to FIG. 46, a schematic is depicted to illustrate how various objects, originating from actual medical images processed by frame grabber, originating from commanded instrument position control outputs, or originating from computer operating system visual objects, such as mouse, menu, or control panel objects, may be overlaid into the same display.

Further, a pre-acquired image of pertinent tissue, such as a three-dimensional image of a heart, may be overlaid and registered to updated images from real-time medical imaging modalities as well. For example, in one embodiment, a beating heart may be preoperatively imaged using gated computed tomography (CT). The result of CT imaging may be a stack of CT data slices. Utilizing either manual or automated thresholding techniques, along with interpolation, smoothing, and/or other conventional image processing techniques available in software packages such as that sold under the tradename Amira™ product available from Mercury Computer Systems of Chelmsford, Mass., a triangular mesh may be constructed to represent a three-dimensional cartoon-like object of the heart, saved, for example, as an object (".obj") file, and added to the rendering as a heart object. The heart object may then be registered as discussed above to other depicted images, such as fluoroscopy images, utilizing known tissue landmarks in multiple views, and contrast agent techniques to particularly see show certain tissue landmarks, such as the outline of an aorta, ventricle, or left atrium. The cartoon heart object may be moved around, by mouse, for example, until it is appropriately registered in various views, such as anterior/posterior and lateral, with the other overlaid objects.

Figure 47:
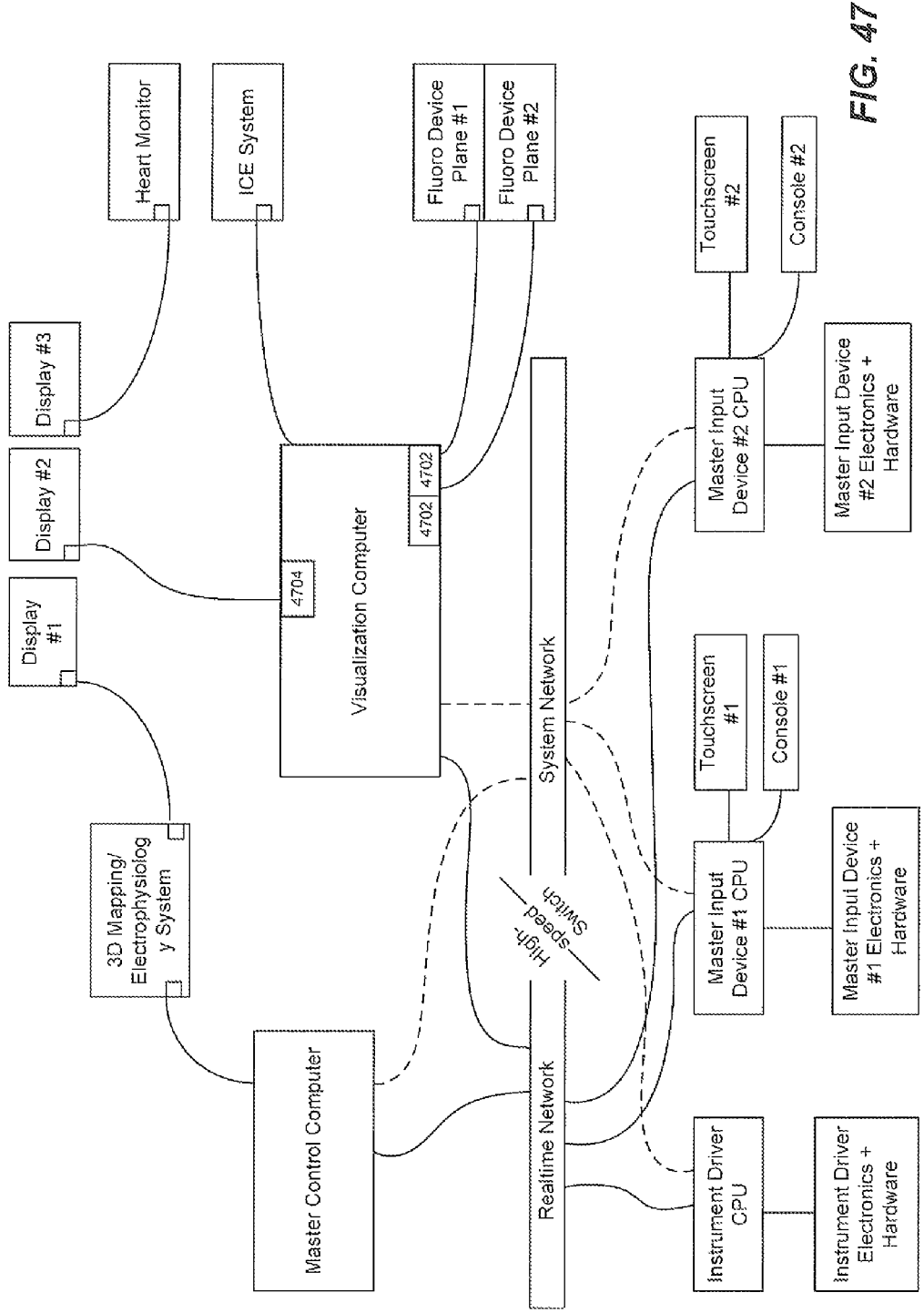

Referring to FIG. 47, a distributed system architecture embodiment is depicted. A master control computer running a real-time operating system, such as QNX, is connected to each of the other computers in the system by a 1 gigabit Ethernet "Real-time Network", and also by a 100 megabit Ethernet "System Network", using a conventional high-speed switch. This enables localized custom computing for various devices to be pushed locally near the device, without the need for large cabling or a central computing machine. In one embodiment, the master control computer may be powered by an Intel® Xeon® processor available from Intel Corporation of Santa Clara, Calif., the visualization computer powered by a personal computer (PC) with a high-end microprocessor based on the Intel architecture running Windows XP and having multiple video cards and frame grabbers, the instrument driver and master input device CPUs being PC or "EPIC" standard boards with two Ethernet connections for the two networks. An additional master input device, touchscreen, and console may be configured into an addition operator workstation in a different location relative to the patient. The system is very expandable—new devices may be plugged into the switch and placed onto either of the two networks.

Referring to FIG. 47, two high resolution frame grabber boards 4702 acquire images from two fluoro devices (or one in the case of single plane fluoro), which a nominal resolution frame grabber board 4702 acquires images from an intracardiac echo system. Such image data may be utilized for overlaying, etc, as described in reference to FIGS. 44-46, and displayed on a display, such as the #2 display, using a video card 4704 of the visualization computer, as depicted. Heart monitor data, from a system such as the Prucka CardioLab EP System distributed by GE Healthcare of Waukesha, Wis., may be directly channeled from video out ports on the heart monitor device to one of the displays. Such data may also be acquired by a frame grabber. Similarly, electrophysiological mapping and treatment data and images from systems available from distributors such as Endocardial Solutions, Biosense Webster, Inc., etc., may be directed as video to a monitor, or data to a data acquisition board, data bus, or frame grabber. Preferably the master control computer has some interface connectivity with the electrophysiology system as well to enable single master input device driving of such device, etc.

Figure 48:
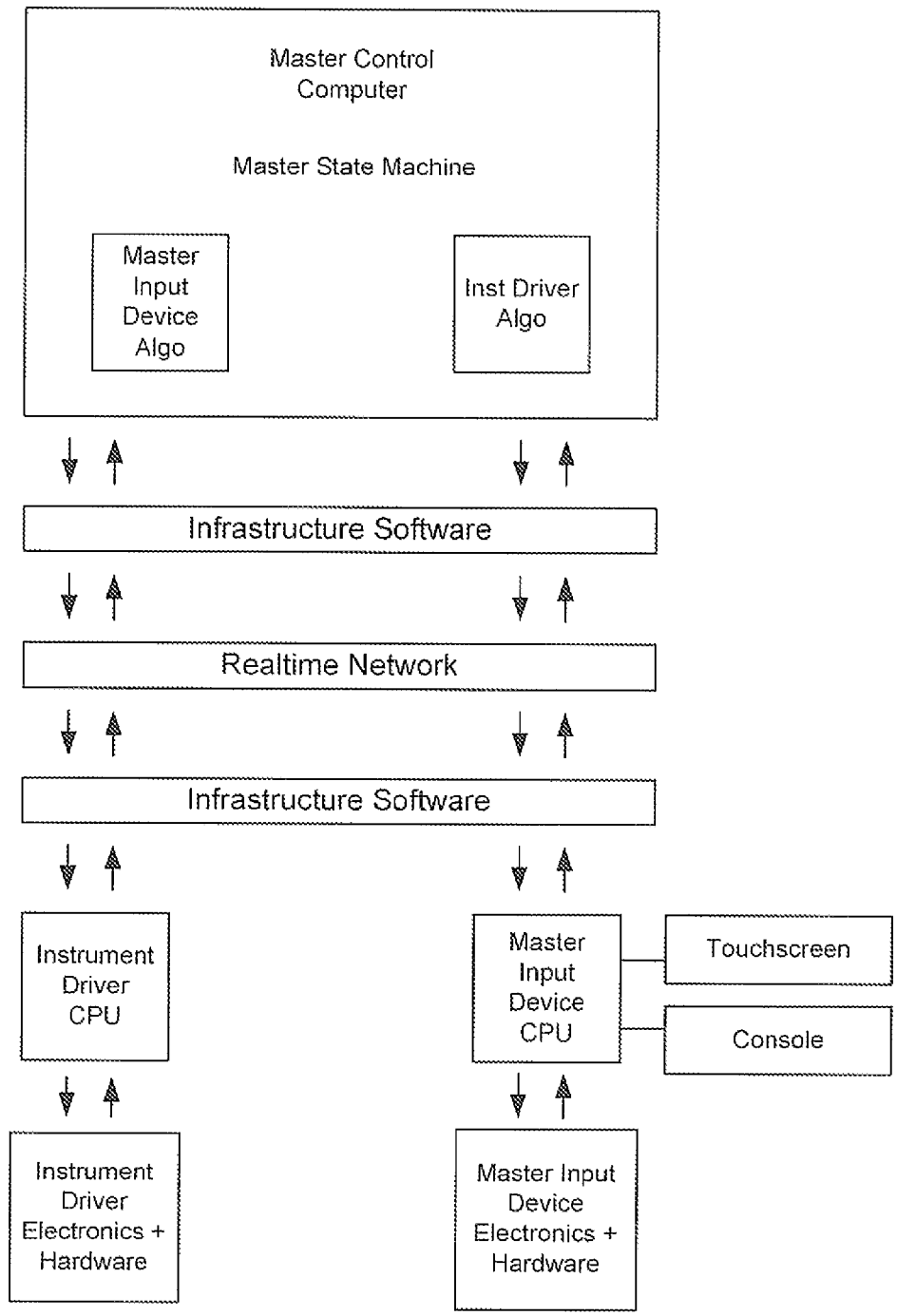
Figure 49:
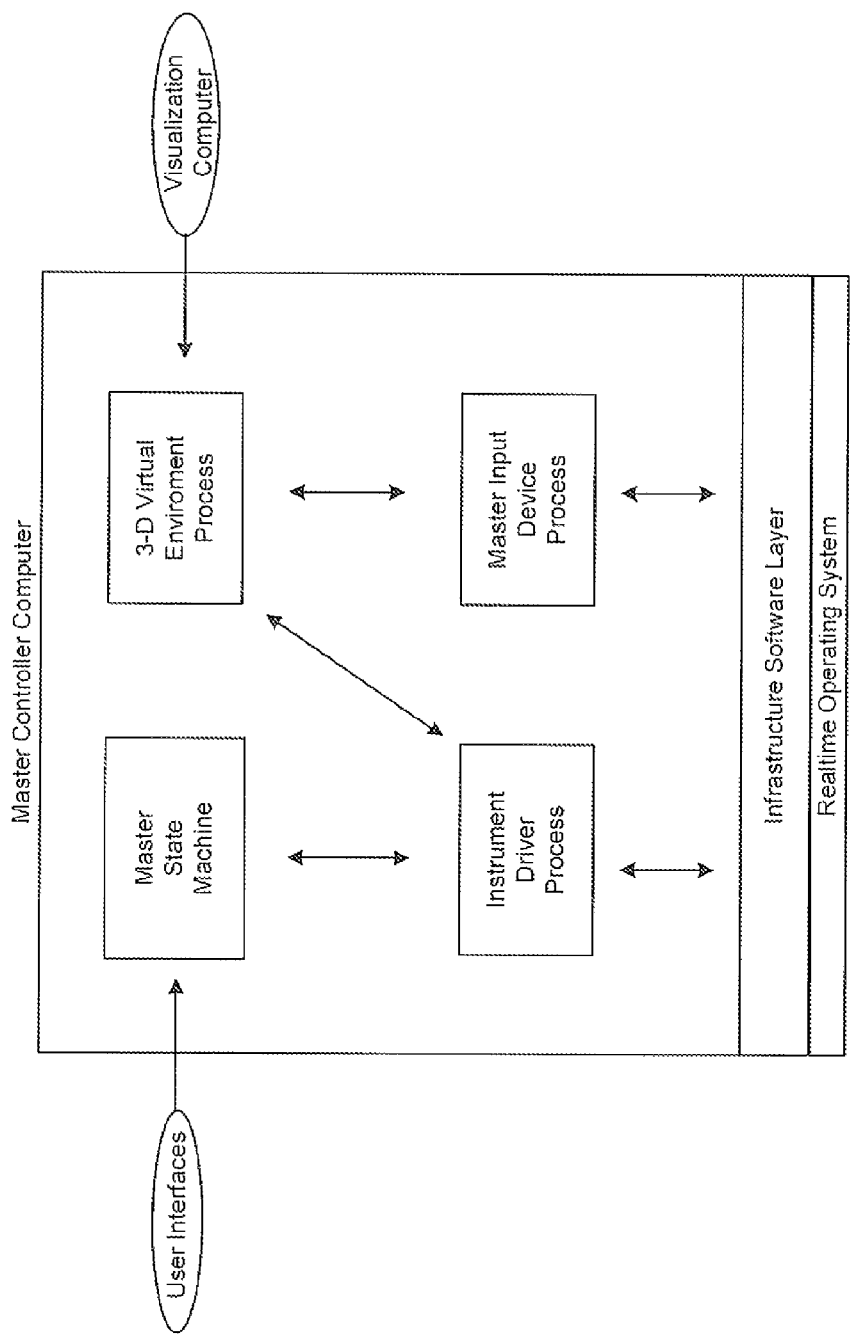

Referring to FIG. 48, a depiction of the software and hardware interaction is depicted. Essentially, the master state machine functionality of the master control system real-time operating system allows for very low latency control of processes used to operate master input device algorithms and instrument driver algorithms, such as those described in reference to the control systems description above. Indeed, XPC may be utilized to develop algorithm code, but preferably a universal modeling language such as IBM Rational Rose from IBM Corporation of Armonk, N.Y., or Rhapsody of I-Logix of Andover, Mass., is utilized to build code and documentation using a graphical interface. With the gigabit real-time network, in a matter of 200-300 microseconds, the master input device or instrument driver algorithms are able to communicate with FPGA driver code in the electronics and hardware near the pertinent device to exchange new values, etc, and confirm that all is well from a safety perspective. This leaves approximately 700 microseconds for processing if a 1 millisecond motor shutoff time is required if all is not well—and this is easily achievable with the described architecture. The visualization PC may be configured to cycle data from the master control computer at a lower frequency, about 20 milliseconds. FIG. 49 illustrates the software interaction of one embodiment.

Although particular embodiments have been shown and described, it should be understood that the above discussion is not intended to limit the scope of these embodiments. Various aspects of embodiments are described and illustrated for purposes of explanation. Many combinations and permutations of the disclosed embodiments are useful in minimally invasive surgery, and the system is configured to be flexible for use with other system components and in other applications. Thus, various changes and modifications may be made without departing from the scope of the claims.

For example, although certain embodiment are described with reference to optical fiber bend sensors having three fibers, other numbers of fibers may be utilized, and configured in an arrangement other than a triangular arrangement. Further, each fiber of an optical fiber sensor may include one or multiple gratings, which may be the same or different lengths, or have the same or different spacing. Thus, gratings may be uniform or non-uniform. Various multiplexing methods and combinations thereof may be utilized.

Further, embodiments that are utilized in robotic surgical applications involving elongate instruments and other components may be utilized with manually or robotically steerable instruments, such as those described in the aforementioned patent application, U.S. Ser. No. 11/637,951.

Embodiments that are utilized in robotic surgical applications may involve use of a rotational apparatus that can be adapted for attachment to a known catheter, e.g., to convert the catheter having an optical fiber sensor coupled thereto or integrated therein into a catheter having a rotatably controllably distal end. For example, the outer body can be attached to a sheath, and the inner body can be attached to a guide catheter such that the distal end of the resulting structure can be controllably rotated with pull wires or control elements. Accordingly, figures showing embodiments in the context of various system configurations are provided as illustrative examples of how a rotational apparatus may be utilized, but it should be understood that embodiments and their applications are not so limited and can be operably coupled to various components and catheters of a robotic instrument system, and that these various components may or may not include optical fiber sensors.

Further, embodiments utilized in robotic surgical applications may involve a multi-segment sheath catheter includes an optical fiber sensor, substantially rigid platform can be formed from one, two, three and other numbers of such sheath catheters, which may assume curved and/or linear configurations, and may be used with another instrument, such as an endoscope or other image capture device. Further, multiple sheath catheters may form one or multiple platforms. Multiple sheath catheters may be advanced through a common lumen, or through individual lumens defined by a master sheath. Further, in certain embodiments, certain substantially rigid sheath catheters may have a linear or straight shape, and other substantially rigid sheath catheters may have a curved or arcuate shape. For this purpose, segments of a sheath catheter may have the same or similar shapes and sizes, or different shapes and/or sizes in order to implement the desired curved or straight shape when the sheath catheter is transitioned from a flexible state and deployed to have a substantially rigid state to form a platform or a part thereof. Segment shapes other than those shapes described and illustrated may be utilized, and a control element or pull wire may extend through walls of one or more segments, or be coupled to an outer surface of one or more segments. Further, segments may have various other interlocking surfaces or faces that prevent rotation and contribute to a substantially rigid structure.

Moreover, although certain embodiments are described with reference to a telemanipulation system or robotic control system, embodiments may also be manually controlled by a surgeon, e.g., near the proximal section of the sheath catheter. Embodiments are advantageously suited for minimally invasive procedures, they may also be utilized in other, more invasive procedures that utilize extension tools and may be used in surgical procedures other than treatment of arrhythmias such as atrial fibrillation.

Because one or more components of embodiments may be used in minimally invasive surgical procedures, the distal portions of these instruments may not be easily visible to the naked eye. As such, embodiments of the invention may be utilized with various imaging modalities such as magnetic resonance (MR), ultrasound, computer tomography (CT), X-ray, fluoroscopy, etc. may be used to visualize the surgical procedure and progress of these instruments. It may also be desirable to know the precise location of any given catheter instrument and/or tool device at any given moment to avoid undesirable contacts or movements. Thus, embodiments may be utilized with localization techniques that are presently available may be applied to any of the apparatuses and methods disclosed above. Further, a plurality of sensors, including those for sensing patient vitals, temperature, pressure, fluid flow, force, etc., may be combined with the various embodiments of flexible catheters and distal orientation platforms.

Various robotic instrument system components that may include or be utilized with embodiments may include catheter components that are made with materials and techniques similar to those described in detail in U.S. patent application Ser. No. 11/176,598, incorporated by reference herein in its entirety. Further, various materials may be used to fabricate and manufacture sheath catheter segment, rotatable apparatus and orientation platform devices. For example, it is contemplated that in addition to that disclosed above, materials including, but not limited to, stainless steel, copper, aluminum, nickel-titanium alloy (Nitinol), Flexinol® (available from Toki of Japan), titanium, platinum, iridium, tungsten, nickel-chromium, silver, gold, and combinations thereof, may be used to manufacture components such as control elements, control cables, segments, gears, plates, ball units, wires, springs, electrodes, thermocouples, etc. Similarly, non-metallic materials including, but not limited to, polypropylene, polyurethane (Pebax®), nylon, polyethylene, polycarbonate, Delrin®, polyester, Kevlar®, carbon, ceramic, silicone, Kapton® polyimide, Teflon® coating, polytetrafluoroethylene (PTFE), plastic (non-porous or porous), latex, polymer, etc. may be used to make the various parts of a catheter, orientation platform, tool, etc.

Additionally, certain surgical system components are described as having lumens that are configured for carrying or passage of control elements, control cables, wires, and other catheter instruments. Such lumens may also be used to deliver fluids such as saline, water, carbon dioxide, nitrogen, helium, for example, in a gaseous or liquid state, to the distal tip. Further, some embodiments may be implemented with a open loop or closed loop cooling system wherein a fluid is passed through one or more lumens in the sidewall of the catheter instrument to cool the catheter or a tool at the distal tip. Surgical systems that utilized or include embodiments may be utilized with various working instruments including end effectors including, for example, a Kittner dissector, a multi-fire coil tacker, a clip applier, a cautery probe, a shovel cautery instrument, serrated graspers, tethered graspers, helical retraction probe, scalpel, basket capture device, irrigation tool, needle holders, fixation device, transducer, and various other graspers. A number of other catheter type instruments may also be utilized together with certain embodiments including, but not limited to, a mapping catheter, an ablation catheter, an ultrasound catheter, a laser fiber, an illumination fiber, a wire, transmission line, antenna, a dilator, an electrode, a microwave catheter, a cryo-ablation catheter, a balloon catheter, a stent delivery catheter, a fluid/drug delivery tube, a suction tube, an optical fiber, an image capture device, an endoscope, a Foley catheter, Swan-Ganz catheter, fiberscope, etc. Thus, it is contemplated that one or more catheter instruments may be inserted through one or more lumens of a flexible catheter instrument, flexible sheath instrument, or any catheter instrument to reach a surgical site at the distal tip. Similarly, it is contemplated that one or more catheter instruments may be passed through an orientation platform to a region of interest.

Additionally, although certain embodiments are described with reference to surgical robotics for minimally invasive procedures, embodiments may also be utilized in other non-surgical applications and with other systems and methods including, but not limited to, various manufacturing and industrial applications, optics, communications, civil engineering and structural analysis and monitoring, seismology, and other applications involving fiber sensors and force and/or bending measurements and related monitoring/detection applications. For example, embodiments of high density multiplexing of fiber grating sensors may be utilized with an industrial robot that has a distal end sensor that is used to perform integrity checks, e.g., to detect cracks within a mechanical structure or manufactured component. For example, embodiments may be used for analysis or examination of aeronautical components such as an airplane wing or other structural or manufactured components. As another example, embodiments may be utilized in civil engineering and structural applications, e.g., for monitoring stresses or forces on certain structures such as bridges and buildings. Depending on the application, embodiments may be implemented within or attached to a robotic arm, e.g., a multi-segment robotic arm, and the particular shape, size, and configuration of a robotic and fibers and gratings may vary depending on the application manner in which embodiments are utilized. Accordingly, one of ordinary skill in the art having the benefit of this disclosure would appreciate that variations of the invention may be applied to numerous non-surgical applications and general robotic applications.

Further, while multiple embodiments and variations of the many aspects of the invention have been disclosed and described herein, such disclosure is provided for purposes of illustration only. Many combinations and permutations of the disclosed system are useful in various robotic systems, including minimally invasive surgical robots. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, it should be understood that the invention generally, as well as the specific embodiments described herein, are not limited to the particular forms or methods disclosed, but also cover all modifications, equivalents and alternatives falling within the scope of the appended claims.

What is claimed is:

1. A Bragg sensor system, comprising:
    a plurality of single core optical fibers assembled into a fiber sensor configuration in which the respective fiber cores are aligned substantially parallel to one another, each fiber core having written thereon one or more Bragg grating arrays,
    wherein at least one of the optical fibers has a distribution of Bragg gratings in which a density of gratings in a proximal portion of the respective fiber is lower than a density of gratings in a distal portion of the respective fiber.

2. The system of claim 1, the plurality of optical fibers comprising three optical fibers bonded together in a triangular geometry and having lengths suitable to support bending measurements.

3. The system of claim 2, further comprising a hard coating material applied over a grating region of the bonded optical fibers to facilitate transfer of strain between fibers during subsequent bending.

4. The system of claim 3, wherein respective ends of the optical fibers are separated from one another extending out of one end of the coated grating region.

5. A system of claim 4, wherein the separated fiber ends of the sensor configuration are coupled to respective coupling connectors configured for interfacing with a grating output unit.

6. The system of claim 4, wherein the separated fiber ends are fusion spliced to respective larger diameter fibers that in turn are secured to the respective coupling connectors.

7. The system of claim 6, each optical fiber having written thereon one or more Bragg grating arrays, the system further comprising a multi-port tunable light source system having at least three ports configured for coupling to the respective coupling connectors, the one or more Bragg grating arrays comprising respective multiplexed Bragg grating arrays on the respective fiber cores of the fiber sensor configuration, the tunable light source system further comprising respective beamsplitter and detector assemblies used to read out the respective multiplexed grating arrays.

8. The system of claim 7, the tunable light source system further comprising an array of Bragg gratings on a fourth port to measure temperature.

9. The system of claim 7, further comprising a spectrally broadband light source including a dispersive output unit coupled to the bonded optical fibers via the respective connectors.

10. The system of claim 9, wherein the dispersive output unit comprises one or more bulk gratings and a detector array.

11. A medical treatment system including the Bragg sensor system of claim 1, the treatment system including an elongate instrument to which the fiber sensor configuration is coupled.

12. The medical treatment system of claim 11, wherein movement of the elongate instrument is robotically controlled based at least in part upon position information obtained from the Bragg sensor system.

13. The medical treatment system of claim 11, the instrument comprising an elongate guide catheter having a bendable distal section, the Bragg sensor system being coupled to the bendable distal section of the instrument, wherein bending of the instrument distal section is robotically controlled based at least in part upon position information provided by the Bragg sensor system.

14. A medical treatment system of claim 11, further comprising a tissue manipulation tool coupled to a distal end portion of the instrument.

15. A medical treatment system of claim 11, wherein the instrument comprises a plurality of joints, and wherein respective movements of the joints are controlled based at least in part upon position information obtained from the Bragg sensor system.

16. A medical treatment system of claim 11, wherein the instrument further comprises an interface, and wherein an orientation of the interface is controlled based at least in part upon position information obtained from the Bragg sensor system.

17. The system of claim 1, the optical fibers having diameters in a range of about 40 microns to about 70 microns.

18. The system of claim 1, wherein the optical fibers are aligned substantially parallel to one another and bonded together to form a fiber sensor configuration having a length of about 1.5 meters to about 2.0 meters.

19. A system, comprising:
- an elongate catheter instrument having a distal portion and a proximal portion that is more rigid than the distal portion; and
- a Bragg sensor optical fiber coupled to the catheter instrument and comprising at least one optical fiber core having a distribution of Bragg gratings in which a number of gratings in a portion of the fiber core coupled to the proximal portion of the catheter instrument is lower than a number of gratings in a portion of the fiber core coupled to the distal portion of the catheter.

20. The system of claim 19, comprising a plurality of single core optical fibers assembled in a configuration in which the respective fiber cores are aligned substantially parallel to one another, each fiber core having written thereon respective multiplexed Bragg grating arrays.

21. The system of claim 19, wherein the multiplexed fiber gratings are supported by each of amplitude, spectrum and wavelength measurements.

\* \* \* \* \*